US008540984B2

(12) United States Patent
Lei

(10) Patent No.: US 8,540,984 B2
(45) Date of Patent: Sep. 24, 2013

(54) PHYTASES WITH IMPROVED THERMAL STABILITY

(75) Inventor: Xingen Lei, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 732 days.

(21) Appl. No.: 12/375,432

(22) PCT Filed: Aug. 3, 2007

(86) PCT No.: PCT/US2007/075181
§ 371 (c)(1),
(2), (4) Date: Sep. 2, 2009

(87) PCT Pub. No.: WO2008/017066
PCT Pub. Date: Feb. 7, 2008

(65) Prior Publication Data
US 2010/0068335 A1   Mar. 18, 2010

Related U.S. Application Data

(60) Provisional application No. 60/821,347, filed on Aug. 3, 2006.

(51) Int. Cl.
C12N 9/16 (2006.01)
A23J 3/14 (2006.01)

(52) U.S. Cl.
USPC .......................... 424/94.6; 435/194; 435/196

(58) Field of Classification Search
USPC .................. 435/196, 252.3, 320.1; 536/23.2
See application file for complete search history.

(56) References Cited

U.S. PATENT DOCUMENTS

| 3,819,528 A | 6/1974 | Berry |
| 3,860,484 A | 1/1975 | O'Malley |
| 3,966,971 A | 6/1976 | Morehouse et al. |
| 4,038,140 A | 7/1977 | Jaworek et al. |
| 4,375,514 A | 3/1983 | Siewert et al. |
| 4,460,683 A | 7/1984 | Gloger et al. |
| 4,470,968 A | 9/1984 | Mitra et al. |
| 4,734,283 A | 3/1988 | Sirén |
| 4,765,994 A | 8/1988 | Holmgren |
| 4,778,761 A | 10/1988 | Miyanohara et al. |
| 4,914,029 A | 4/1990 | Caransa et al. |
| 4,915,960 A | 4/1990 | Holmgren |
| 4,950,609 A | 8/1990 | Tischer et al. |
| 4,997,767 A | 3/1991 | Nozaki et al. |
| 5,024,941 A | 6/1991 | Maine et al. |
| 5,200,399 A | 4/1993 | Wettlaufer et al. |
| 5,268,273 A | 12/1993 | Buckholz |
| 5,290,765 A | 3/1994 | Wettlaufer et al. |
| 5,316,770 A | 5/1994 | Edwards, Jr. |
| 5,318,903 A | 6/1994 | Bewert et al. |
| 5,366,736 A | 11/1994 | Edwards, Jr. |
| 5,436,156 A | 7/1995 | Van Gorcom et al. |
| 5,443,979 A | 8/1995 | Vanderbeke et al. |
| 5,480,790 A | 1/1996 | Tischer et al. |
| 5,492,821 A | 2/1996 | Callstrom et al. |
| 5,516,525 A | 5/1996 | Edwards, Jr. |
| 5,554,399 A | 9/1996 | Vanderbeke et al. |
| 5,556,771 A | 9/1996 | Shen et al. |
| 5,593,963 A | 1/1997 | Van Ooijen et al. |
| 5,612,055 A | 3/1997 | Bedford et al. |
| 5,691,154 A | 11/1997 | Callstrom et al. |
| 5,716,655 A | 2/1998 | Hamstra et al. |
| 5,736,625 A | 4/1998 | Callstrom et al. |
| 5,780,292 A | 7/1998 | Nevalainen et al. |
| 5,827,709 A | 10/1998 | Barendse et al. |
| 5,830,696 A | 11/1998 | Short |
| 5,830,733 A | 11/1998 | Nevalainen et al. |
| 5,834,286 A | 11/1998 | Nevalainen et al. |
| 5,853,779 A | 12/1998 | Takebe et al. |
| 5,863,533 A | 1/1999 | Van Gorcom et al. |
| 5,876,997 A | 3/1999 | Kretz |
| 5,891,708 A | 4/1999 | Saniez et al. |
| 5,900,525 A | 5/1999 | Austin-Phillips et al. |
| 5,902,615 A | 5/1999 | Saniez et al. |
| 5,935,624 A | 8/1999 | DeLuca et al. |
| 5,955,448 A | 9/1999 | Colaco et al. |
| 5,972,669 A | 10/1999 | Harz et al. |
| 5,985,605 A | 11/1999 | Cheng et al. |
| 5,989,600 A | 11/1999 | Nielsen et al. |
| 6,022,555 A | 2/2000 | DeLuca et al. |

(Continued)

FOREIGN PATENT DOCUMENTS

| CN | 1126243 A1 | 7/1996 |
| EP | 0 420 358 A1 | 4/1991 |

(Continued)

OTHER PUBLICATIONS

ATCC Yeasts: 1995 Sales Catalog 20-22 (19$^{th}$ ed. 1995).
Atlung & Brøndsted, "Role of the Transcriptional Activator AppY in Regulation of the cyx appA Operon of Escherichia coli by Anaerobiosis, Phosphate Starvation, and Growth Phase," J. Bacteriol. 176(17):5414-22 (1994).
Belin et al., "A Pleiotropic Acid Phosphatase-Deficient Mutant of Escherichia coli Shows Premature Termination in the dsbA Gene. Use of dsbA::phoA Fusions to Localize a Structurally Important Domain in DsbA," Mol. Gen. Genet. 242:23-32 (1994).
Blondeau et al., "Development of High-Cell-Density Fermentation for Heterologous Interleukin 1β Production in Kluyveromyces lactis Controlled by the PHO5 Promoter," Appl. Microbiol. Biotech. 41:324-29 (1994).

(Continued)

Primary Examiner — Tekchand Saidha
(74) Attorney, Agent, or Firm — LeClairRyan, a Professional Corporation

(57) ABSTRACT

The invention provides variant phytase enzymes having increased thermal stability relative to their counterpart parent enzymes. The modifications to the enzymes include both single substitutions and various combinations of substitutions that provide improved stability and activity. The invention further provides nucleic acids encoding the variant phytase enzymes, host cells and vectors containing and expressing them, as well as feed compositions useful for providing improved nutrition, particularly with respect to the bioavailability of dietary phosphate, calcium, iron and zinc, among others.

65 Claims, 15 Drawing Sheets

(56) References Cited

U.S. PATENT DOCUMENTS

| | | | |
|---|---|---|---|
| 6,039,942 A | 3/2000 | Lassen et al. |
| 6,063,431 A | 5/2000 | Bae et al. |
| 6,083,541 A | 7/2000 | Hamstra et al. |
| 6,110,719 A | 8/2000 | Kretz |
| 6,139,892 A | 10/2000 | Fredlund et al. |
| 6,139,902 A | 10/2000 | Kondo et al. |
| 6,140,077 A | 10/2000 | Nakamura et al. |
| 6,183,740 B1 | 2/2001 | Short et al. |
| 6,190,897 B1 | 2/2001 | Kretz |
| 6,204,012 B1 | 3/2001 | Hellmuth et al. |
| 6,248,938 B1 | 6/2001 | Austin-Phillips et al. |
| 6,261,592 B1 | 7/2001 | Nagashima et al. |
| 6,264,946 B1 | 7/2001 | Müllertz et al. |
| 6,274,178 B1 | 8/2001 | Beven et al. |
| 6,277,623 B1 | 8/2001 | Oh et al. |
| 6,284,502 B1 | 9/2001 | Maenz et al. |
| 6,291,221 B1 | 9/2001 | Van Loon et al. |
| 6,309,870 B1 | 10/2001 | Kondo et al. |
| 6,350,602 B1 | 2/2002 | Van Gorcom et al. |
| 6,391,605 B1 | 5/2002 | Kostrewa et al. |
| 6,451,572 B1 | 9/2002 | Lei |
| 6,475,762 B1 | 11/2002 | Stafford et al. |
| 6,511,699 B1 | 1/2003 | Lei |
| 6,514,495 B1 | 2/2003 | Svendsen et al. |
| 6,599,735 B1 | 7/2003 | Bartók et al. |
| 6,720,014 B1 | 4/2004 | Short et al. |
| 6,720,174 B1 | 4/2004 | Lehmann |
| 6,841,370 B1 | 1/2005 | Lei |
| 6,855,365 B2 | 2/2005 | Short et al. |
| 6,974,690 B2 | 12/2005 | Lei |
| 7,022,371 B2 | 4/2006 | Stafford et al. |
| 7,026,150 B2 | 4/2006 | Lei |
| 7,078,035 B2 | 7/2006 | Short et al. |
| 7,135,323 B2 | 11/2006 | Lanahan et al. |
| 7,300,781 B2 | 11/2007 | Lei |
| 7,309,505 B2 | 12/2007 | Lei et al. |
| 7,312,063 B2 | 12/2007 | Lei |
| 7,320,876 B2 | 1/2008 | Webel et al. |
| 7,432,097 B2 * | 10/2008 | Short et al. ............ 435/196 |
| 7,736,680 B2 | 6/2010 | Lei et al. |
| 7,829,318 B2 | 11/2010 | Lei |
| 7,833,743 B2 | 11/2010 | Webel et al. |
| 7,919,297 B2 | 4/2011 | Lei |
| 7,972,805 B2 | 7/2011 | Webel et al. |
| 8,192,734 B2 | 6/2012 | Lei |
| 8,334,124 B1 | 12/2012 | Mullaney et al. |
| 2001/0018197 A1 | 8/2001 | Wong et al. |
| 2001/0029042 A1 | 10/2001 | Fouache et al. |
| 2002/0068350 A1 | 6/2002 | Kondo et al. |
| 2002/0102692 A1 | 8/2002 | Lei |
| 2002/0127218 A1 | 9/2002 | Svendsen et al. |
| 2002/0136754 A1 | 9/2002 | Short et al. |
| 2002/0192791 A1 | 12/2002 | Lei |
| 2003/0072844 A1 | 4/2003 | Lei |
| 2003/0092155 A1 | 5/2003 | Kostrewa et al. |
| 2003/0206913 A1 | 11/2003 | Webel et al. |
| 2004/0126844 A1 | 7/2004 | Lei et al. |
| 2005/0095691 A1 | 5/2005 | Lei |
| 2006/0153902 A1 | 7/2006 | Lei |
| 2006/0292636 A1 | 12/2006 | Yarnall et al. |
| 2007/0196449 A1 | 8/2007 | Lei |
| 2008/0227150 A1 | 9/2008 | Lei |
| 2009/0028994 A1 | 1/2009 | Lei et al. |
| 2009/0074909 A1 | 3/2009 | Webel et al. |
| 2009/0155237 A1 | 6/2009 | Lei |
| 2010/0068335 A1 | 3/2010 | Lei |
| 2011/0053246 A1 | 3/2011 | Lei |
| 2011/0086127 A1 | 4/2011 | Webel et al. |

FOREIGN PATENT DOCUMENTS

| | | |
|---|---|---|
| EP | 0 449 376 A2 | 10/1991 |
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A2 | 4/1999 |
| EP | 0 925 723 A1 | 6/1999 |
| EP | 0 955 362 A1 | 11/1999 |
| EP | 0 960 934 A1 | 12/1999 |
| EP | 1 090 129 B1 | 2/2006 |
| GB | 2 286 396 A | 8/1995 |
| GB | 2 316 082 A | 2/1998 |
| JP | 10276789 | 10/1998 |
| JP | 2001-514869 A | 9/2001 |
| JP | 2001-292789 | 10/2001 |
| RU | 2 113 468 C1 | 6/1998 |
| WO | WO 86/01179 A1 | 2/1986 |
| WO | WO 90/03431 A1 | 4/1990 |
| WO | WO 90/05182 A1 | 5/1990 |
| WO | WO 91/05053 A1 | 4/1991 |
| WO | WO 91/14773 A2 | 10/1991 |
| WO | WO 91/14782 A1 | 10/1991 |
| WO | WO 93/14645 A1 | 8/1993 |
| WO | WO 93/16175 A1 | 8/1993 |
| WO | WO 93/19759 A1 | 10/1993 |
| WO | WO 94/03072 A1 | 2/1994 |
| WO | WO 94/03612 A1 | 2/1994 |
| WO | WO 97/16076 A1 | 5/1997 |
| WO | WO 97/35017 A1 | 9/1997 |
| WO | WO 97/39638 A1 | 10/1997 |
| WO | WO 97/45009 A2 | 12/1997 |
| WO | WO 97/48812 A3 | 12/1997 |
| WO | WO 97/48813 A2 | 12/1997 |
| WO | WO 98/05785 A1 | 2/1998 |
| WO | WO 98/06856 A1 | 2/1998 |
| WO | WO 98/20139 A2 | 5/1998 |
| WO | WO 98/30681 A1 | 7/1998 |
| WO | WO 98/44125 A1 | 10/1998 |
| WO | WO 98/54980 A2 | 12/1998 |
| WO | WO 99/08539 A1 | 2/1999 |
| WO | WO 99/49022 A1 | 9/1999 |
| WO | WO 99/49740 A1 | 10/1999 |
| WO | WO 99/67398 A3 | 12/1999 |
| WO | WO 00/10404 A3 | 3/2000 |
| WO | WO 00/20569 A1 | 4/2000 |
| WO | WO 00/41509 A3 | 7/2000 |
| WO | WO 00/43503 A1 | 7/2000 |
| WO | WO 00/47060 A1 | 8/2000 |
| WO | WO 00/58481 A2 | 10/2000 |
| WO | WO 00/71728 A1 | 11/2000 |
| WO | WO 00/72700 A1 | 12/2000 |
| WO | WO 01/36607 A1 | 5/2001 |
| WO | WO 01/58275 A2 | 8/2001 |
| WO | WO 01/58276 A2 | 8/2001 |
| WO | WO 01/89317 A2 | 11/2001 |
| WO | WO 01/90333 A2 | 11/2001 |
| WO | WO 02/48332 A2 | 6/2002 |
| WO | WO 2007/112739 A1 | 10/2007 |
| WO | WO 2010/122532 A2 | 10/2010 |

OTHER PUBLICATIONS

Boctor & Mehta, "Enhancement of the Stability of Thrombin by Polyols: Microcalorimetric Studies," *J. Pharm. Pharmacol.* 44:600-03 (1992).
Boer et al., "Characterization of *Trichoderma reesei* Cellobiohydrolase Cel7A Secreted from *Pichia pastoris* Using Two Different Promoters," *Biotech. Bioeng.* 69(5):486-94 (2000).
Brazilian Patent Application No. PI0009516-8, Technical Examination Report (Jan. 11, 2010).
Brazilian Patent Application No. PI0009516-8, Technical Examination Report (Oct. 20, 2010).
Brazilian Patent Application No. PI0009516-8, Technical Examination Report (May 30, 2011).
Brazilian Patent Application No. PI9911549-2, Technical Examination Report (Jun. 18, 2010).
Brazilian Patent Application No. PI9911549-2, Technical Examination Report (Feb. 9, 2011).
Brazilian Patent Application No. PI9911549-2, Technical Examination Report (Jan. 26, 2012).

Brøndsted & Atlung, "Effect of Growth Conditions on Expression of the Acid Phosphatase (*cyx-appA*) Operon and the *appY* Gene, Which Encodes a Transcriptional Activator of *Escherichia coli*," *J. Bacteriol.* 178(6):1556-64 (1996).

Canadian Patent Application No. 2,332,180, Office Action (Apr. 6, 2011).

Chiarugi et al., "Differential Role of Four Cysteines on the Activity of a Low $M_r$ Phosphotyrosine Protein Phosphatase," *FEBS Lett.* 310(1):9-12 (1992).

Cromwell, "Phytase Appears to Reduce Phosphorus in Feed, Manure," *Feedstuffs* 63:14-16 (1991).

Curry et al., "Expression and Secretion of a *Cellulomonas fimi* Exoglucanase in *Saccharomyces cerevisiae*," *Appl. Environ. Microbiol.* 54(2):476-84 (1988).

Dassa & Boquet, "Identification of the Gene *appA* for the Acid Phosphatase (pH Optimum 2.5) of *Escherichia coli*," *Mol. Gen. Genet.* 200:68-73 (1985).

Dassa et al., "The Acid Phosphatase with Optimum pH of 2.5 of *Escherichia coli*," *J. Biol. Chem.* 257(12):6669-76 (1982).

Dassa et al., "The Complete Nucleotide Sequence of the *Escherichia coli* Gene *appA* Reveals Significant Homology Between pH 2.5 Acid Phosphatase and Glucose-1-Phosphatase," *J. Bacteriol.* 172(9):5497-500 (1990).

Divakaran & Ostrowski, "In Vitro Studies on the Interaction of Phytase with Trypsin and Amylase Extracted from Shrimp (*Penaeus vannamei*) Hepatopancreas," *J. Agric. Food Chem.* 46:4973-76 (1998).

Eisenthal et al., "The Thermal Behaviour of Enzyme Activity: Implications for Biotechnology," *Trends Biotech.* 24(7):289-92 (2006).

European Patent Application No. 00978762.3, Communication Pursuant to Article 94(3) EPC (Mar. 2, 2010).

European Patent Application No. 06075318.3, Communication Pursuant to Article 94(3) EPC (Mar. 29, 2012).

Fierobe et al., "Overexpression and Characterization of *Aspergillus awamori* Wild-Type and Mutant Glucoamylase Secreted by the Methylotrophic Yeast *Pichia pastoris*: Comparison with Wild-Type Recombinant Glucoamylase Produced Using *Saccharomyces cerevisiae* and *Aspergillus niger* as Hosts," *Protein Expr. Purif.* 9:159-70 (1997).

Fu et al., "A Highly pH-Stable Phytase from *Yersinia kristeensenii*: Cloning, Expression, and Characterization," *Enzyme Microb. Tech.* 42:499-505 (2008).

Garrett et al., "Enhancing the Thermal Tolerance and Gastric Performance of a Microbial Phytase for Use as a Phosphate-Mobilizing Monogastric-Feed Supplement," *Appl. Environ. Microbiol.* 70(5):3041-46 (2004).

Genbank Accession No. AAB26466 (Oct. 19, 1993) (as updated Nov. 21, 1996).

Genbank Accession No. AAB96872 (Jan. 16, 1998).

Genbank Accession No. AAG40885 (Dec. 27, 2000).

Genbank Accession No. B36733 (Mar. 1, 2002).

Genbank Accession No. M94550 (Apr. 27, 1993).

Genbank Accession No. P34752 (Jan. 25, 2005).

Genbank Accession No. P81440 (Dec. 15, 1998) (as updated Oct. 22, 1999).

Genbank Accession No. PQ0641 (Mar. 17, 1999) (as updated Nov. 21, 2000).

Gentile et al., "Effectiveness of an Experimental Consensus Phytase in Improving Dietary Phytate-Phosphorus Utilization by Weanling Pigs," *J. Anim. Sci.* 81:2751-57 (2003).

Golovan et al., "Characterization and Overproduction of the *E. coli* appA Encoded Bifunctional Enzyme that Exhibits Both Phytase and Acid Phosphatase Activities," *Can. J. Microbiol.* 46:59-71 (2000).

Granovskii et al., "Expression of Hepatitis B Virus HBsAg Gene in Yeast Cells Under Control of Promotor Region of PHO5 Gene," *Sov. Prog. Virol.* 5:45-47 (1985).

Greiner & Jany, "Characterization of a Phytase from *Escherichia coli*," *Herbsttagung Gesellschaft Biol. Chem.* 372:664-65 (1991).

Greiner et al., "Purification and Characterization of a Phytase from *Klebsiella terrigena*," *Arch. Biochem. Biophys.* 341(2):201-06 (1997).

Greiner et al., "Purification and Characterization of Two Phytases from *Escherichia coli*," *Arch. Biochem. Biophys.* 303(1):107-13 (1993).

Gu et al., "Gene Cloning, Expression, and Characterization of a Novel Phytase from *Dickeya paradisiaca*," *Appl. Biochem. Biotech.* 157:113-23 (2009).

Haefner et al., "Biotechnological Production and Applications of Phytases," *Appl. Microbiol. Biotech.* 68:588-97 (2005).

Han & Lei, "Development of Phytase Overexpressing Microbes for Nutritional Use," Poster Presentation at Cornell University's Biotechnology Symposium, Ithaca, New York (Oct. 15, 1997).

Han & Lei, "Role of Glycosylation in the Functional Expression of an *Aspergillus niger* Phytase (*phyA*) in *Pichia pastoris*," *Arch. Biochem. Biophys.* 364(1):83-90 (1999).

Han et al., "Expression of an *Aspergillus niger* Phytase Gene (*phyA*) in *Saccharomyces cerevisiae*," *Appl. Environ. Microbiol.* 65(5):1915-18 (1999).

Han et al., "Supplemental Phytases of Microbial and Cereal Sources Improve Dietary Phytate Phosphorus Utilization by Pigs from Weaning Through Finishing," *J. Anim. Sci.* 75:1017-25 (1997).

Hercz, "Regulation of Bone Remodeling: Impact of Novel Therapies," *Semin. Dial.* 14(1):55-60 (2001) (abstract only).

Jalal & Scheideler, "Effect of Supplementation of Two Different Sources of Phytase on Egg Production Parameters in Laying Hens and Nutrient Digestibility," *Poultry Sci.* 80:1463-71 (2001).

Jia et al., "Purification, Crystallization and Preliminary X-Ray Analysis of the *Escherichia coli* Phytase," *Acta Cryst.* D54:647-49 (1998).

Kanai et al., "Recombinant Thermostable Cycloinulo-Oligosaccharide Fructanotransferase Produced by *Saccharomyces cerevisiae*," *Appl. Environ. Microbiol.* 63(12):4956-60 (1997).

Kerovuo et al., "Isolation, Characterization, Molecular Gene Cloning, and Sequencing of a Novel Phytase from *Bacillus subtilis*," *Appl. Environ. Microbiol.* 64(6):2079-85 (1998).

Kim & Lei, "Enhancing Thermostability of *Escherichia coli* Phytase AppA2 by Error-Prone PCR," *Appl. Microbiol. Biotech.* 79:69-75 (2008).

Kim & Lei, "Improving Thermostability of *Escherichia coli* AppA2 Phytase by Directed Evolution," Poster Presented at the 20th Symposium of The Protein Society (Aug. 5-9, 2006).

Kim et al., "Assembly of Mutations for Improving Thermostability of *Escherichia coli* AppA2 Phytase," *Appl. Microbiol. Biotech.* 79:751-58 (2008).

Kim et al., "Cloning of the Thermostable Phytase Gene (*phy*) from *Bacillus* sp. DS11 and Its Overexpression in *Escherichia coli*," *FEMS Microbiol. Lett.* 162:185-91 (1998).

Kim et al., "Molecular Cloning of the Phytase Gene from *Citrobacter braakii* and Its Expression in *Saccharomyces cerevisiae*," *Biotech. Lett.* 28:33-38 (2006).

Konietzny & Greiner, "Model Systems for Developing Detection Methods for Foods Deriving from Genetic Engineering," *J. Food Comp. Analysis* 10:28-35 (1997).

Kostrewa et al., "Crystal Structure of *Aspergillus niger* pH 2.5 Acid Phosphatase at 2.4 Å Resolution," *J. Mol. Biol.* 288:965-74 (1999).

Kostrewa et al., "Crystal Structure of Phytase from *Aspergillus ficuum* at 2.5 Å Resolution," *Nat. Struct. Biol.* 4(3):185-90 (1997).

Kumagai et al., "Conversion of Starch to Ethanol in a Recombinant *Saccharomyces cerevisiae* Strain Expressing Rice α-Amylase from a Novel *Pichia pastoris* Alcohol Oxidase Promoter," *Nat. Biotech.* 11:606-10 (1993).

Lee et al., "Expression of *Escherichia coli* AppA2 Phytase in Four Yeast Systems," *Biotech. Lett.* 27:327-34 (2005).

Leeson et al., "Efficacy of New Bacterial Phytase in Poultry Diets," *Can. J. Anim. Sci.* 80:527-28 (2000).

Lehmann et al., "Exchanging the Active Site Between Phytases for Altering the Functional Properties of the Enzyme," *Protein Sci.* 9:1866-72 (2000).

Lehmann et al., "From DNA Sequence to Improved Functionality: Using Protein Sequence Comparisons to Rapidly Design a Thermostable Consensus Phytase," *Protein Eng.* 13(1):49-57 (2000).

Lei & Stahl, "Biotechnological Development of Effective Phytases for Mineral Nutrition and Environmental Protection," *Appl. Microb. Biotech.* 57:474-81 (2001).

Lei & Stahl, "Nutritional Benefits of Phytase and Dietary Determinants of its Efficacy," *J. Appl. Anim. Res.* 17:97-112 (2000).
Lei et al., "Calcium Level Affects the Efficacy of Supplemental Microbial Phytase in Corn-Soybean Meal Diets of Weanling Pigs," *J. Anim. Sci.* 72:139-43 (1994).
Lei et al., "Supplemental Microbial Phytase Improves Bioavailability of Dietary Zinc to Weanling Pigs," *J. Nutr.* 123:1117-23 (1993).
Lei et al., "Supplementing Corn-Soybean Meal Diets with Microbial Phytase Linearly Improves Phytate Phosphorus Utilization by Weanling Pigs," *J. Anim. Sci.* 71:3359-67 (1993).
Lim & Reid, "Studies of Reaction Kinetics in Relation to the $T_g$' of Polymers in Frozen Model Systems," in Water Relationships in Food 103-22 (H. Levine & L. Slade eds., 1991).
Lim et al., "Crystal Structure of *Escherichia coli* Phytase and its Complex with Phytate," *Nat. Struct. Biol.* 7(2):108-13 (2000).
Lozano et al., "Effect of Polyols on α-Chymotrypsin Thermostability: A Mechanistic Analysis of the Enzyme Stabilization," *J. Biotech.* 35:9-18 (1994).
Lozano et al., "Influence of Polyhydroxylic Cosolvents on Papain Thermostability," *Enzyme Microb. Tech.* 15:868-73 (1993).
Luo et al., "A Novel Phytase appA from *Citrobacter amalonaticus* CGMCC 1696: Gene Cloning and Overexpression in *Pichia pastoris,*" *Curr. Microbiol.* 55:185-92 (2007).
Makhatadze, "Measuring Protein Thermostability by Differential Scanning Calorimetry," Current Protocols in Science 7.9.1-7.9.14 (Supp.12 1998).
Maugenest et al., "Cloning and Characterization of a cDNA Encoding a Maize Seedling Phytase," *Biochem. J.* 322:511-17 (1997).
Meldgaard & Svendsen, "Different Effects of *N*-Glycosylation on the Thermostability of Highly Homologous Bacterial (1,3-1,4)-β-Glucanases Secreted from Yeast," *Microbiology* 140:159-66 (1994).
Minamiguchi et al., "Secretive Expression of the *Aspergillus aculeatus* Cellulase (FI-CMCase) by *Saccharomyces cerevisiae,*" *J. Fermentation Bioeng.* 79(4):363-66 (1995).
Mitchell et al., "The Phytase Subfamily of Histidine Acid Phosphatases: Isolation of Genes for Two Novel Phytases from the Fungi *Aspergillus terreus* and *Myceliophthora thermophila,*" *Microbiology* 143:245-52 (1997).
Moore et al., "Molecular Cloning, Expression and Evaluation of Phosphohydrolases for Phytate-Degrading Activity," *J. Indust. Microbiol.* 14:396-402 (1995).
Mullaney et al., "Advances in Phytase Research," in 47 Advances in Applied Microbiology 157-99 (Saul L. Neidleman et al. eds., 2000).
Mullaney et al., "Phytase Activity in *Aspergillus fumigatus* Isolates," *Biochem. Biophys. Res. Commun.* 275:759-63 (2000).
Mullaney et al., "Positive Identification of a Lambda gt11 Clone Containing a Region of Fungal Phytase Gene by Immunoprobe and Sequence Verification," *Appl. Microbiol. Biotech.* 35:611-14 (1991).
Mullaney et al., "Site-Directed Mutagenesis of *Aspergillus niger* NRRL 3135 Phytase at Residue 300 to Enhance Catalysis at pH 4.0," *Biochem. Biophys. Res. Commun.* 297:1016-20 (2002).
Murray & Szostak, "Construction of Artificial Chromosomes in Yeast," *Nature* 305:189-93 (1983).
Murry et al., "The Effect of Microbial Phytase in a Pearl Millet-Soybean Meal Diet on Apparent Digestibility and Retention of Nutrients, Serum Mineral Concentration, and Bone Mineral Density of Nursery Pigs," *J. Anim. Sci.* 75:1284-91 (1997).
Nielsen et al., "The Determinants of α-Amylase pH-Activity Profiles," *Protein Eng.* 14(7):505-12 (2001).
Olsen & Thomsen, "Improvement of Bacterial β-Glucanase Thermostability by Glycosylation," *J. Gen. Microbiol.* 137:579-85 (1991).
Opposition Against EP 1090129, Cornell Research Foundation, Inc., [Grounds of Appeal] (Jun. 23, 2009).
Opposition Against EP 1090129, Cornell Research Foundation, Inc., "In Reply to the Observations Submitted by the Opponent Novozymes A/S Dated Nov. 2, 2009" (Dec. 23, 2010).
Opposition Against EP 1090129, Cornell Research Foundation, Inc., "In Response to the Observations Submitted by the Opponent Novozyme A/S Dated Apr. 15, 2011" (Jan. 24, 2012).
Opposition Against EP 1090129, Cornell Research Foundation, Inc., "In Response to the Appeal Brief Dated Jun. 12, 2009" (Jan. 12, 2010).
Opposition Against EP 1090129, Cornell Research Foundation, Inc., "In Response to the Summons to Attend Oral Proceedings Dated May 30, 2008" (Nov. 14, 2008).
Opposition Against EP 1090129, Cornell Research Foundation, Inc., "Statement of Xingen Lei, Ph.D" (Nov. 7, 2008).
Opposition Against EP 1090129, DSM Nutritional Products, "Notice of Opposition to European Patent EP 1 090 129 B" (Nov. 15, 2006).
Opposition Against EP 1090129, European Patent Office, "Summons to Attend Oral Proceedings Pursuant to Rule 115(1)EPC" (Feb. 26, 2008).
Opposition Against EP 1090129, Novozymes A/S, [Response to the Preliminary Opinion of the Opposition Division] (Nov. 11, 2008).
Opposition Against EP 1090129, Novozymes A/S, "Declaration of Dr Lars Kobberøe Skov" (Jun. 12, 2009).
Opposition Against EP 1090129, Novozymes A/S, "Grounds of Appeal by Novozymes A/S" (Jun. 12, 2009).
Opposition Against EP 1090129, Novozymes A/S, "In Response to the Official Communication of Notices of Opposition Dated Dec. 21, 2007" (Aug. 31, 2007).
Opposition Against EP 1090129, Novozymes A/S, "Observations of the Opponent/Appellant" (Apr. 15, 2011).
Opposition Against EP 1090129, Novozymes A/S, "Opposition by Novozymes AS" (Nov. 2006).
Opposition Against EP 1090129, Novozymes A/S, "Reply of Novozymes A/S (OPPO. O1) to the Proprietor's Grounds of Appeal" (Nov. 2009).
Opposition Against EP 1090129, Novozymes A/S, "Second Declaration of Dr Lars Kobberøe Skov" (Apr. 11, 2011).
Ostanin & Van Etten, "Asp$^{304}$ of *Escherichia coli* Acid Phosphatase is Involved in Leaving Group Protonation," *J. Biol. Chem.* 268(28):20778-84 (1993).
Ostanin et al., "Overexpression, Site-Directed Mutagenesis, and Mechanism of *Escherichia coli* Acid Phosphatase," *J. Biol. Chem.* 267(32):22830-36 (1992).
Pagano et al., "Supplemental *Escherichia coli* Phytase and Strontium Enhance Bone Strength of Young Pigs Fed a Phosphorus-Adequate Diet," *J. Nutr.* 137:1795-801 (2007).
Pagano et al., Abstract W130, "Supplemental Dietary Phytase and Strontium Improves Bone Traits of Weanling Pigs Fed a Phosphorus-Adequate Diet," *J. Anim. Sci.* 84(Supp.1):340-41 (Jul. 9, 2006).
Pasamontes et al., "Gene Cloning, Purification, and Characterization of a Heat-Stable Phytase from the Fungus *Aspergillus fumigatus,*" *Appl. Environ. Microbiol.* 63(5):1696-700 (1997).
PCT/US07/75181, International Preliminary Report on Patentability (Feb. 12, 2009).
PCT/US07/75181, International Search Report (Oct. 22, 2008).
PCT/US07/75181, Written Opinion (Oct. 22, 2008).
Phillippy & Mullaney, "Expression of an *Aspergillus niger* Phytase (*phyA*) in *Escherichia coli,*" *J. Agric. Food Chem.* 45:3337-42 (1997).
Piddington et al., "The Cloning and Sequencing of the Genes Encoding Phytase (*phy*) and pH 2.5-Optimum Acid Phosphatase (*aph*) from *Aspergillus niger* var. *awamori,*" *Gene* 133:55-62 (1993).
Rodriguez et al., "Cloning, Sequencing, and Expression of an *Escherichia coli* Acid Phosphatase/Phytase Gene (*appA2*) Isolated from Pig Colon," *Biochem. Biophys. Res. Commun.* 257:117-23 (1999).
Rodriguez et al., "Different Sensitivity of Recombinant *Aspergillus niger* Phytase (r-PhyA) and *Escherichia coli* pH 2.5 Acid Phosphatase (r-AppA) to Trypsin and Pepsin in Vitro," *Arch. Biochem. Biophys.* 365(2):262-67 (1999).
Rodriguez et al., "Expression of the *Aspergillus fumigatus* Phytase Gene in *Pichia pastoris* and Characterization of the Recombinant Enzyme," *Biochem. Biophys. Res. Commun.* 268:373-78 (2000).
Rodriguez et al., "Site-Directed Mutagenesis Improves Catalytic Efficiency and Thermostability of *Escherichia coli* pH 2.5 Acid Phosphatase/Phytase Expressed in *Pichia pastoris,*" *Arch. Biochem. Biophys.* 382(1):105-12 (2000).
Rossi et al., "Stabilization of the Restriction Enzyme *Eco*RI Dried with Trehalose and Other Selected Glass-Forming Solutes," *Biotech. Prog.* 13:609-16 (1997).
Schebor et al., "Glassy State and Thermal Inactivation of Invertase and Lactase in Dried Amorphous Matrices," *Biotech. Prog.* 13:857-63 (1997).

Scott et al., "The Effect of Phosphorus, Phytase Enzyme, and Calcium on the Performance of Layers Fed Corn-Based Diets," *Poultry Sci.* 78:1742-49 (1999).

Sebastian et al., "Apparent Digestibility of Protein and Amino Acids in Broiler Chickens Fed a Corn-Soybean Diet Supplemented with Microbial Phytase," *Poultry Sci.* 76:1760-69 (1997).

Shao et al., "Cloning, Expression, and Characterization of a New Phytase from the Phytopathogenic Bacterium *Pectobacterium wasabiae* DSMZ 18074," *J. Microbiol. Biotech.* 18(7):1221-26 (2008).

Shi et al., "A Novel Phytase Gene *appA* from *Buttiauxella* sp. GC21 Isolated from Grass Carp Intestine," *Aquaculture* 275:70-75 (2008).

Sidhu & Bollon, "Analysis of α-Factor Secretion Signals by Fusing with Acid Phosphatase of Yeast," *Gene* 54:175-84 (1987).

Solovicová et al., "High-Yield Production of *Saccharomycopsis fibuligera* Glucoamylase in *Escherichia col*, Refolding, and Comparison of the Nonglycosylated and Glycosylated Enzyme Forms," *Biochem. Biophys. Res. Commun.* 224:790-95 (1996).

Spink, "Differential Scanning Calorimetry," in 84 Methods in Cell Biology: Biophysical Tools for Biologists vol. I in Vitro Techniques 115-41 (John J. Comeia & H. William Detrich III eds., $1^{st}$ ed. 2008).

Stahl et al., "A New Phytase Expressed in Yeast Effectively Improves the Bioavailability of Phytate Phosphorus to Weanling Pigs," *J. Anim. Sci.* 78:668-74 (2000).

Sun et al., Abstract 19, "Expression of *Aspergillus niger* Phytase in Yeast *Saccharomyces cerevisiae* for Poultry Diet Supplementation," *Poultry Sci.* 76(Supp. 1):5 (1997).

Sun, "Cloning and Expression of Calpain and Phytase Genes for the Improvement of Animal Growth and Nutrition," 59-80, 160-84 (UMI Microform 9725634, 1996) (Ph.D. Thesis, Purdue University).

Sun, Abstract, "Cloning and Expression of Calpain and Phytase Genes for the Improvement of Animal Growth and Nutrition" (Ph.D. Thesis, Purdue University 1996), in Proquest Dissertations and Theses, Sec. 0183 pt. 0475 (ProQuest LLC, 2010).

Takahashi et al., "Independent Production of Two Molecular Forms of a Recombinant *Rhizopus oryzae* Lipase by *KEX2*-Engineered Strains of *Saccharomyces cerevisiae*," *Appl. Microbiol. Biotech.* 52:534-40 (1999).

Takeda & Karsenty, "Central Control of Bone Formation," *J. Bone Miner. Metab.* 19:195-98 (2001) (abstract only).

Terashima et al., "The Roles of the N-Linked Carbohydrate Chain of Rice α-Amylase in Thermostability and Enzyme Kinetics," *Eur. J. Biochem.* 226:249-54 (1994).

Tomschy et al., "Active Site Residue 297 of *Aspergillus niger* Phytase Critically Affects the Catalytic Properties," *FEBS Lett.* 472:169-72 (2000).

Tomschy et al., "Engineering of Phytase for Improved Activity at Low pH," *Appl. Environ. Microbiol.* 68(4):1907-13 (2002).

Tomschy et al., "Optimization of the Catalytic Properties of *Aspergillus fumigatus* Phytase Based on the Three-Dimensional Structure," *Protein Sci.* 9:1304-11 (2000).

Touati & Danchin, "The Structure of the Promoter and Amino Terminal Region of the pH 2.5 Acid Phosphatase Structural Gene (*appA*) of *E. coli*: A Negative Control of Transcription Mediated by Cyclic AMP," *Biochimie* 69:215-21 (1987).

Touati et al., "Pleiotropic Mutations in *appR* Reduce pH 2.5 Acid Phosphatase Expression and Restore Succinate Utilisation in CRP-Deficient Strains of *Escherichia coli*," *Mol. Gen. Genet.* 202:257-64 (1986).

Tschopp & Cregg, "Heterologous Gene Expression in Methylotrophic Yeast," *Biotechnology* 18:305-22 (1991).

Ullah & Gibson, "Extracellular Phytase (E.C. 3.1.3.8) from *Aspergillus ficuum* NRRL 3135: Purification and Characterization," *Prep. Biochem.* 17(1):63-91 (1987).

Ullah & Sethumadhavan, "Differences in the Active Site Environment of *Aspergillus ficuum* Phytases," *Biochem. Biophys. Res. Commun.* 243:458-62 (1998).

Ullah et al., "Cyclohexanedione Modification of Arginine at the Active Site of *Aspergillus ficuum* Phytase," *Biochem. Biophys. Res. Commun.* 178(1):45-53 (1991).

Ullah, "*Aspergillus ficuum* Phytase: Partial Primary Structure, Substrate Selectivity, and Kinetic Characterization," *Prep. Biochem.* 18(4): 459-71 (1988).

University of Wisconsin, Dept. of Nutritional Sciences: Faculty Mentors in the Interdepartmental Graduate Program in Nutritional Sciences (IGPNS), http://nutrisci.wisc.edu/Facultypages/IGPNSfaculty.html (Nov. 9, 2007) (last visited Feb. 7, 2011).

Van Dijck, "Chymosin and Phytase. Made by Genetic Engineering (No. 10 in a Series of Articles to Promote a Better Understanding of the Use of Genetic Engineering)," *J. Biotech.* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-19 (1991).

Van Hartingsveldt et al., "Cloning, Characterization and Overexpression of the Phytase-Encoding Gene (*phyA*) of *Aspergillus niger*," *Gene* 127:87-94 (1993).

Verwoerd et al., "Stable Accumulation of *Aspergillus niger* Phytase in Transgenic Tobacco Leaves," *Plant Physiol.* 109:1199-205 (1995).

Vohra et al., "Phytic Acid-Metal Complexes," *Proc. Soc. Exp. Biol. Med.* 120:447-49 (1965).

Wodzinski & Ullah, "Phytase," in 42 Advances in Applied Microbiology 263-302 (Saul L. Neidleman & Allen I. Laskin eds., 1996).

Wyss et al., "Biochemical Characterization of Fungal Phytases (*myo*-Inositol Hexakisphosphate Phosphohydrolases): Catalytic Properties," *Appl. Environ. Microbiol.* 65(2):367-73 (1999).

Wyss et al., "Biophysical Characterization of Fungal Phytases (*myo*-Inositol Hexakisphosphate Phosphohydrolases): Molecular Size, Glycosylation Pattern, and Engineering of Proteolytic Resistance," *Appl. Environ. Microbiol.* 65(2):359-66 (1999).

Wyss et al., "Comparison of the Thermostability Properties of Three Acid Phosphatases from Molds: *Aspergillus fumigatus* Phytase, *A. niger* Phytase, and *A. niger* pH 2.5 Acid Phosphatase," Appl. Environ. Microbiol. 64(11):4446-51 (1998).

Yao et al., "Recombinant *Pichia pastoris* Overexpressing Bioactive Phytase," *Sci. China Ser. C.* 41(3):330-36 (1998).

Yi & Kornegay, "Sites of Phytase Activity in the Gastrointestinal Tract of Young Pigs," *Anim. Feed Sci. Tech.* 61:361-68 (1996).

Yi et al., "Effectiveness of Natuphos® Phytase in Improving the Bioavailabilities of Phosphorus and Other Nutrients in Soybean Meal-Based Semipurified Diets for Young Pigs," *J. Anim. Sci.* 74:1601-11 (1996).

Young et al., "Addition of Microbial Phytase to Diets of Young Pigs," *J. Anim. Sci.* 71:2147-50 (1993).

Zale & Klibanov, "On the Role of Reversible Denaturation (Unfolding) in the Irreversible Thermal Inactivation of Enzymes," *Biotech. Bioeng.* XXV:2221-30 (1983).

Zvonok et al., "Construction of Versatile *Escherichia coli*—Yeast Shuttle Vectors for Promoter Testing in *Saccharomyces cerevisiae*," *Gene* 66:313-18 (1988).

\* cited by examiner

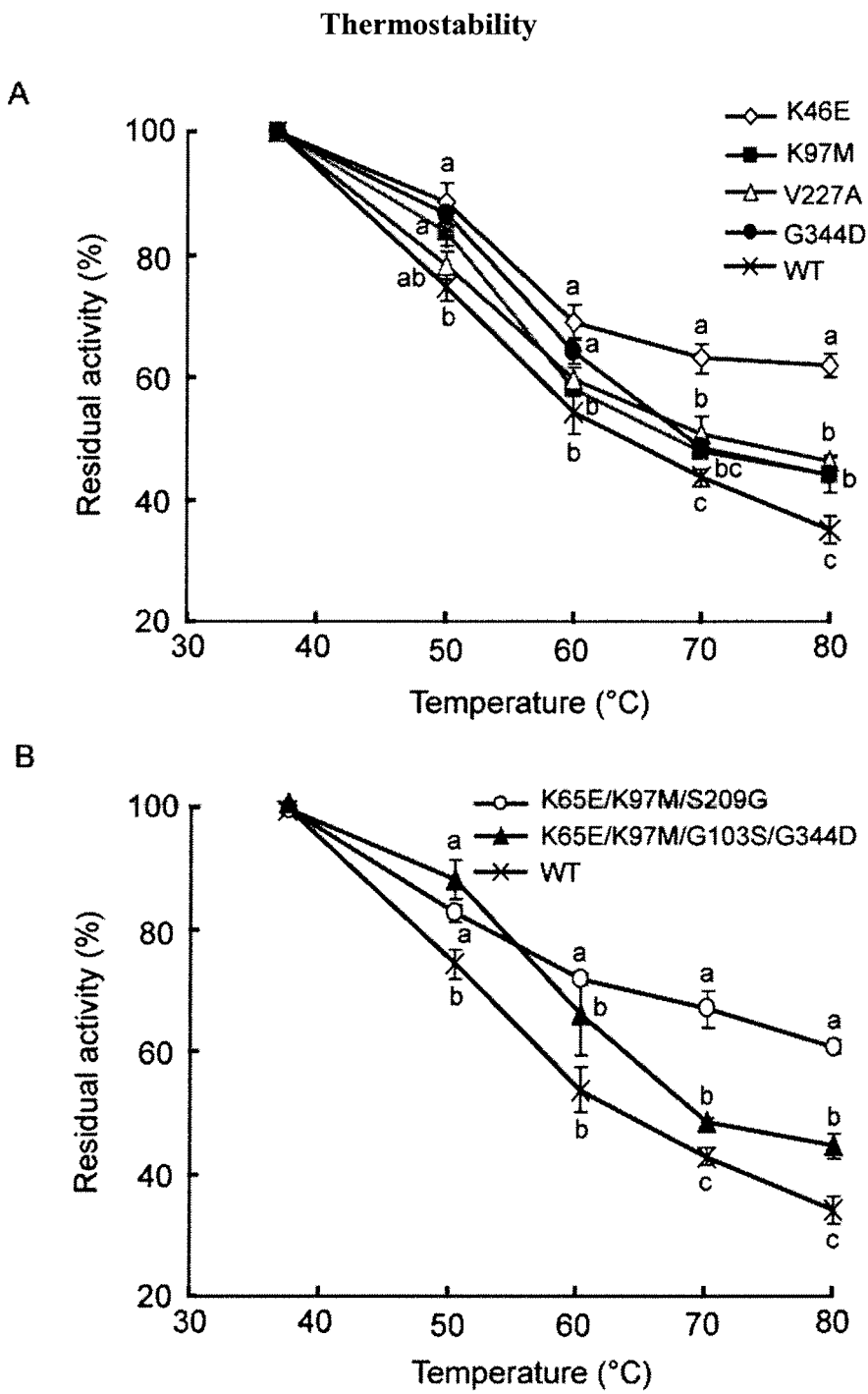
FIG. 2 A-B

C.
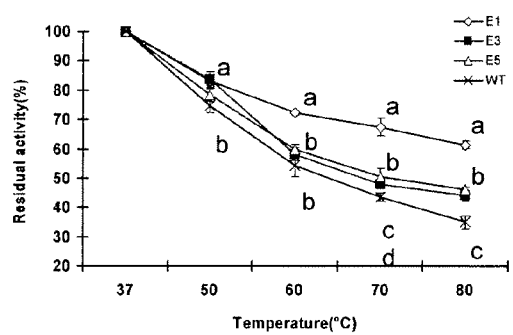
D.
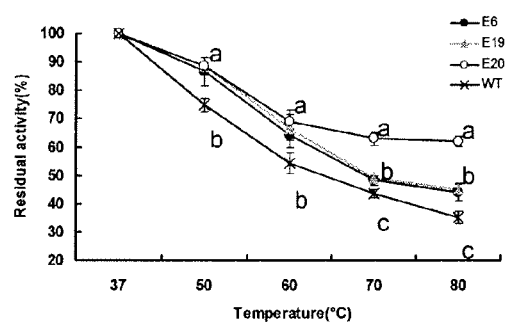
FIG. 2 C-D

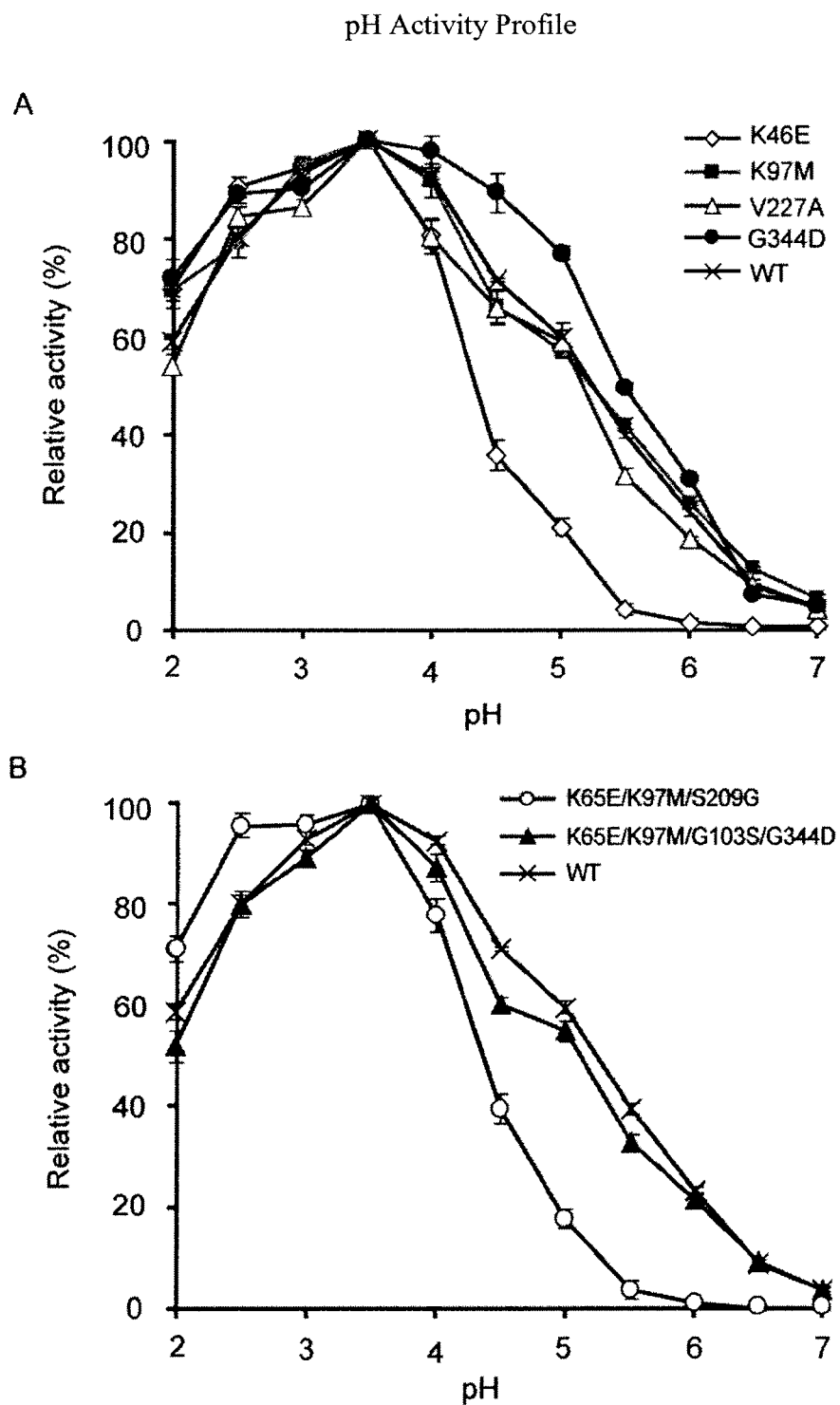
FIG. 3 A-B

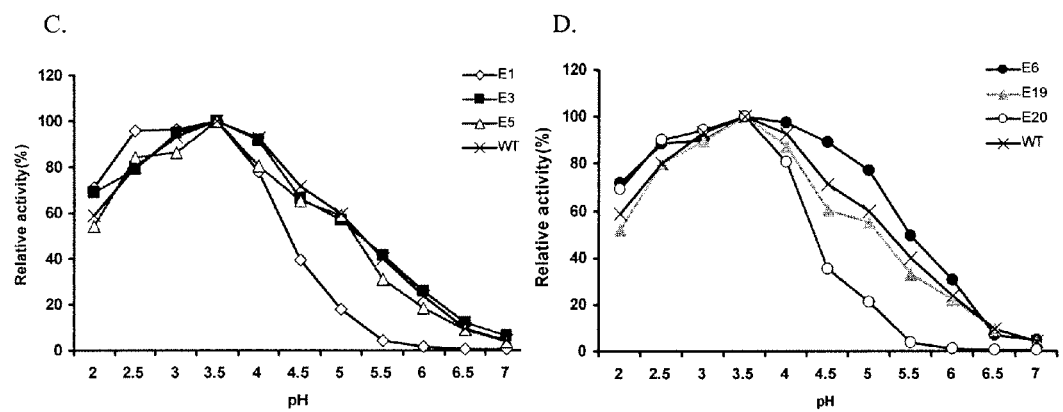
Thermostable mutants, E1 and E20, showed a decreased activity from pH 4.5 to 7.0.
FIG. 3 C-D

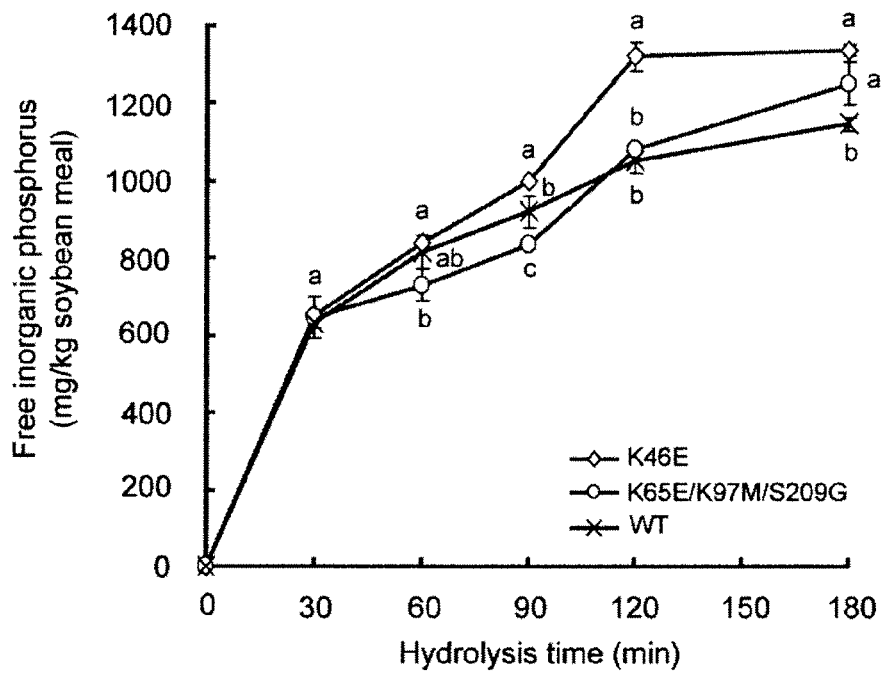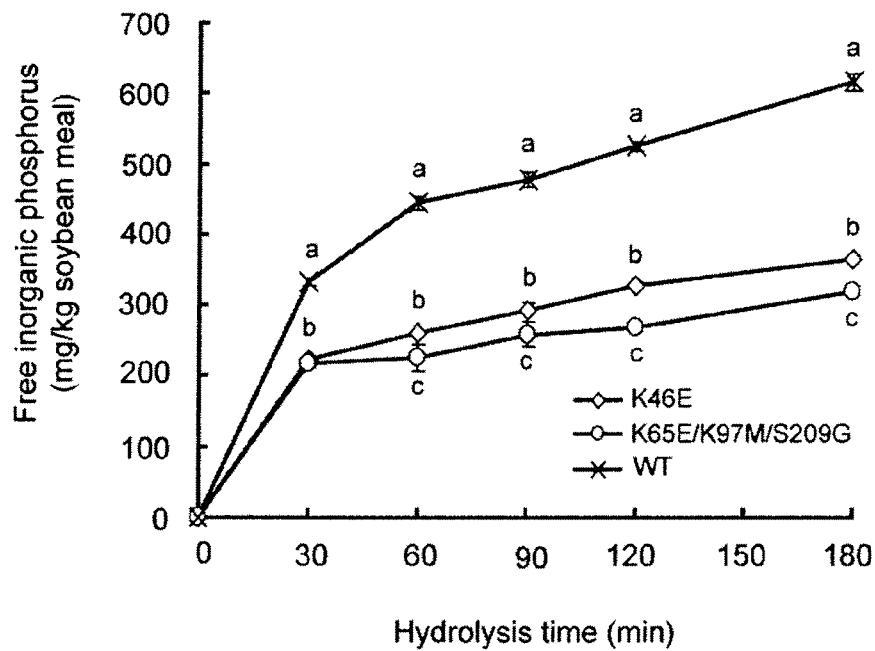
FIG. 4 A-B

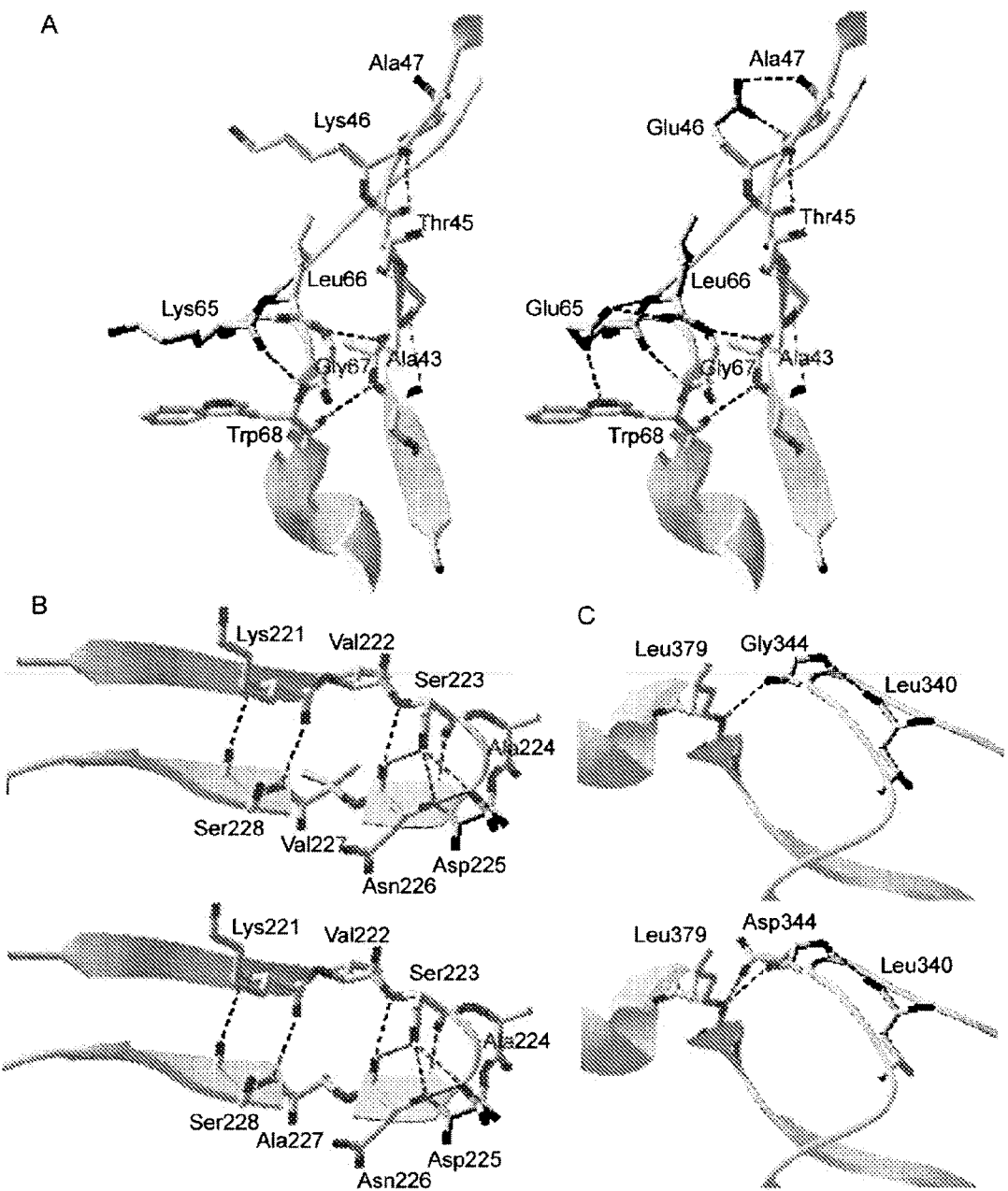
FIG. 6 A-C

D.

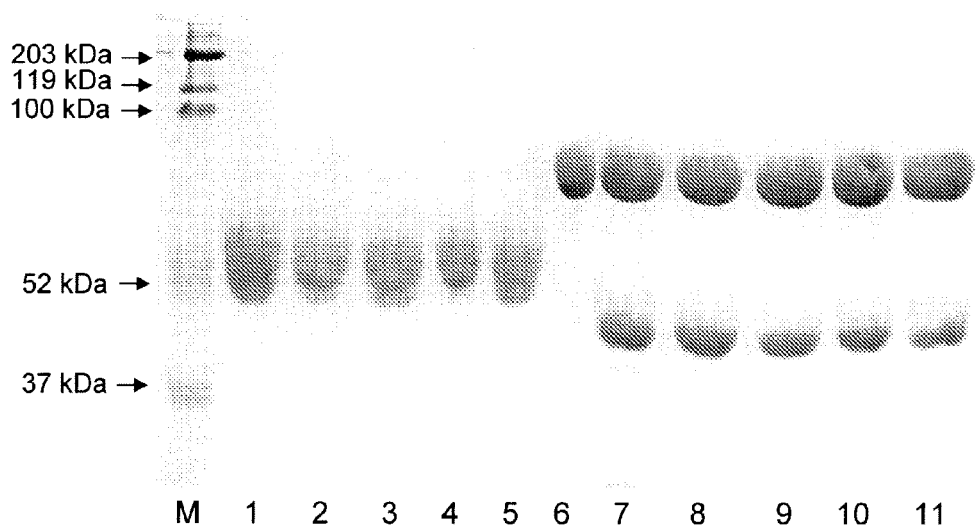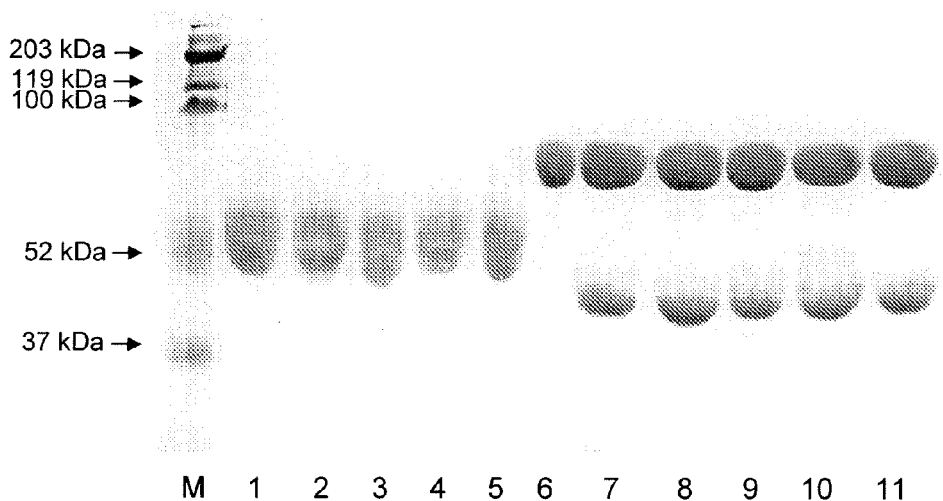
FIG. 8 A-B

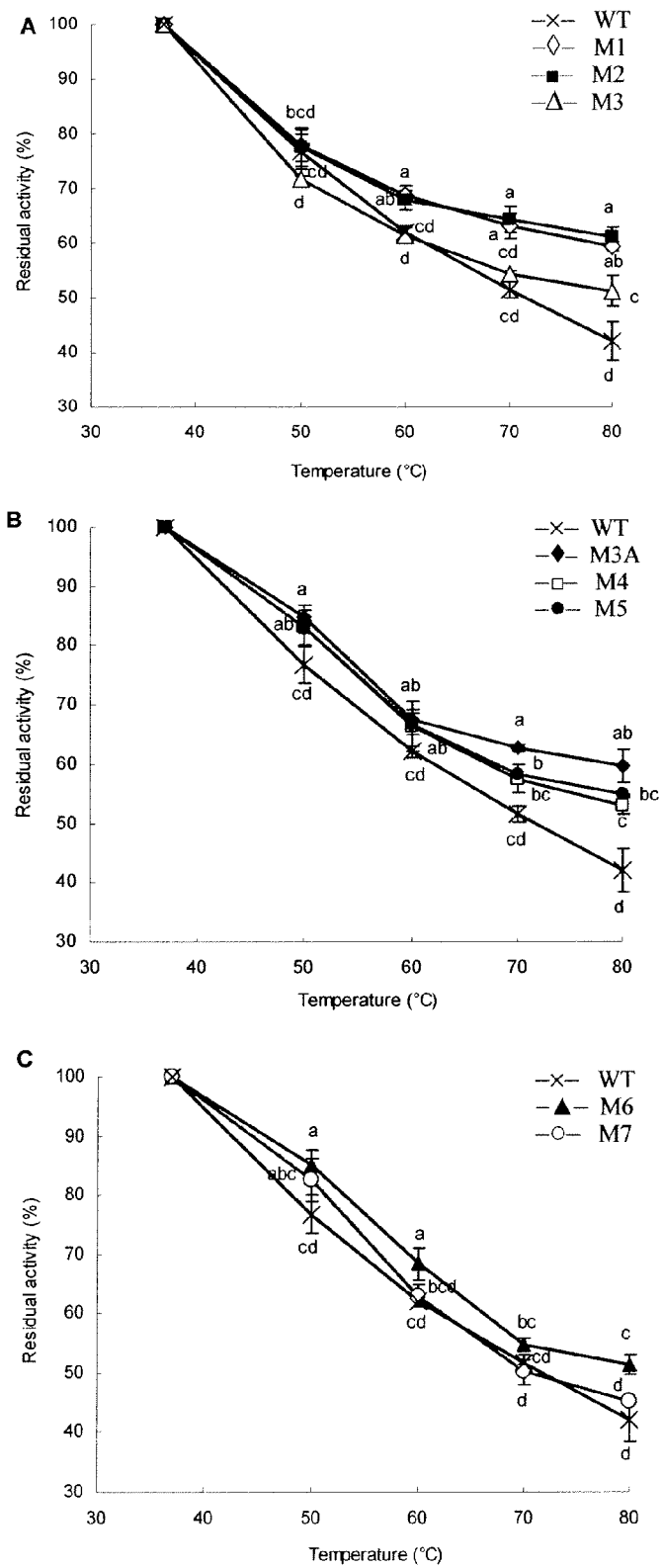
FIG. 9 A-C

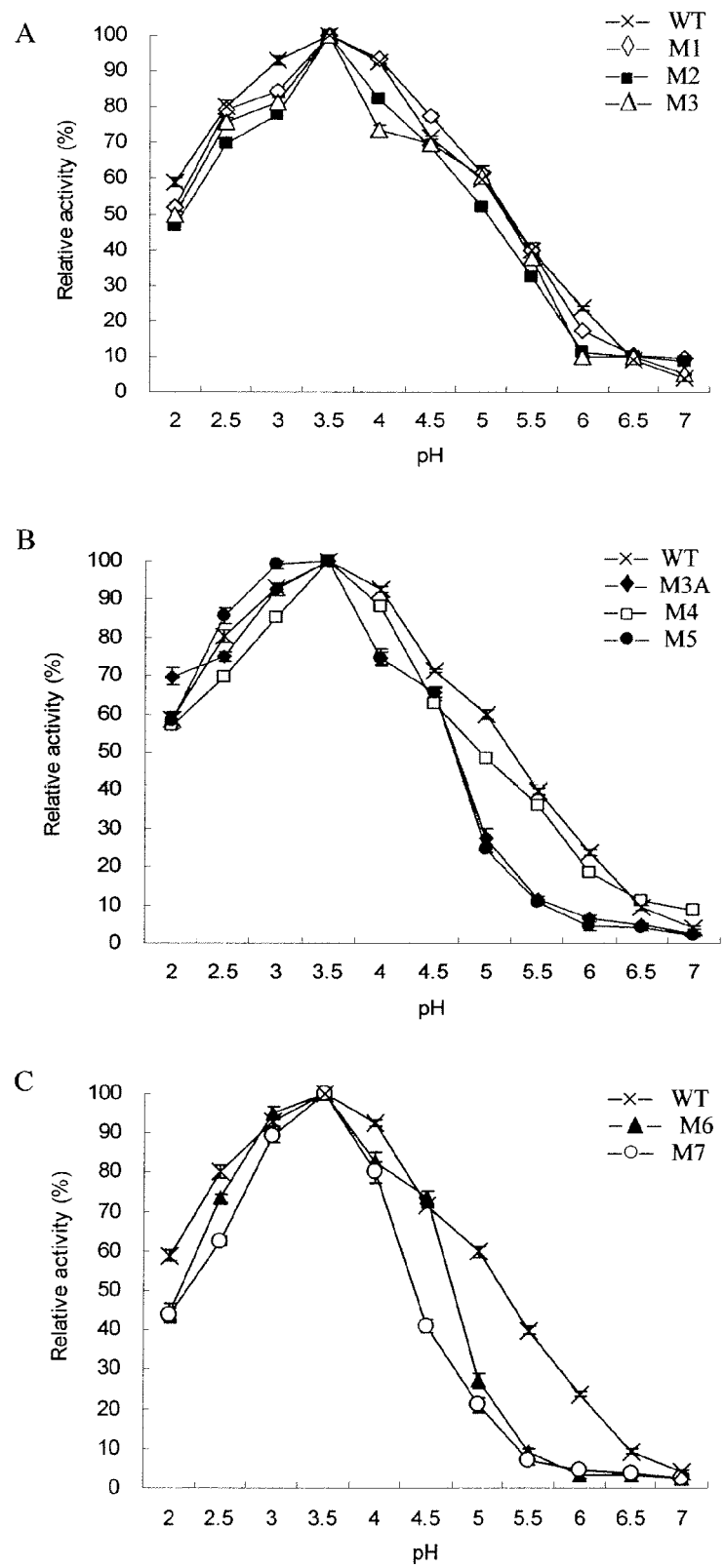
FIG. 10 A-C

PHYTASES WITH IMPROVED THERMAL STABILITY

RELATED APPLICATIONS

This application is a 371 National Stage of International Application No. PCT/US2007/075181 filed on Aug. 3, 2007, which designates the United States, and which claims priority under 35 U.S.C. §119(e) to U.S. provisional patent application No. 60/821,347, filed Aug. 3, 2006, the entirety of which is incorporated herein by reference.

BACKGROUND OF THE INVENTION

As an animal feed supplement, phytase has proved very effective in improving the bioavailability of phytate phosphorus and other minerals as well (Gentile et al., *J. Anim. Sci.* 81:2751-2757 (2003); Lei et al., *J. Nutr.* 123:1117-1123 (1993)) and reducing phosphorus excretion (Han et al., *J. Anim. Sci.* 75:1017-1025 (1997)).

Thermostability is a highly desirable property for phytase to survive high temperature exposure during the feed-pelleting process (Mullaney, *Adv. Appl. Microbiol.* 47:157-199 (2000)).

Phytases (myo-inositol hexakisphosphate phosphohydrolase) catalyze the hydrolysis of phytate into myo-inositol and inorganic phosphate in a stepwise manner, and are added to animal feeds to improve the absorption of phosphorus and to reduce phosphorus excretion. Among many phytases, *Escherichia coli* phytase has a great potential for industrial applications with the advantages of an acidic pH optimum, high specific activity for phytate, and resistance to pepsin digestion (Greiner, R. et al., *Arch. Biochem. Biophys.* 303:107-13 (1993); Lei, X. G., and C. H. Stahl, *Appl. Microbiol. Biotechnol.* 57:474-481 (2001); Rodriguez, E. et al., *Arch. Biochem. Biophys.* 365:262-267 (1999b); Rodriguez, E., et al., *Arch. Biochem. Biophys.* 382:105-112 (2000); Wyss, M., et al., *Appl. Environ. Microbiol.* 65:367-73 (1999)). The second *E. coli* phytase gene, appA2 has 95% sequence homology to appA gene (Rodriguez, E., et al., *Biochem. Biophys. Res. Commun.* 257:117-23 (1999a)). The 1.3 kb appA2 gene encodes a protein of 432 amino acids with 3 putative N-glycosylation sites and its product has a molecular mass of 46.3 kDa after deglycosylation (Rodriguez, E., et al., *Biochem. Biophys. Res. Commun.* 257:117-23 (1999a)). The crystal structure of *E. coli* phytase contains a conserved α/β-domain and a variable α-domain, which is very similar to the overall fold of rat prostatic acid phosphatase, *Aspergillus niger* PhyA phytase, and pH 2.5 acid phosphatase from *A. niger*, despite low sequence homology (Lim, D., et al., *Nat. Struct. Biol.* 7:108-1323 (2000)).

Investigations into the structural basis for the protein stability have illustrated general factors governing the stability of proteins (Kumar, S., et al., *Protein Eng* 13:179-91 (2000); Querol, E., et al., *Protein Eng.* 9:265-71 (1996); Querol, E., et al., *Protein Eng.* 9:265-71 (1996); Vieille, C., and G. J. Zeikus, *Microbiol. Mol. Biol. Rev.* 65:1-43 (2001); Vieille, C., and J. G. Zeikus, *Trends Biotechnol.* 14:183-190 (1996); Yip, K. S., et al., *Structure* 3:1147-58 (1995)). They include increase in hydrogen bonds and ionic interactions, reduction of conformational strain, improvement of the packing of the hydrophobic core and enhanced secondary structure propensity. Based on the proposed thermostabilizations and detailed structural information, a series of attempts to improve the thermostability of proteins have been made using rational design. Rodriguez et al. (2000) added potential glycosylation sites to improve the thermostability of *E. coli* AppA phytase by site-directed mutagenesis. As a semi-rational approach, the consensus concept was applied to phytase to improve thermostability and catalytic efficiency (Lehmann, M., et al., *Protein Eng.* 13:49-57 (2000a); Lehmann, M., et al., *Protein Sci.* 9:1866-72 (2000b)). Structure-based chimeric enzymes were developed as an alternative to directed evolution to improve the thermostability of *A. terreus* phytase (Jermutus, L., et al., *J. Biotechnol.* 85:15-24 (2001)). However, few attempts have been made to improve the thermostability of phytases by directed evolution.

Although a number of successful examples of rational approach have been reported (Georis, J., et al., *Protein Sci.* 9:466-75 (2000); Howell, E. E., et al., *Biochemistry* 29:8561-9 (1990); Kim, T., et al., *Appl. Environ. Microbiol.* 72:4397-4403 (2006); Minagawa, H., et al., *Eur. J. Biochem.* 270:3628-33 (2003); Perl, D., et al., *Nat. Struct. Biol.* 7:380-3 (2000); Williams, J. C., et al., *Protein Eng.* 12:243-50 (1999)), such structure-based rational approach requires not only detailed information on the structures but also the ability to predict the proper site of substitution concerning an optimal amino acid to be substituted (Kim, Y. W., et al., *Appl. Environ. Microbiol.* 69:4866-74 (2003)). Directed evolution has emerged as an effective alternative to rational design of enzyme to engineer enzymes (Kuchner, O., and F. H. Arnold, *Trends Biotechnol.* 15:523-30 (1997); Williams, G. J., and A. Berry, *The Biochemist* 25:13-15 (2003)). It involves generating a vast library of the gene of interest by random mutagenesis such as error-prone PCR or DNA shuffling, followed by screening mutants for desired properties. This approach has been particularly successful in improving the thermostability of proteins. In recent studies, the half-life of subtilisin S41 at 60° C. was increased by 1,200-fold and melting temperature of the mutant increased by 25° C. over the wild-type after eight successive rounds of error-prone PCR and in vitro recombination (Wintrode, P. L., et al., *Biochim. Biophys. Acta* 1549:1-8 (2001)). Cherry et al. (1999) improved the thermostability of a fungal peroxidase by 110-fold by combining mutations from error-prone PCR and in vivo shuffling with those from site-directed mutagenesis (Cherry, J. R., et al., *Nat. Biotechnol.* 17:379-84 (1999)). Giver et al. (1998) reported a thermostable esterase which increased the melting temperature by 14° C. by using error-prone PCR and in vitro recombination.

Increasing the thermostability of phytase is a great benefit because diets for swine and poultry are commonly pelleted at high temperature (60-80° C.). Although naturally thermostable enzymes may be produced by thermophilic organisms, such thermophilic enzymes usually do not function well at the physiological temperature of animals (Vieille, C., and J. G. Zeikus, *Trends Biotechnol.* 14:183-190 (1996)). Alternatively, heat-stable variants may be engineered by rational design and/or directed evolution (Giver, L., et al., *Proc. Natl. Acad. Sci. USA* 95:12809-13 (1998); Pedone, E., et al., *Protein Eng.* 14:255-60 (2001); Spiller, B., et al., *Proc. Natl. Acad. Sci. USA* 96:12305-10 (1999); Sriprapundh, D., et al., *Protein Eng.* 13:259-65 (2000)). Previous studies have investigated the relationship between protein structure and thermal stability (Beadle, B. M., and B. K. Shoichet, *J. Mol. Biol.* 321:285-96 (2002); Georis, J., et al., *Protein Sci.* 9:466-75 (2000); Kumar, S., et al., *Protein Eng.* 13:179-91 (2000); Querol, E., et al., *Protein Eng.* 9:265-71 (1996); Vieille, C., and J. G. Zeikus, *Trends Biotechnol.* 14:183-190 (1996)). The consensus concept was applied to a fungal phytase as a semi-rational approach (Lehmann, M., et al., *Protein Eng.* 13:49-57 (2000a)), and led to the development of the consensus phytase based on 13 fungal phytase sequences that showed an increase in melting temperature ($T_m$) by 15-22° C. while maintaining specific activity for phytate. Later, a new consensus phytase was engineered to improve the catalytic efficiency by replacing amino acid residues in the active site with the corresponding residues of *Aspergillus niger* PhyA phytase (Lehmann, M., et al., *Protein Sci.* 9:1866-72 (2000b)). The unfolding temperature of the new consensus phytase was decreased by 7.6° C. as an expense of the increased catalytic properties. Meanwhile, structure-based chimeric enzymes were designed to improve the thermostability of *A. terreus* phytase (Jermutus, L., et al., *J. Biotechnol.* 85:15-24 (2001)). Based on the crystal structure of *A. niger* phytase, one α-helix of *A. terreus* phytase was replaced by the corresponding stretch of *A. niger* phytase. This replacement improved thermostability without changing enzymatic activity.

SUMMARY OF THE INVENTION

Phytase enzymes are used as a feed supplement to enhance the bioavailability of phosphorus and other nutrient minerals in the feed. The invention provides variant phytase enzyme polypeptides that have increased thermal stability relative to their wild-type counterparts. Among the benefits of increased thermal stability, such variants permit the use of elevated temperatures in the preparation of feed compositions supplemented with such phytase enzymes.

In one aspect, provided herein is an isolated phytase enzyme or an isolated nucleic acid molecule encoding a phytase enzyme, wherein the phytase comprises an amino acid sequence having at least 96 percent sequence identity to SEQ ID NO:1 over a region of at least 100 amino acid residues and containing at least one substitution of at least one amino acid residue selected from the group consisting of residue 46, 65, 97, 103, 112, 144, 209, 227 and 344 of SEQ ID NO:1.

In another aspect, provided herein are methods of increasing the thermostability of a phytase having at least 96 percent sequence identity to SEQ ID NO:1, said method comprising: providing a phytase having at least 96 percent sequence identity to SEQ ID NO:1 over a region of at least 100 amino acid residues and having amino acid residues analgous to amino acid residues K46, K65, K97, D112, D144, S209, V227 and G344 of SEQ ID NO:1; and introducing at least one substitution of at least one amino acid residue selected from the group consisting of residue 46, 65, 97, 112, 144, 209, 227 and 344 of SEQ ID NO:1, wherein the substitution increases the thermostability of the phytase.

In another aspect, provided herein is an isolated *E. coli* phytase polypeptide of SEQ ID NO: 1 carrying a modification of at least one of residues 46, 65, 97, 103, 112, 144, 209, 227 and 344, wherein the phytase has increased thermostability relative to a phytase of SEQ ID NO: 1.

In another aspect, provided herein is an isolated nucleic acid molecule encoding an *E. coli* phytase of SEQ ID NO: 1 carrying a modification of at least one of residues 46, 65, 97, 103, 112, 144, 209, 227 and 344, wherein said phytase has increased thermostability relative to a phytase of SEQ ID NO: 1.

In another aspect, provided herein is an isolated nucleic acid molecule encoding a phytase, wherein said phytase comprises an amino acid sequence having at least 96 percent sequence identity to SEQ ID NO:1 over a region of at least 100 amino acid residues and containing substitutions at least two amino acid residues corresponding to residues selected from the group consisting of residue 46, 65, 103, 112, 144, 209, 227 and 344 of SEQ ID NO:1, which encoded phytase has increased thermostability relative to a phytase of SEQ ID NO: 1.

In another aspect, provided herein is an isolated phytase polypeptide, wherein said phytase polypeptide comprises an amino acid sequence having at least 96 percent sequence identity to SEQ ID NO:1 over a region of at least 100 amino acid residues and containing substitutions at least two amino acid residues corresponding to residues selected from the group consisting of residue 46, 65, 103, 112, 144, 209, 227 and 344 of SEQ ID NO:1, which phytase polypeptide has increased thermostability relative to a phytase of SEQ ID NO: 1.

Also encompassed by the invention are recombinant expression systems and host cells that express the phytase enzymes having increased thermostability, as well as methods of producing such phytase enzymes. Further encompassed are animal feed compositions and foodstuffs comprising such phytase enzymes, and methods of feeding animals comprising feeding such feed or foodstuffs with phytase enzyme to such animals. Further encompassed are methods of improving the nutritional value of a foodstuff consumed by an animal, the method comprising providing a foodstuff comprising myo-inositol hexakisphosphate; providing a phytase enzyme as described herein; and feeding to the animal the foodstuff in combination with the phytase under conditions effective to increase the bioavailability of phosphate from phytate. Further encompassed are methods of in vitro hydrolysis of phytate, the method comprising: providing a phytase as described herein and combining the phytase with a phytate source wherein the phytase increases the bioavailability of phosphate from the phytate source.

Further encompassed by the invention are methods of improving the nutritional value of a foodstuff consumed by humans, the methods comprising: providing a phytase as described herein; and combining the phytase with a foodstuff consumed by humans wherein, upon ingestion, the bioavailability of a mineral from the foodstuff is improved, wherein the mineral is selected from the group consisting of iron, zinc, phosphorus, and calcium.

Further encompassed by the invention are methods of imparting improved mineral nutritional value to a plant that is edible for consumption by animals, the method comprising: providing a transgene comprising an isolated nucleic acid molecule encoding a phytase as described herein, operatively associated with a regulatory sequence containing transcriptional and translational regulatory elements that control expression of the isolated nucleic acid molecule in a transgenic plant cell; providing a non-transformed plant that is edible for consumption by animals; and inserting the transgene into the genome of the non-transformed plant under conditions effective to yield a transformed plant that transgenically expresses a phytase encoded by the isolated nucleic acid molecule, wherein the transformed plant has improved mineral nutritional value compared to that of the non-transformed plant.

BRIEF DESCRIPTION OF THE FIGURES

FIG. 2A-2D shows the results of assays for residual enzyme activity of wild-type AppA2 and PCR mutants after being incubated at varying temperatures (37, 50, 60, 70, and 80° C.) for 10 min. Different letters indicate differences (P<0.05) within each temperature point. All mutants showed improved residual activities after incubation at 80° C., including 25% enhancement in E1 and E20 mutants.

FIG. 3A-3D shows pH activity profiles of wild-type AppA2 and mutants. Phytase activity at pH 3.5 was defined as 100%.

FIG. 4A-4B shows the efficiency of phytate-phosphorus hydrolysis in soybean meal with wild-type AppA2 and substitution mutants K46E (E20) and K65E/K97M/S209G (E1) at enzyme concentration of 500 U per kg soybean meal for different hydrolysis times ranging from 30, 60, 90, 120 to 180 min. Soybean meal was incubated in 0.2 M glycine-HCl buffer, pH 2.0 (A) and pH 3.5 (B). Different letters indicate differences (P<0.05) within each time point.

FIG. 8A-8B shows SDS-PAGE of AppA2 mutants before and after deglycosylation by Endo $H_f$. (A) Lane M: Molecular weight standard; Lane 1-5, WT and mutants before deglycosylation. Lane 1: WT AppA2; Lane 2: M1; Lane 3: M2; Lane 4: M3; Lane 5: M3A; Lane 6: Endo $H_f$. Lane 7-11, WT and mutants after deglycosylation in the same order as Lane 1-5. (B) Lane M: Molecular weight standard; Lane 1-5, WT and mutants before deglycosylation. Lane 1: WT AppA2; Lane 2: M4; Lane 3: M5; Lane 4: M6; Lane 5: M7; Lane 6: Endo $H_f$. Lane 7-11: WT and mutants after deglycosylation in the same order as Lane 1-5.

FIG. 9A-9C shows residual enzyme activity of wild-type AppA2 and AppA2 variants after being incubated at varying temperatures (37, 50, 60, 70, and 80° C.) for 10 min. Different letters indicate differences (P<0.05) within each temperature point.

FIG. 10A-10C shows pH activity profiles of wild-type AppA2 and AppA2 variants. Phytase activity at pH 3.5 was defined as 100%.

DETAILED DESCRIPTION OF THE INVENTION

Figure 1:
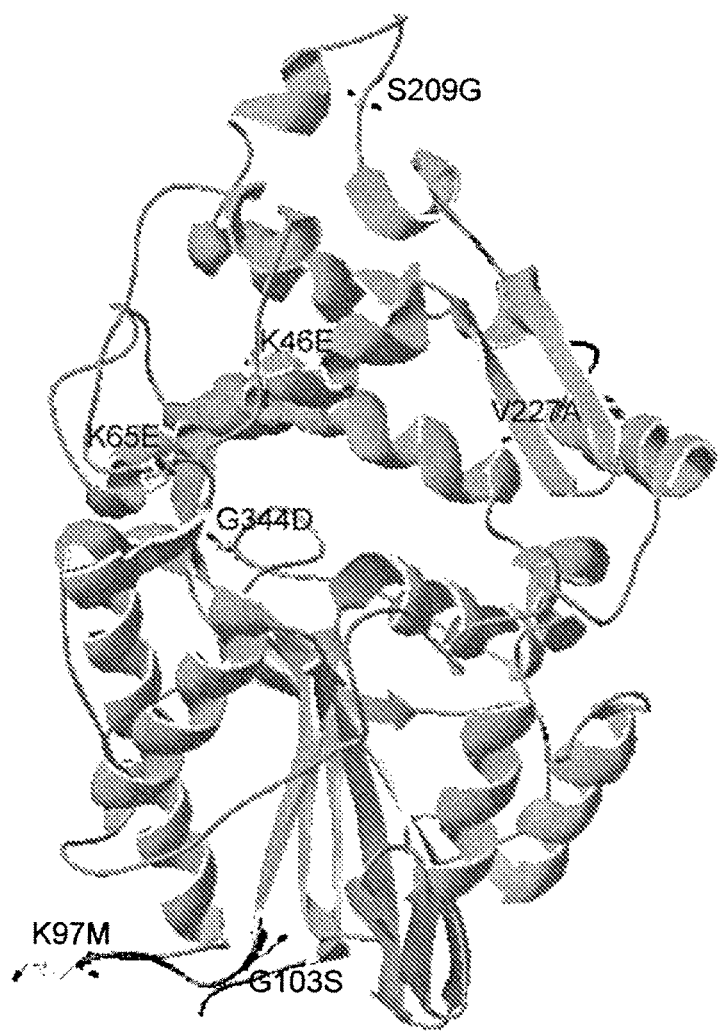
FIG. 1 shows the locations of residue substitutions K46E, K65E, K97M, G103S, S209G, V227A, and G344D in the structure of *E. coli* phytase (Lee, S. et al., *Biotechnol. Lett.* 27: 327-334 (2005)). The ribbon diagram of the three-dimensional structure was prepared using the Swiss-Pdb viewer.

Described herein are variant phytase enzymes with thermal stability enhanced over that of their wild-type counterparts. The enhanced thermal stability permits their incorporation into, for example, animal feed compositions prepared at temperatures that tend to reduce the activity of wild-type phytase enzymes.

The phytase enzymes described herein can be used to supplement animal feed, e.g., to reduce phosphorus excretion and enhance bioavailability of phosphorus and other minerals, e.g., calcium, zinc and iron, which tend to be chelated by dietary phytate, or to provide improved nutrition when administered to humans as a dietary supplement.

In addition to the variant phytases with enhanced thermal stability described herein, the invention relates to nucleic acids encoding such phytases, host cells comprising such nucleic acids, methods of producing recombinant phytase enzymes, compositions, including, but not limited to animal feed and other foodstuff compositions comprising such phytases, and methods of using such phytases. Methods of using the modified phytase enzymes having enhanced thermal stability include, for example, methods of providing improved nutrition to animals and humans, methods of hydrolyzing phytate in vitro, methods of improving the nutritional value of a plant for consumption by animals, and methods of improving the thermal stability of a phytase enzyme. It is important to understand that all phytase variants described herein that have increased thermal stability over wild-type counterparts can be used in any and all of the methods and compositions described herein. These and other aspects are described in the following description and the Examples that follow.

In one aspect, an isolated nucleic acid molecule encoding a phytase is described herein. The phytase of this aspect comprises an amino acid sequence having at least 96 percent sequence identity to SEQ ID NO:1 over a region of at least 100 amino acid residues and contains at least one substitution of at least one amino acid residue selected from the group consisting of residue 46, 65, 97, 103, 112, 144, 209, 227 and 344 of SEQ ID NO:1. Phytases of this aspect and all others described herein have increased thermal stability relative to their wild-type counterparts (in this instance, relative to the phytase of SEQ ID NO: 1).

An alignment of the amino acid (SEQ ID NO:1) and nucleotide sequence (SEQ ID NO:2) of the *E. coli* wild-type AppA2 phytase referenced herein is shown below:

```
  1 atg aaa gcg atc tta atc cca ttt tta tct ctt ttg att ccg tta
  1  M   K   A   I   L   I   P   F   L   S   L   L   I   P   L 46 acc ccg caa tct gca ttc gct cag agt gag ccg gag ctg aag ctg
 16  T   P   Q   S   A   F   A   Q   S   E   P   E   L   K   L 91 gaa agt gtg gtg att gtc agc cgt cat ggt gtg cgt gcc cca acc
 31  E   S   V   V   I   V   S   R   H   G   V   R   A   P   T 136 aag gcc acg caa ctg atg cag gat gtc acc cca gac gca tgg cca
 46  K   A   T   Q   L   M   Q   D   V   T   P   D   A   W   P
```

-continued

```
181 acc tgg ccg gta aaa ctg ggt tgg ctg aca cca cgc ggt ggt gag
 61  T   W   P   V   K   L   G   W   L   T   P   R   G   G   E 226 cta atc gcc tat ctc gga cat tac caa cgc cag cgt ctg gtg gcc
 76  L   I   A   Y   L   G   H   Y   Q   R   Q   R   L   V   A 271 gac gga ttg ctg gcg aaa aag ggc tgc ccg cag cct ggt cag gtc
 91  D   G   L   L   A   K   K   G   C   P   Q   P   G   Q   V 316 gcg att att gct gat gtc gac gag cgt acc cgt aaa aca ggc gaa
106  A   I   I   A   D   V   D   E   R   T   R   K   T   G   E 361 gcc ttc gcc gcc ggg ctg gca cct gac tgt gca ata acc gta cat
121  A   F   A   A   G   L   A   P   D   C   A   I   T   V   H 406 acc cag gca gat acg tcc agt ccc gat ccg tta ttt aat cct cta
136  T   Q   A   D   T   S   S   P   D   P   L   F   N   P   L 451 aaa act ggc gtt tgc caa ctg gat aac gcg aac gtg act gac gcg
151  K   T   G   V   C   Q   L   D   N   A   N   V   T   D   A 496 atc ctc agc agg gca gga ggg tca att gct gac ttt acc ggg cat
166  I   L   S   R   A   G   G   S   I   A   D   F   T   G   H 541 cgg caa acg gcg ttt cgc gaa ctg gaa cgg gtg ctt aat ttt ccg
181  R   Q   T   A   F   R   E   L   E   R   V   L   N   F   P 586 caa tca aac ttg tgc ctt aac cgt gag aaa cag gac gaa agc tgt
196  Q   S   N   L   C   L   N   R   E   K   Q   D   E   S   C 631 tca tta acg cag gca tta cca tcg gaa ctc aag gtg agc gcc gac
211  S   L   T   Q   A   L   P   S   E   L   K   V   S   A   D 676 aat gtt tca tta acc ggt gcg gta agc ctc gca tca atg ctg acg
226  N   V   S   L   T   G   A   V   S   L   A   S   M   L   T 721 gaa ata ttt ctc ctg caa caa gca cag gga atg ccg gag ccg ggg
241  E   I   F   L   L   Q   Q   A   Q   G   M   P   E   P   G 766 tgg gga agg atc act gat tca cac cag tgg aac acc ttg cta agt
256  W   G   R   I   T   D   S   H   Q   W   N   T   L   L   S 811 ttg cat aac gcg caa ttt tat tta cta caa cgc acg cca gag gtt
271  L   H   N   A   Q   F   Y   L   L   Q   R   T   P   E   V 856 gcc cgc agt cgc gcc acc ccg tta ttg gat ttg atc atg gca gcg
286  A   R   S   R   A   T   P   L   L   D   L   I   M   A   A 901 ttg acg ccc cat cca ccg caa aaa cag gcg tat ggt gtg aca tta
301  L   T   P   H   P   P   Q   K   Q   A   Y   G   V   T   L 946 ccc act tca gtg ctg ttt att gcc gga cac gat act aat ctg gca
316  P   T   S   V   L   F   I   A   G   H   D   T   N   L   A 991 aat ctc ggc ggc gca ctg gag ctc aac tgg acg ctt cca ggt cag
331  N   L   G   G   A   L   E   L   N   W   T   L   P   G   Q 1036 ccg gat aac acg ccg cca ggt ggt gaa ctg gtg ttt gaa cgc tgg
346  P   D   N   T   P   P   G   G   E   L   V   F   E   R   W 1081 cgt cgg cta agc gat aac agc cag tgg att cag gtt tcg ctg gtc
361  R   R   L   S   D   N   S   Q   W   I   Q   V   S   L   V 1126 ttc cag act tta cag cag atg cgt gat aaa acg ccg cta tca tta
376  F   Q   T   L   Q   Q   M   R   D   K   T   P   L   S   L 1171 aat acg ccg ccc gga gag gtg aaa ctg acc ctg gca gga tgt gaa
391  N   T   P   P   G   E   V   K   L   T   L   A   G   C   E 1216 gag cga aat gcg cag ggc atg tgt tcg ttg gcc ggt ttt acg caa
406  E   R   N   A   Q   G   M   C   S   L   A   G   F   T   Q 1261 atc gtg aat gaa gca cgc ata ccg gcg tgc agt ttg taa
421  I   V   N   E   A   R   I   P   A   C   S   L   *
```

In one embodiment of this aspect, the at least one substitution is a K46E substitution or a conservative substitution variant thereof. That is, while the glutamic acid substitution for lysine is specifically described, amino acids that are conservative substitutions of glutamic acid can also be advantageous. Now that this and the other sites described herein are identified as locations that provide functional targets for improving thermal stability, further conservative substitutions at those sites can provide additional variants with modified, and/or enhanced, thermal stability relative to the wild-type enzymes.

In another embodiment of this aspect, the substitution is selected from the group consisting of K46E, K65E, K97M, G103S, D112N, D144N, S209G, V227A and G344D or conservative substitutions thereof.

In another embodiment of this aspect, the substitution includes a multiple substitution of K65E/K97M/S209G or conservative substitution variants thereof.

In another embodiment of this and other nucleic acid aspects described herein, a recombinant DNA expression system comprising such nucleic acid molecule is provided. The nucleic acid molecule can be operably linked to a heterologous expression vector, and can be introduced to or contained within a host cell. Host cells can be, for example, bacterial, yeast or other microbial host cells; alternatively, host cells can be derived from higher eukaryotes, e.g., mammals, amphibians or fish, or from, for example, insects, or other non-yeast cells. Methods for introducing nucleic acids to a variety of different host cells and selecting for transformants are well known in the art.

Preferred host cells include yeasts, including, for example, *Saccharomyces, Kluyveromyces, Torulaspora, Schizosaccharomyces, Pichia, Hansenula, Torulupsis, Candida*, and *Karwinskia* species. The yeast can be a methylotrophic strain, e.g., stains of *Pichia, Hansenula, Torulupsis, Candida*, and *Karwinskia*. As noted above, the host cell can be a non-yeast cell. Non-yeast cells of particular interest include, for example, *Aspergillus* species, *Trichoderma* species, and *Neurospora* species.

Host cells carrying a nucleic acid encoding a phytase having increased thermal stability as described herein provide a method of recombinantly producing the phytase variant. Specifically, one can transform a host cell with at least one heterologous nucleic acid molecule of encoding the variant phytase, maintain the transformed host cell under conditions suitable for expression of the phytase, and isolate the phytase enzyme expressed.

In another aspect, described herein are the isolated variant phytase enzymes encoded by the nucleic acids of the first aspect. The isolated phytase can be in pure or non-pure form, but is removed from the cellular context.

In another aspect, described herein is an animal feed composition or a foodstuff comprising an isolated phytase having increased thermal stability as described herein. The feed composition or foodstuff can further comprise additional nutrients or supplements, e.g., a vitamin and mineral mix making up greater than 1% of the composition (e.g., greater than 1%, 2%, 5%, 10%, or more). In preferred embodiments, the feed composition comprises soybean meal. It can further be supplemented, where necessary or desired, with one or more antibiotics. The feed composition or foodstuff can include a range of amounts of the phytase enzyme, e.g., about 100-2,000 units per kilogram of the composition.

In one embodiment of this and other aspects regarding phytase enzymes with increased thermostability, the phytase also has an altered pH profile and an altered pH optima as compared to a corresponding non-substituted phytase. It is preferred that the pH activity profile and/or the optimal pH for the enzyme is/are shifted further to the acidic direction relative to the wild-type enzyme. The improved thermostability provides, for example, the benefit of being able to use higher temperatures in feed preparation, and the lower pH profile or optima provides, for example, better activity in the environment of the gut and thereby better nutritional improvement relative to the wild-type enzyme.

In another aspect, methods are provided herein for feeding a monogastric animal in a manner that provides enhanced nutrition. Such methods involve feeding the animal a foodstuff containing or in combination with a phytase enzyme as described herein that has increased thermal stability relative to a wild-type counterpart. Any of a number of species of animals can benefit, both from improved nutrition (better phosphorus bioavailability and improved bioavailability of minerals that tend to be chelated by phytate, e.g., calcium, zinc and iron) and through reduced phosphorus pollutant excretion. Examples include, but are not limited to fowl species, porcine species, rabbits (*Oryctolagus* species), goats (*Capra* species), sheep (*Ovis* species), cattle (*Bos* species), horses (*Equus* species), and companion animals, e.g., dogs (canine species) and cats (feline species).

In another aspect, methods are provided for improving the nutritional value of a foodstuff consumed by an animal. The methods involve providing a foodstuff comprising myo-inositol hexakisphosphate (phytate), providing a variant phytase enzyme as described herein that has increased thermostability relative to a corresponding wild-type phytase enzyme, and feeding an animal the foodstuff in combination with the phytase. The phytase enzyme increases the bioavailability of phosphate from the phytate in the foodstuff in the gut of the animal. The phytase, by hydrolyzing the phytate in the foodstuff also has the benefit of improving the bioavailability of additional minerals in the foodstuff, including calcium, iron and zinc, that are chelated by phytate. This approach can be advantageous for feeding a variety of species, including, but not limited to those discussed with respect to other aspects described herein, as well as humans. In preferred embodiments, the animal is fed the foodstuff in combination with about 100-2,000 units of the phytase per kilogram of the foodstuff.

In another aspect, phytase enzyme variants described herein can be used for in vitro hydrolysis of phytate. To do so, a phytase enzyme having increased thermostability relative to a corresponding wild-type enzyme is combined with a phytate source under conditions such that the enzyme catalyzes the hydrolysis of the phytate. The reaction thus increases the bioavailability of phosphate from the phytate source, as well as increasing the bioavailability of minerals in the phytate source that are chelated by phytate, including, for example, calcium, iron and zinc. The phytate source can be, for example, an animal feed or other foodstuff.

In another aspect, the variant phytase enzymes described herein can be used to improve the nutritional value of a foodstuff consumed by humans. In this aspect, a variant phytase enzyme as described herein is combined with a foodstuff consumed by humans. Upon ingestion, the bioavailability of one or more minerals (e.g., calcium, iron, zinc) from the foodstuff is improved relative to ingestion of the foodstuff without the phytase enzyme.

In another aspect, provided herein is a method of imparting improved mineral nutritional value to a plant that is edible for consumption by animals. The method involves introducing a transgene directing the expression of a phytase as described herein to a plant that is edible for consumption by animals (non-limiting examples include soybean, alfalfa, wheat, barley, oats, quinoa, etc.). The transgene is operatively associated with regulatory sequences containing transcriptional and translational regulatory elements that control expression of the phytase enzyme from a nucleic acid molecule as described herein in a transgenic plant cell. The resulting transformed plant transgenically expresses a phytase encoded by a nucleic acid molecule as described herein, and the transformed plant has improved mineral nutritional value compared to that of a corresponding non-transformed plant.

In another aspect, described herein are methods of increasing the thermostability of a phytase enzyme. The methods involve introducing one or more, and preferably two or more mutations corresponding to those described herein for *E. coli* AppA2 phytase to a phytase enzyme. In a preferred embodiment, the phytase enzyme has at least 96 percent sequence identity to SEQ ID NO:1 over a region of at least 100 amino acid residues and has amino acid residues analogous or corresponding to amino acid residues K46, K65, K97, G103, D112, D144, S209, V227 and G344 of SEQ ID NO:1. Substitution at one or more of these sites can produce an enzymatically active phytase enzyme variant that has increased thermostability relative to the parent enzyme. In preferred embodiments, the substitution is at an amino acid residue corresponding to K46. A preferred substitution at this site is glutamic acid (E) substitution for the lysine (K). It is contemplated that conservative substitutions of the glutamic acid can also provide a benefit. While not wishing to be bound by theory, it is postulated that the substitution of glutamic acid for lysine provides additional hydrogen bonding opportunities with A47 that provide added stabilization of the structure of the enzyme at elevated temperature. Thus, conservative substitutions of the glutamic acid that also confer the potential for additional hydrogen bonding relative to the lysine in the parental enzyme structure are also specifically contemplated herein. The structure/function details regarding the substitutions that can provide increased thermal stability (e.g., by increased hydrogen bonding opportunities or relief or maintenance of steric constraints) are discussed in further detail in the Examples herein below.

Other embodiments according to this aspect include, for example, multiple substitution at amino acids corresponding to K65, K97 and S209 of SEQ ID NO:1. In preferred embodiments, the substitutions correspond to K65E/K97M/S209G. Other sites for modification to generate a more thermostable enzyme having single or, preferably, multiple substitutions are described in detail in the Examples herein below.

In another aspect, the phytase having increased thermal stability is an *E. coli* phytase variant. According to this aspect, such variants can be encoded by, for example, an isolated nucleic acid molecule encoding a phytase of SEQ ID NO: 1 that carries a modification of at least one of residues K46, K65, K97, G103, D112, D144, S209, V227 and G344 relative to the phytase of SEQ ID NO: 1. The modification can comprise, for example, at least one of K46E, K65E, K97M, G103S, D112N, D144N, K209G, V227A or G344D or conservative substitutions thereof. In a preferred embodiment, the modification is K46E alone. In another embodiment, the modification comprises K46E. In yet another embodiment, the modification is a modification of K65, K97 and S209, including, but not limited to K65E/K97M/S209G.

It should be clear that any of the phytase enzymes described herein can be added to an animal feed composition to provide nutritional benefits to the animal consuming the feed.

In another aspect, the invention provides phytase enzyme variants having increased thermal stability relative to their parent enzyme or nucleic acids encoding them, wherein the phytase comprises an amino acid sequence having at least 96 percent sequence identity to SEQ ID NO:1 over a region of at least 100 amino acid residues and contains substitutions at least two amino acid residues corresponding to residues selected from the group consisting of residues 46, 65, 103, 112, 144, 209, 227 and 344 of SEQ ID NO:1.

In one embodiment of this aspect, the encoded phytase comprises substitutions at residues corresponding to residues 144 and 227 of SEQ ID NO: 1. In a preferred embodiment, the substitutions at residues corresponding to residues 144 and 227 of SEQ ID NO: 1 are D144N and V227A substitutions or conservative substitution variants thereof.

In another embodiment, the encoded phytase of this aspect further comprises a substitution at a residue corresponding to residue 344 of SEQ ID NO: 1. It is preferred that the substitution at a residue corresponding to residue 344 of SEQ ID NO: 1 is G344D or a conservative substitution variant thereof.

In another embodiment, the encoded phytase of this aspect further comprises a substitution at a residue corresponding to residue 65 of SEQ ID NO: 1. It is preferred that the substitution at a residue corresponding to residue 65 of SEQ ID NO: 1 is K65E or a conservative substitution variant thereof.

In another embodiment, the encoded phytase of this aspect further comprises a substitution at a residue corresponding to residue 46 of SEQ ID NO: 1. It is preferred that the substitution at a residue corresponding to residue 46 of SEQ ID NO: 1 is K46E or a conservative substitution variant thereof.

In another embodiment, the encoded phytase of this aspect comprises substitutions at residues corresponding to residues 65, 112, 144, 227 and 344 of SEQ ID NO: 1. It is preferred that the substitutions include K65E, D112N, D144N, V227A and G344D or conservative substitution variants thereof.

In another embodiment, the encoded phytase of this aspect comprises substitutions at residues corresponding to residues 46, 65, 112, 144, 227 and 344 of SEQ ID NO: 1. It is preferred that the substitutions include K46E, K65E, D112N, D144N, V227A and G344D or conservative substitution variants thereof.

In another embodiment, the encoded phytase of this aspect comprises substitutions at residues corresponding to residues 46, 65, 103, 112, 144, 227 and 344 of SEQ ID NO: 1. It is preferred that the substitutions include K46E, K65E, G103S, D112N, D144N, V227A and G344D or conservative substitution variants thereof.

In another embodiment, the encoded phytase of this aspect is a phytase of SEQ ID NO: 1 substituted at amino acid residues 144 and 227. In a preferred embodiment, the substitutions at amino acid residues 144 and 227 are D144N and V227A or conservative substitution variants thereof. In another embodiment, the phytase further comprises a substitution at residue 344 of SEQ ID NO: 1. In a preferred embodiment, the substitution at residue 344 of SEQ ID NO: 1 is G344D or a conservative substitution variant thereof. In another embodiment, the phytase further comprises a substitution at residue 65 of SEQ ID NO: 1. In a preferred embodiment, the substitution at residue 65 of SEQ ID NO: 1 is K65E or a conservative substitution variant thereof. In another embodiment, the phytase further comprises a substitution at residue 46 of SEQ ID NO: 1 In a preferred embodiment, the substitution at residue 46 of SEQ ID NO: 1 is K46E or a conservative substitution variant thereof.

In another embodiment, the encoded phytase of this aspect is a phytase of SEQ ID NO: 1 substituted at amino acid residues 65, 112, 144 and 227. In a preferred embodiment, the substitutions at residues 65, 112, 144 and 227 are K65E, D112N, D144N and V227A or conservative substitution variants thereof. In another embodiment, the phytase further comprises a substitution at residue 46 of SEQ ID NO: 1. In a preferred embodiment, the substitution at residue 46 of SEQ ID NO: 1 is K46E or a conservative substitution variant thereof. In another embodiment, the phytase further comprises a substitution at residue 103 of SEQ ID NO: 1. In a preferred embodiment, the substitution at residue 103 of SEQ ID NO: 1 is G103S or a conservative substitution variant thereof.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited.

As used herein, the term "increased thermostability" or the equivalent terms "enhanced thermal stability" and "improved thermal stability" (the terms are used interchangeably herein) means that a given phytase enzyme retains at least 5% more residual phytate-hydrolyzing activity than a phytase of SEQ ID NO: 1 after incubation at 80° C. for 15 minutes; to avoid doubt, phytase activity is measured using the method described by Han et al., *Appl. Environ. Microbiol.* 65: 1915-1918 (1999), which is incorporated herein by reference.

As well-known in the art, a "conservative substitution" of an amino acid or a "conservative substitution variant" of a polypeptide refers to an amino acid substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine "Positively charged residues" relate to lysine, arginine or histidine. "Negatively charged residues" refer to aspartic acid or glutamic acid. Residues having "bulky side chains" refer to phenylalanine, tryptophan or tyrosine. To avoid doubt as to nomenclature, the term "D144N" or similar terms specifying other specific amino acid substitutions means that the Asp (D) at position 144 is substituted with Asn (N). A "conservative substitution variant" of D144N would substitute a conservative amino acid variant of Asn (N) that is not D.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the table below. A conservative substitution mutant or variant will 1) have only conservative amino acid substitutions relative to the parent sequence, 2) will have at least 90% sequence identity with respect to the parent sequence, preferably at least 95% identity, 96% identity, 97% identity, 98% identity or 99% or greater identity; and 3) will retain phytase activity as that term is defined herein.

| CONSERVATIVE AMINO ACID REPLACEMENTS | | |
|---|---|---|
| For Amino Acid | Code | Replace With |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |

-continued

CONSERVATIVE AMINO ACID REPLACEMENTS

| For Amino Acid | Code | Replace With |
|---|---|---|
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

The term "retains phytase activity" means that a given modified phytase enzyme has at least 80% of the phytase activity of the parent enzyme when tested according to the method described by Piddington et al., Gene 133: 56-62 (1993), which is incorporated herein by reference. It is preferred that a phytase enzyme has at least 90%, at least 100% or more, e.g., at least 110%, 120%, 150%, 2-fold, 3-fold, 5-fold or more of the phytase activity of the parent phytase.

As used herein, the term "increase the bioavailability" of a nutrient or mineral refers to an increase of at least 10% in the amount of a given nutrient or mineral in a feed composition that is absorbed and/or used in the metabolism of an animal fed that composition in conjunction with a phytase enzyme as described herein, relative to the amount of such nutrient or mineral that is absorbed and/or used in the metabolism of an animal not receiving a phytase as a dietary supplement.

As used herein, the term "improved," when used in relation to the nutritional value of a foodstuff, means that one or more nutrients in a foodstuff is/are rendered more bioavailable (i.e., increased bioavailability) upon ingestion of the foodstuff in combination with supplemental phytase enzyme, relative to the bioavailability of the nutrient(s) upon ingestion of the foodstuff without the phytase enzyme.

As used herein, the term "heterologous" means that a given entity is not found in a given cell or species in nature.

As used herein, the term "isolated" means that a given entity is separated from the context in which it occurs in nature. Thus, an "isolated" nucleic acid or polypeptide is separated from a cell, tissue or fluid in which it occurs in nature. In general, an isolated nucleotide sequence, for example, can be any nucleotide sequence that is not part of a genome in a cell, or is separated physically from a cell that normally contains the nucleotide sequence. It should be understood that the term "isolated" is used only in respect to the isolation of the molecule from its natural state, and does not indicate that the molecule is an only constituent of a composition.

As used herein, the term "altered" as applied to pH means that the pH at which a modified phytase enzyme is active (a range of pH for a profile) or optimal (a single value for a pH optima) varies in a statistically significant manner from the pH at which a wild-type phytase is active or optimal. For the avoidance of doubt, such variation is generally at least 0.3 pH units.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a range of "about 0.1 to about 25" should be interpreted to include not only the explicitly recited values of 0.1 and 25, but also include individual values and sub-ranges within the indicated range. Thus, included in this numerical range are individual values such as 2, 5, and 6, and sub-ranges such as from 1 to 3, from 2 to 6, from 8 to 18, from 5 to 20, etc.

This same principle applies to ranges reciting only one numerical value. For example, a range recited as "less than about 5.8" should be interpreted to include individual values and sub-ranges which are within the broadly specified range. Furthermore, such an interpretations should apply regardless of the breadth or type of range or the characteristics being described, such as concentration, amount, etc.

The following provides additional guidance with respect to the practice of the invention described herein.

Phytases:

The principles and guidance set out herein can be applied to produce enhanced thermostability variants of any of a variety of phytase enzymes, and particularly those with significant homology to *E. coli* AppA or AppA2 phytases. Phytase enzymes are well known in the art and described in, for example, U.S. Pat. No. 6,451,572, U.S. Pat. No. 6,511,699, U.S. Pat. No. 6,841,370, and WO No. 97/48812, each of which is incorporated herein by reference.

In addition to *E. coli*, other phytase producing microorganisms comprise bacteria such as *Bacillus subtilis* (Paver et al., *J. Bacteriol.* 151, 1102 (1982), which is hereby incorporated by reference) and *Pseudomonas* (Cosgrove, Austral. *J. Biol. Sci.* 23:1207 (1970), which is hereby incorporated by reference); yeasts, such as *Saccharomyces cerevisiae* (Nayini et al., *Lebensmittel Wissenschaft and Technologie* 17:24 (1984), which is hereby incorporated by reference); and fungi, such as *Aspergillus terreus* (Yamada et al., *Agric. Biol. Chem.* 32:1275 (1986), which is hereby incorporated by reference), and *Aspergillus ficuum* (van Gorcom et al., European Patent Application 89/202,436, which is hereby incorporated by reference).

Two phytases, phyA and phyB, from *Aspergillus niger* NRRL3 135 have been cloned and sequenced (Ehrlich, K. C. et al., "Identification and Cloning of a Second Phytase Gene (phys) from *Aspergillus niger (ficuum),*" *Biochem. Biophys. Res. Commun.*, 195:53-57 (1993); Piddington, C. S. et al., "The Cloning and Sequencing of the Genes Encoding Phytase (phy) and pH 2.5-optimum Acid Phosphatase (aph) from *Aspergillus niger* var. *awamori*," *Gene*, 133:56-62 (1993)). Recently, new phytase genes have been isolated from *Aspergillus terreus* and *Myceliophthora thermophila* (Mitchell et al., "The Phytase Subfamily of Histidine Acid Phosphatases: Isolation of Genes for Two Novel Phytases From the Fungi *Aspergillus terreus* and *Myceliophthora thermophila*," *Microbiology* 143:245-252, (1997)), *Aspergillus fumigatus* (Pasamontes et al., "Gene Cloning, Purification, and Characterization of a Heat-Stable Phytase from the Fungus *Aspergillus fumigatus*" *Appl. Environ. Microbiol.,* 63:1696-1700 (1997)), *Emericella nidulans* and *Talaromyces thermophilus* (Pasamontes et al., "Cloning of the Phytase from *Emericella nidulans* and the Thermophilic Fungus *Talaromyces thermophilus*," *Biochim. Biophys. Acta.,* 1353: 217-223 (1997)), and maize (Maugenest et al., "Cloning and Characterization of a cDNA Encoding a Maize Seedling Phytase," *Biochem. J.* 322:511-517, 1997)).

Various types of phytase enzymes have been isolated and/or purified from *Enterobacter* sp. 4 (Yoon et al., "Isolation and Identification of Phytase-Producing Bacterium, *Enterobacter* sp. 4, and Enzymatic Properties of Phytase Enzyme." *Enzyme and Microbial Technology* 18:449-454 (1996)), *Klebsiella terrigena* (Greiner et al., "Purification and Characterization of a Phytase from *Klebsiella terrigena*." *Arch. Biochem. Biophys.* 341:201-206 (1997)), and *Bacillus* sp. DS11 (Kim et al., "Purification and Properties of a Thermostable Phytase from *Bacillus* sp. DS11," *Enzyme and Microbial Technology* 22:2-7 (1998)). Properties of these enzymes have been studied. In addition, the crystal structure of phy A from *Aspergillus ficuum* has been reported (Kostrewa et al., "Crystal Structure of Phytase from *Aspergillus ficuum* at 2.5 A Resolution," *Nature Structure Biology* 4:185-190 (1997)).

Amino Acid Homology:

The present invention refers to phytases having an amino acid sequence which has a certain degree of identity to SEQ ID NO: 1 (hereinafter "homologous phytases").

For purposes of the present invention the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is –12 for polypeptides and –16 for nucleotides. The penalties for further residues of a gap are –2 for polypeptides, and –4 for nucleotides.

"Align" is part of the FASTA package version v20u6 (see W. R. Pearson and D. J. Lipman, "Improved Tools for Biological Sequence Analysis", *PNAS* 85:2444-2448 (1988), and W. R. Pearson, "Rapid and Sensitive Sequence Comparison with FASTP and FASTA," *Methods in Enzymology* 183:63-98 (1990)). FASTA protein alignments use the Smith-Waterman algorithm with no limitation on gap size (see "Smith-Waterman algorithm", T. F. Smith and M. S. Waterman, *J. Mol. Biol.* 147:195-197 (1981)).

Identifying Corresponding Position Numbers:

In order to determine a "corresponding" position in another parent phytase, the amino acid sequence of the other phytase is aligned with SEQ ID NO: 1 as specified above in the section entitled Amino Acid Homology. From this alignment, the position in another phytase which corresponds to a given position of SEQ ID NO: 1 can be determined. The other phytase can be a mature phytase, or it may also include a signal peptide, or it can be a fragment of the mature phytase which has phytase activity.

Vectors and Host Cells:

The phytase enzyme can be expressed in any prokaryotic or eukaryotic expression system. A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Preferred hosts for expressing phosphatase include fungal cells, including species of yeast or filamentous fungi, may be used as host cells in accordance with the present invention. Preferred yeast host cells include different strains of *Saccharomyces cerevisiae* and *Schizosaccharomyces*. Other yeasts like *Kluyveromyces* and *Torulaspora* can also be used. In a preferred embodiment, the yeast strain used to overexpress the protein is *Saccharomyces cerevisiae*. Filamentous fungi host cells include *Aspergillus* and *Neurospora*.

In another embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia, Hansenula, Torulopsis, Candida,* and *Karwinskia*. These yeast genera can use methanol as a sole carbon source. In a preferred embodiment, the methylotrophic yeast strain is *Pichia pastoris*.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also provides a yeast strain having a heterologous gene which encodes a protein or polypeptide with phytase activity. The heterologous gene should be functionally linked to a promoter capable of expressing phytase in yeast and followed by a transcriptional terminator.

Yet another aspect of the invention is a vector for expressing phytase in a host. The vector carries a phosphatase gene which encodes a protein or polypeptide with phytase activity.

For cloning into yeast, the gene can be cloned into any vector which replicates autonomously or integrates into the genome of yeast. The copy number of autonomously replicating plasmids, e.g. YEp plasmids may be high, but their mitotic stability may be insufficient (Bitter et al., *Meth. Enzymol.* 153: 516-544 (1987)). They may contain the 2 mu-plasmid sequence responsible for autonomous replication, and an *E. coli* sequence responsible for replication in *E. coli*. The vectors preferably contain a genetic marker for selection of yeast transformants, and an antibiotic resistance gene for selection in *E. coli*. The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (Struhl et al., *Proc. Natl. Acad. Sci. U.S.A.* 76: 1035-1039 (1979), Powels et al., *Cloning Vectors*, I-IV, et seq. (1985), Elsevier, and Sakai et al., *Biotechnology* 9: 1382-1385 (1991)). Some vectors have an origin of replication, which functions in the selected host cell. Suitable origins of replication include 2μ, ARS1, and 25 μM. The vectors have restriction endonuclease sites for insertion of the fusion gene and promoter sequences, and selection markers. The vectors may be modified by removal or addition of restriction sites, or removal of other unwanted nucleotides.

The phytase gene can be placed under the control of any promoter (Stetler et al., *Biotecnology* 7: 55-60 (1989)). One can choose a constitutive or regulated yeast promoter. Suitable promoter sequences for yeast vectors include, among others, promoters for metallothionein, 3-phosphoglycerate kinase (Hitzeman et al., *J. Biol. Chem.* 255: 2073 (1980)) or other glycolytic enzymes (Hess et al., *J. Adv. Enzyme Reg.* 7: 149 (1968)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in EP A-73,657 to Hitzeman, which is hereby incorporated by reference. Another alternative is the glucose-repressible ADH2 promoter (Russell et al., *J. Biol. Chem.* 258: 2674 (1982), Beier et al., *Nature* 300: 724 (1982)), which are hereby incorporated by reference.

One can choose a constitutive or regulated yeast promoter. The strong promoters of e.g., phosphoglycerate kinase (PGK) gene, other genes encoding glycolytic enzymes, and the alpha-factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP150 terminator, or any other functional terminator is used. Here, promoters and terminators are called control elements. The present invention is not restricted to any specific vector, promoter, or terminator.

The vector can also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, or antibiotic resistance genes.

The vector can also have an origin of replication capable of replication in a bacterial cell. Manipulation of vectors is more efficient in bacterial strains. Preferred bacterial origin of replications are ColE1, Ori, or oriT.

A leader sequence either from the yeast or from phytase genes or other sources can be used to support the secretion of expressed phytase enzyme into the medium. The present invention is not restricted to any specific type of leader sequence or signal peptide.

Suitable leader sequences include the yeast alpha factor leader sequence, which may be employed to direct secretion of the phytase. The alpha factor leader sequence is often inserted between the promoter sequence and the structural gene sequence (U.S. Pat. No. 4,546,082; and European published patent application No. 324,274, which are hereby incorporated by reference). Another suitable leader sequence is the *S. cerevisiae* MF alpha 1 (alpha-factor) is synthesized as a prepro form of 165 amino acids comprising signal- or prepeptide of 19 amino acids followed by a "leader" or propeptide of 64 amino acids, encompassing three N-linked glycosylation sites followed by (LysArg(Asp/Glu, Ala)2-3 alpha-factor)4 (Kurjan et al., *Cell* 30: 933-943 (1982)). The signal-leader part of the preproMF alpha 1 has been widely employed to obtain synthesis and secretion of heterologous proteins in *S. cerivisiae*. Use of signal/leader peptides homologous to yeast is known from. U.S. Pat. No. 4,546,082, European Patent Applications Nos. 116,201; 123,294; 123, 544; 163,529; and 123,289 and DK Patent Application No. 3614/83, which are hereby incorporated by reference. In European Patent Application No. 123,289, which is hereby incorporated by reference, utilization of the *S. cerevisiae* a-factor precursor is described whereas WO 84/01153, which is hereby incorporated by reference, indicates utilization of the *Saccharomyces cerevisiae* invertase signal peptide, and German Patent Application DK 3614/83, which is hereby incorporated by reference, indicates utilization of the Saccha- lomyces *cerevisiae* PH05 signal peptide for secretion of foreign proteins.

The alpha-factor signal-leader from *Saccharomyces cerevisiae* (MF alpha 1 or MF alpha 2) may also be utilized in the secretion process of expressed heterologous proteins in yeast (U.S. Pat. No. 4,546,082, European Patent Applications Nos. 16,201; 123,294; 123 544; and 163,529, which are hereby incorporated by reference). By fusing a DNA sequence encoding the *S. cerevisiea* MF alpha 1 signal/leader sequence at the 5' end of the gene for the desired protein secretion and processing of the desired protein was demonstrated. The use of the mouse salivary amylase signal peptide (or a mutant thereof) to provide secretion of heterologous proteins expressed in yeast has been described in Published PCT Applications Nos. WO 89/02463 and WO 90/10075, which are hereby incorporated by reference.

U.S. Pat. No. 5,726,038 describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described in Hinnen et al. (Hinnen et al., *Proc. Natl. Acad. Sci. U.S.A.* 75: 1929 (1978)). The Hinnen et al. protocol selects for Trp transformants in a selective medium, wherein the selective medium consists of 0.67% yeast nitrogen base, 0.5% casamino acids, 2% glucose, 10·mu·g/ml adenine and 20·mu·g/ml uracil.

The gene can be maintained on stable expression vector, an artificial chromosome, or by integration into the yeast host cell chromosome. Integration into the chromosome may be accomplished by cloning the phytase gene into a vector which will recombine into a yeast chromosome. Suitable vectors may include nucleotide sequences which are homologous to nucleotide sequences in the yeast chromosome. Alternatively, the phytase gene may be located between recombination sites, such as transposable elements, which can mobilize the gene into the chromosome.

Transgenic Plants:

In certain embodiments of the invention described herein transgenic plants are generated. The generation of transgenic plants is well known in the art. A common approach to plant transgenesis involves the use of *Agrobacterium* species. The use of *agrobacterium* mediated transfer has proven a valuable technique in the production of genetically modified plant species. In addition to their utility in the transformation of plant species, *Agrobacterium* are readily manipulated in vitro by well established techniques of molecular biology. Such techniques are well known to those skilled in the art, and are referenced in e.g., Ausubel, Sambrook, and Berger, supra; Croy (ed) (1993) Plant Molecular Biology, Bios Scientific Publishers, Oxford, U.K., and Jones (ed) (1995) Plant Gene Transfer and Expression Protocols—Methods in Molecular Biology, Volume 49 Humana Press, Towata, N.J. These are useful in the context of the present invention for the manipulation and culture of *Agrobacterium* cells, transformation techniques, and techniques useful for the analysis of plant cells subject to *Agrobacterium* mediated transformation.

While dicotyledonous plants have proven most amenable to manipulation by *Agrobacterium* mediated transformation, reports of transformation of important monocotyledonous crop plants have been forthcoming. In addition, *Agrobacterium* strains which are capable of transforming fungal species have also been described. *Agrobacterium* Vir proteins have been used to target DNA to the nucleus of mammalian cells as well. The present invention makes use of this valuable technique to produce transgenic plants which have integrated an exogenous DNA sequence into their genome. *Agrobacterium*-mediated gene transfer to plants and the regeneration of whole plants from transformed plant cell cultures are described in, e.g., U.S. Pat. No. 6,686,515, which is incorporated herein by reference. In addition to the *Agrobacterium*-mediated plant transformation approach, other methods include, for example biolistic gene transfer (the so-called "gene gun") and electroporation of cultured plant cells. Such methods are described in, e.g., U.S. Pat. No. 6,800,794; Ream, *Ann. Rev. Phytophat.*, 27, 583-618 (1989); Negretiu & Gharti-Chhetri, A Laboratory Guide for Cellular and Molecular Biology, *BIOMETHODS* (1991); Casse-Delbart, La transgenese Vegetale. Les Plantes Transgeniques en Agriculture (Plant Transgenesis. Transgenic plants in agriculture), J. Librey Eurotext, ISBN: 27420-0149-2, 59-88 (1996); and Stanford, *Physiol. Plant.* 79, 20614 209 (1990)) each of which is incorporated herein by reference.

Feed Compositions and Pelleting:

Any of a variety of different animal feed compositions can be modified to include a phytase enzyme as described herein. Frequently where enzymes have been added to animal feed compositions, the enzymes must be added after feed pelleting, e.g., by spraying liquid enzyme preparations onto the pelletized feed. This approach presents problems with respect to the uniformity of application, among others. Because the phytase enzyme variants described herein have increased thermostability, the processes for preparation of feed compositions can involve the addition of phytase enzyme preparations (in liquid or, alternatively, powdered form) to the feed composition prior to pelleting processes that involve the use of heat. Of course, if the feed composition is not a pelletized composition, the same can also apply—the phytase variant can be added as a liquid or dried preparation during the preparation of the feed composition.

Feed compositions can be prepared according to methods known in the art, e.g. by mixing the phytase variant with the additional ingredients, if any.

Animal feed compositions or diets have a relatively high content of protein. An animal feed composition generally has a crude protein content of 50-800, or 75-700, or 100-600, or 110-500, or 120-490 g/kg, and will furthermore comprises a phytase enzyme variant as described herein.

Furthermore, or in the alternative (to the crude protein content indicated above), the animal feed compositions as described herein can have a content of metabolizable energy of, for example, 10-30, or 11-28, or 11-26, or 12-25 MJ/kg; and/or a content of calcium of 0.1-200, or 0.5-150, or 1-100, 4-50 g/kg; and/or a content of available phosphorus of 0.1-200, or 0.5-150, or 1-100, or 1-50, or 1-25 g/kg; and/or a content of methionine of 0.1-100, or 0.5-75, or 1-50, or 1-30 g/kg; and/or a content of methionine plus cysteine of 0.1-150, or 0.5-125, or 1-80 g/kg; and/or a content of lysine of 0.5-50, or 0.5-40, or 1-30 g/kg.

Where necessary or desired, crude protein is calculated as nitrogen (N) multiplied by a factor 6.25, i.e. Crude protein (g/kg)=N (g/kg)×6.25, as stated in Animal Nutrition, $4^{th}$ edition, Chapter 13 (Eds. P. McDonald, R. A. Edwards and J. F. D. Greenhalgh, Longman Scientific and Technical, 1988, ISBN 0-582-40903-9). The nitrogen content can be determined by the Kjeldahl method (A.O.A.C., Official Methods of Analysis 14.sup.th ed., Association of Official Analytical Chemists, Washington D.C. (1984)). But also other methods can be used, such as the so-called Dumas method in which the sample is combusted in oxygen and the amount of nitrous gasses formed are analysed and recalculated as nitrogen.

Metabolizable energy can be calculated on the basis of the NRC publication Nutrient Requirements of Swine (1988) pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

Animal feed compositions as described herein generally contain at least one vegetable protein or protein source. Examples of vegetable proteins or protein sources are soybean, peas and rape seed from leguminosae and brassica families, and the cereals such as barley, maize (corn), oat, rice, rye, sorghum and wheat. Examples of feed compositions comprise 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey. In preferred embodiments, the compositions comprise soybean meal.

As noted above, animal diets can e.g. be manufactured as mash feed (non-pelleted) or pelleted feed. Typically, the milled feed-stuffs are mixed and sufficient amounts of essential vitamins and minerals are added according to the specifications for the species in question.

The phytase variant of the invention can be added in the form of a solid or liquid enzyme formulation, or in the form of a feed additive, such as a pre-mix. A solid composition is typically added before or during the mixing step; and a liquid composition is typically added after the pelleting step.

The phytase variant of the invention when added to animal feed leads to an improved nutritional value of the feed, e.g. the growth rate and/or the weight gain and/or the feed conversion (i.e. the weight of ingested feed relative to weight gain) of the animal is/are improved. These results may be due to, in turn, one or more of the following effects: The phosphate moieties of phytic acid chelates divalent and trivalent cations such as metal ions, i.e., the nutritionally essential ions of calcium, iron, zinc and magnesium as well as the trace minerals manganese, copper and molybdenum. Besides, the phytic acid also to a certain extent binds proteins by electrostatic interaction. At a pH below the isoelectric point, pI, of the protein, the positively charged protein binds directly with phytate. At a pH above pI, the negatively charged protein binds via metal ions to phytate. Phytic acid and its salts, phytates, are often not metabolized, since they are not absorbable from the gut, i.e. neither the phosphorous thereof, nor the chelated metal ions, nor the bound proteins are nutritionally available. Accordingly, since phosphorus is an essential element for the growth of all organisms, food and feed preparations need to be supplemented with inorganic phosphate. Quite often also the nutritionally essential ions such as iron and calcium, must be supplemented. And, besides, the nutritional value of a given diet decreases, because of the binding of proteins by phytic acid. Thus, the action of phytase can assist in overcoming the need to supplement feed with inorganic phosphate, iron, calcium, and other essential minerals.

The following Examples further illustrate the invention, but should not be construed to limit the scope of the invention in any way. Detailed descriptions of conventional methods, such as those employed in the construction of vectors and plasmids, can be obtained from numerous publications, including Sambrook, J et al., *Molecular Cloning*: A Laboratory Manual, $2^{nd}$ ed., Cold Spring Harbor Laboratory Press (1989); Coligan, J. et al., *Current Protocols in Immunology*, Wiley & Sons, Incorporated (1994); Enna, S. J. et al., *Current Protocols in Pharmacology*, Wiley & Sons (1991); Bonifacino, J. S. et al., *Current Protocols in Cell Biology*, Wiley & Sons (1999). All references mentioned herein are incorporated in their entirety.

EXAMPLES

Example 1

Enhanced Thermostability of *E. coli* AppA2 Phytase by Error-Prone PCR

Directed evolution was employed to generate thermostable *E. coli* AppA2 variants. The selected variants were then purified and characterized for biochemical and biophysical properties.

A. Strains and Plasmids.

Plasmid pYAα2 contains the coding region of the wild-type appA2 gene and the α factor signal peptide in pYES2 vector (Invitrogen, San Diego, Calif.) (Lee, S., et al., *Biotechnol. Lett.* 27:327-334 (2005)). This plasmid was used to express the appA2 gene in *Saccharomyces cerevisiae* INVSc1 [His-, Leu-, Trp-, Ura-]. A mutant library was expressed in *S. cerevisiae* and screened for improved thermostability. After selection of improved mutants, selected mutants were expressed in high activity in *Pichia pastoris* X33 for further protein purification and characterization. To express the appA2 gene in *P. pastoris* X33, plasmid pGAα2 was used, which contains the appA2 gene cloned into a constitutive expression vector pGAPZαA (Invitrogen, San Diego, Calif.) (Lee, S., et al., *Biotechnol. Lett.* 27:327-334 (2005)). *E. coli* JM 109 strain was used for yeast DNA transformation into *E. coli*.

B. Error-Prone PCR and Mutant Library Construction.

Random mutagenesis of the appA2 gene was carried out by error-prone PCR (Caldwell, R. C., and G. F. Joyce, *PCR Methods Appl.* 2:28-33 (1992)). Error-prone PCR was performed using pYAa as a template in a 100 µl reaction mixture containing 10 mM Tris-HCl (pH 8.3), 50 mM KCl, 7 mM $MgCl_2$, 0.2 mM dATP and dGTP, 0.6 to 1 mM dCTP and dTTP, 10 ng of template, 0.1 to 0.3 mM $MnCl_2$, and 5 U of Taq polymerase (Fisher). Two oligonucleotides flanked by EcoRI and XbaI restriction sites were used as forward primer E2 (SEQ ID NO:3) (5'-GGA ATT CCA GAG TGA GCC GGA-3') and reverse X2 (SEQ ID NO:4) (5'-GGT CTA GAT TAC AAA CTG CAC G-3'). Thermal cycling parameters were 95° C. for 3 min (1 cycle), 94° C. for 1 min, 55° C. for 1 min, 72° C. for 2 min (30 cycles), and 72° C. for 10 min (1 cycle). The PCR products were gel-purified using a Quiagen kit (Quiagen, Valencia, Calif.) and digested with restriction enzymes EcoRI and XbaI. The digested PCR products were ligated into linearized pYES2 vextor digested with the same enzymes. The ligation mixture was transformed into competent *S. cerevisiae* INVSc1 cells using electroporation (1.5 kV, 129Ω, 4.9 ms, ECM 600 Electro Cell Manipulatorm Genetronics, BTX Instrument Division, San Diego, Calif.) and then plated onto SC (Ura-) minimal medium containing 2% glucose for the selection of positive transformants.

C. Screening for Improved Thermostability.

Thermostability was determined by the residual phytase activity after incubation of the enzyme at 80° C. for 15 min. After incubation of the SC (Ura-) plates at 30° C. for 3 days, single colonies of transformants were transferred into 96-well plates containing 20 µl of SC (Ura-) minimal medium per well. The 96-well plates were incubated at 30° C., 220 rpm for 24 h. After 24 h, 100 µl of YPG expression medium (1% yeast extract, 2% peptone, and 2% galactose) was added to each well and the plates were incubated at 30° C., 220 rpm for 36 h. Enzymes from culture supernatants were diluted in 0.2 M glycine-HCl, pH 3.5 and transferred to new 96-well plates. Two replica plates for each growth plate were prepared. One replica plate was incubated at 85° C. for 15 min and chilled on ice for 15 min. Both of the plates were assayed for phytase activity as previously described (Han, Y. M., et al., *Appl. Environ. Microbiol.* 65:1915-1918 (1999)) with modification to be suitable for a 96-well plate. The hydrolysis reaction mixture was transferred to a new 96-well plate and diluted with $H_2O$ by 10-fold, followed by the color development reaction at 50° C. for 20 min (Han, Y. M., et al., *Appl. Environ. Microbiol.* 65:1915-1918 (1999)). After the incubation, free inorganic phosphorus was measured at 820 nm by a 96-well plate reader after cooling down at room temperature. One phytase unit is defined as the amount of activity that releases 1 µmol of inorganic phosphorus from sodium phytate per min at 37° C.

After screening for improved thermostability, plasmids of selected mutants were isolated using the yeast plasmid miniprep kit (Zymo Research, CA) and transformed into competent *E. coli* JM109 cells. After extraction from *E. coli* cells, plasmids were verified by automated DNA sequencing.

Following error-prone PCR mutagenesis of AppA2, approximately 5,000 clones were screened for increased thermostability. At the initial screening, a mutant library was incubated in a 96-well plate at 85° C. for 15 min. Mutants showing a 20% higher residual activity than the wild-type enzyme were selected. Six best mutants were selected for improved thermostability. Sequence analysis of the selected mutants showed that the number of amino acid substitutions varied from 1 to 4 per mutant (Table 1). These mutants include four single mutants (K46E, K97M, V227A, and G344D) and two multiple mutants (K65E/K97M/S209G, and K65E/K97M/G103S/G344D). Specific activity of mutants was lower than that of the wild-type, except K65E/K97M/G103S/G344D (Table 1).

TABLE 1

Specific activities of wild type AppA2 and mutants.

| Phytase | Specific activity[a] (U mg$^{-1}$) |
|---|---|
| WT | 1003.3 ± 8.0 |
| K46E | 741.6* ± 4.1 |
| K97M | 208.5* ± 3.4 |
| V227A | 899.7* ± 6.6 |
| G344D | 273.8* ± 2.7 |
| K65E/K97M/S209G | 904.7* ± 11.0 |
| K65E/K97M/G103S/G344D | 1042.1* ± 2.6 |

[a] The values represent mean ± standard error (n = 3).
An asterisk indicates a difference (P < 0.05) from wild-type.

D. Protein Expression.

Mutants with improved thermostability were further expressed in *P. pastoris* X-33 for protein purification and characterization. The transformation, culture, and induction of plasmid pPAα2 for the expression of the appA2 gene in *P. pastoris* X33 were performed as described previously (Rodriguez, E., et al., *Arch. Biochem. Biophys.* 365:262-267 (1999b)). The pGAPZαA vector containing the appA2 mutant gene (10 µg) was linearized by the restriction enzyme BspH I and transformed into *P. pastoris* X33 by electroporation. The transformed cells were plated onto YPD agar (1% yeast extract, 2% peptone, and 2% dextrose) plus zeocin (100 µg ml$^{-1}$) and incubated at 30° C. for 3 days. Single colonies of the transformants were inoculated into YPD expression media and incubated at 30° C. for 2 days for phytase expression. Phytase activity was measured and the transformants with high activity were selected for further purification. The selected transformants were cultured in YPD expression media at 30° C. from 48 to 72 h.

E. Protein Purification.

The cultures containing phytases overexpressed in *P. pastoris* X33 were centrifuged at 12,000×g for 30 min and the supernatants were concentrated (approximately 15-fold) by ultrafiltration (molecular weight cutoff 30 KDa). The concentrate was subjected to dialysis in 25 mM glycine-HCl buffer, pH 3.2 and Macro-Prep high S cation exchange chromatography (Bio-Rad Laboratories, Hercules, Calif.). Protein was purified by running the S column twice with 25 mM glycine-HCl buffer at pH 3.2 and 3.5, respectively. The proteins were eluted in 25 mM glycine-HCl buffer with a linear gradient of NaCl from 0 to 1 M. Before running the second S column, pooled peak fractions from the first run were dialyzed in 25 mM glycine-HCl buffer, pH 3.5. The final peak fractions were pooled and concentrated down to less than 2 ml by amicon centrifugal device (Millipore Co.). Protein concentrations were obtained from the absorbance at 280 nm using an extinction coefficient ($\epsilon$=50,460 M$^{-1}$ cm$^{-1}$).

F. Thermostability Assay.

Purified enzymes were diluted in 25 mM glycine-HCl buffer, pH 3.5 to 5 µg protein per ml. The diluted enzymes were incubated for 10 min at each of the following temperatures: 50, 60, 70, and 80° C. Immediately after heat treatment, the enzymes were placed on ice for 30 min (Han, Y. M., and X. G. Lei, *Arch. Biochem. Biophys.* 364:83-90 (1999); Han, Y. M., et al., *Appl. Environ. Microbiol.* 65:1915-1918 (1999)). The remaining phytase activity was measured at 37° C. and pH 3.5 as described previously (Han, Y. M., et al., *Appl. Environ. Microbiol.* 65:1915-1918 (1999)).

G. Thermostability Profiles of Error-Prone PCR Mutants.

The six selected error-prone PCR mutants were expressed in *P. pastoris* and further characterized. Each of the mutants showed improved residual activity compared to the wild-type enzyme, as the incubation temperature increased (FIG. 1). K46E and K65E/K97M/S209G displayed highest residual activity with a 25% improvement compared to that of the wild-type enzyme after being heated at 80° C. for 10 min (P<0.05). Optimum temperature for each mutant remained unchanged as did that of wild-type (data not shown).

H. pH Profile and Temperature Optimum.

The pH profile of phytase was determined at 37° C. using three different buffers: 0.2 M glycine-HCl buffer for pH 2.0-3.5, 0.2 M sodium citrate buffer for pH 4.0-6.5, and 0.2 M imidazole-HCl, pH 7.0. Purified enzymes were diluted with each buffer of different pH to give an activity of 0.2 U ml$^{-1}$. The optimal temperature was determined in 0.2 M glycine-HCl, pH 3.5 at 37, 45, 55, 60, 65, 75, and 85° C.

The pH profiles of most of the mutants except K46E and K65E/K97M/S209G remained largely unchanged (FIG. 2). Enzyme activity of K46E and K65E/K97M/S209G started to decrease at pH 4.5. At pH 4.5, K46E and K65E/K97M/S209G retained about 35% and 40% of the activity at pH 3.5, respectively, whereas they showed higher activity at pH 2.5 than the wild-type.

I. Determination of Kinetic Parameters.

Purified enzymes were diluted with 0.2 M glycine-HCl buffer, pH 3.5 to a final concentration of 0.2 U ml$^{-1}$. Phytase assay was performed using sodium phytate as substrates at 6 different concentrations ranging from 100 to 2,500 µM (100, 250, 500, 750, 1,000, and 2,500 µM). Six parallel reactions were carried out with different phytase hydrolysis reaction times from 0, 2, 4, 6, 10, to 15 min. Initial velocities were calculated from the linear region of the phytase hydrolysis curve (released inorganic phosphorus concentration vs. time) and plotted against substrate concentration. Double reciprocal transformation was performed to make a Lineweaver-Burk plot (1/Vo vs. 1/[S]) and to calculate $V_{max}$ and $K_m$ (Bisswanger, H., p. 51-74. Willey-VCH, Weinheim, Germany (2002); Ullah, A. H. J., and B. Q. Phillippy, *J. Agric. Food Chem.* 42:423-425 (1994)). Purity of enzyme was determined by SDS-PAGE (data not shown).

The kinetic parameters of the thermostable mutants (K46E and K65E/K97M/S209G) were determined at pH 3.5 along with wild-type AppA2 (Table 2). The $K_m$ values of K46E and K65E/K97M/S209G for sodium phytate at pH 3.5 were 47 and 50% lower than that of wild-type, respectively. The 26% reduction in specific activity of the mutant K46E was probably caused by a decrease in turnover number. Although the $k_{cat}$ of K46E was lower than that of the wild-type enzyme, its overall catalytic efficiency ($k_{cat}/K_m$) was 82% higher than that of the wild-type enzyme due to the decrease in $K_m$. The mutant K65E/K97M/S209G also showed 86% higher overall catalytic efficiency ($k_{cat}/K_m$) than that of wild-type.

Table 2A. Kinetic parameters and melting temperature (Tm) of the WT and error-prone PCR mutants

| Variant | Vmax(mM/min) | Km(mM) | kcat(m − 1) | kcat/Km(m − 1 mM − 1) | T(m)(° C.) |
|---|---|---|---|---|---|
| WT | 104.2 ± 0.5 | 217.6 ± 7.2a | 52347 ± 10a | 240.7 ± 8.0b | 62.4 |
| E1 | 99.7 ± 2.1 | 120.5 ± 1.7b | 52803 ± 1105a | 438.4 ± 10.4a | 68.6 |
| E20 | 103.1 ± 1.8 | 108.9 ± 13.3b | 48411 ± 856b | 448.4 ± 46.9a | 69.8 |

-continued

Table 2B. Comparison of kinetics of wild-type AppA2 and mutants [a]

| Phytase | $V_{max}$ ($\mu$mol m$^{-1}$mg$^{-1}$) | $K_m$ ($\mu$M) | $k_{cat}$ (m$^{-1}$) | $K_{cat}/K_m$ (m$^{-1}\mu$M$^{-1}$) |
|---|---|---|---|---|
| WT | 972.2[a] ± 3.2 | 217.6[a] ± 4.2 | 52519[a] ± 173 | 241.5[b] ± 4.6 |
| K46E | 896.5[b] ± 9.1 | 108.9[b] ± 7.7 | 48411[b] ± 494 | 448.4[a] ± 27.1 |
| K65E/K97M/S209G | 979.7[a] ± 11.4 | 120.5[b] ± 1.0 | 52803[a] ± 638 | 438.4[a] ± 6.0 |

Kinetic parameters: means with different letters P < 0.05
[a] Enzyme reactions (n = 3) were conducted at 37° C. in 0.2 M glycine-HCl buffer, pH 3.5 using various sodium phytate concentrations (100 μM to 2500 μM) and 200 mU phytase per ml reaction mixture.
Values represent mean ± standard error.
Different letters indicate differences (P < 0.05) within the column.

Hydrolysis of Phytate-Phosphorus in Soybean Meal.

The hydrolysis efficiency of the phytate substrate in soybean meal was determined by incubating feed sample with phytase at a ratio of 500 U kg$^{-1}$ in 0.2 M glycine-HCl buffer, pH 2.0, and 3.5 at 37° C. for 30, 60, 90, 120, and 180 min. The actual pHs of the mixture of soybean meal and buffer under two different conditions were estimated to be 3.8, and 5.5, respectively. Soybean meal (0.5 g) was dissolved in 5 ml buffer and incubated at 37° C. for 10 min. After adding phytase, the mixture was incubated for different hydrolysis time as described above. For the blank (background), glycine-HCl buffer was added instead of phytase enzyme and the reaction mixture was incubated at 37° C. as the same as the samples. The reaction was stopped by adding an equal volume of 15% trichloroacetic acid. The reaction mixture was centrifuged and the released inorganic phosphorus in the supernatant was measured as described previously. The amount of the released inorganic phosphorus of the blank was subtracted from that of samples.

When incubated in 0.2 M glycine-HCl, pH 2.0 buffer for 180 min, the K46E and K65E/K97M/S209G mutant enzymes released more inorganic phosphorus from soy phytate than wild-type (FIG. 4). However, wild-type showed higher hydrolysis efficiency than the mutants at pH 3.5.

K. Differential Scanning Calorimetry (DSC).

Melting temperatures ($T_m$) of wild-type AppA2 and mutant phytases were determined with a DSC Q10 (TA instruments, New Castle, Del.) differential scanning calorimeter equipped with refrigerated cooling system (RCS) and Thermal Advantage™ for Q Series™ software. Protein samples were concentrated to 40 mg/ml in 25 mM glycine-HCl buffer, pH 3.5 using Microcon filter device (YM-10, Millipore Co.). Each protein sample was weighed and sealed in a stainless steel pan, equilibrated to 30° C. followed by isothermaling for 2 min. The scanning condition was modified from a previously published method (Garrett, J. B., et al., Appl. Environ. Microbiol. 70:3041-6 (2004)). The proteins were scanned from 30° C. to 100° C. at a heating rate of 10° C./min. A pan containing 25 mM glycine-HCl buffer, pH 3.5 was used as a reference. Data were collected at a rate of 0.1 sec per point.

The enzymes were scanned from 30 to 100° C. The midpoint of the thermal unfolding ($T_m$) increased by about 7° C. for K65E/K97M/S209G and 6° C. for K46E, compared to wild-type AppA2 (FIG. 3).

The six selected mutants showed improved thermostability compared to wild-type, as the incubation temperature increased. In particular, the K46E and K65E/K97M/S209G mutant enzymes showed a 25% improvement in thermostability over the wild-type enzyme after being heated at 80° C. for 10 min. Consistently, the melting temperatures ($T_m$) of these mutants increased by 6-7° C. compared to that of the wild-type enzyme. The K46E and K65E/K97E/S209G mutant enzymes showed 82 and 86% higher overall catalytic efficiency ($k_{cat}/K_m$) over wild-type, respectively, indicating that the catalytic efficiency was not necessarily inversely related to thermostability. The improved catalytic efficiency of both mutants was consistently observed in the hydrolysis of phytate-phosphorus in soybean meal. They showed higher efficiency toward hydrolysis of phytate-phosphorus in soy bean meal at pH 3.8. The pH profiles of mutants mostly remained unchanged except K46E and K65E/K97E/S209G. Enzyme activity of K46E and K65E/K97E/S209G started to decrease at pH 4.5. While not wishing to be bound by theory, since Lys46 is one of the amino acids involved in phytate binding to the scissile phosphate (Lim, D., et al., Nat. Struct. Biol. 7:108-13 (2000)), at pH 5.0-5.5 negatively charged substituted Glu46 may provide a repulsive environment for the highly negatively charged substrate phytate, thereby decreasing enzyme activity. However, the reason for the decreased activity of the K65E/K97E/S209G mutant enzyme is not clear.

Figure 5:
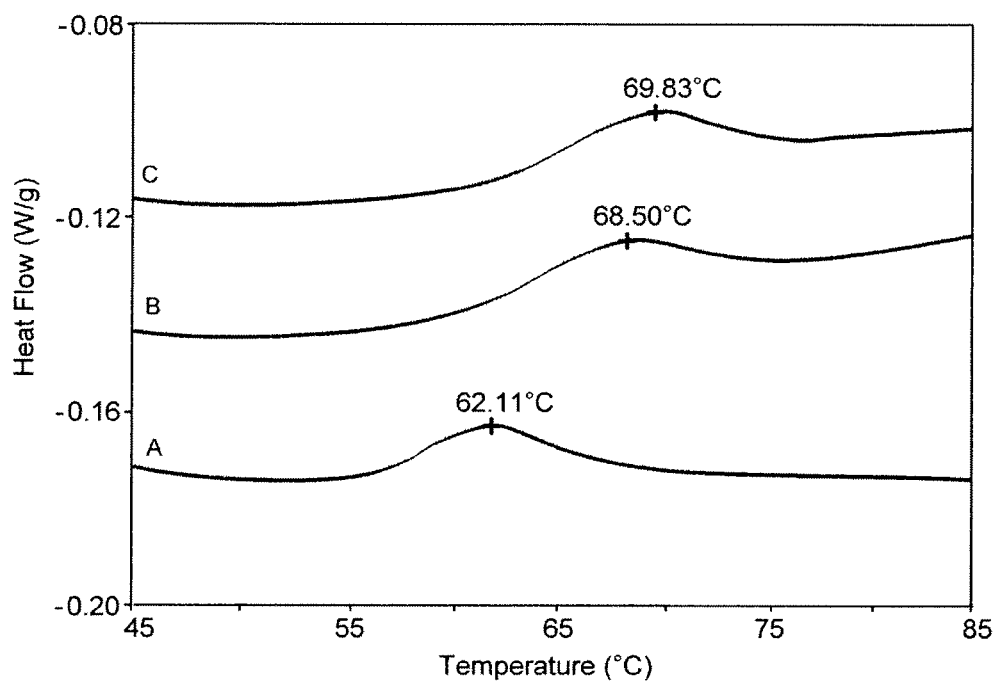
FIG. 5 shows the melting temperatures ($T_m$) of wild-type AppA2 and mutants. The thermographs shown represent wild-type AppA2 (A), K46E (B), and K65E/K97M/S209G (C).

The identified amino acid substitutions are distributed throughout the structure of a highly homologous E. coli AppA (Lim, D., et al., Nat. Struct. Biol. 7:108-13 (2000)) (FIG. 5). Most of the mutations are found in loops or surface regions. The only exception is the substitution of V227A that is located on a β-strand of α-domain. While not wishing to be bound by theory, the following is postulated to explain the improved thermostability with respect to the various substitutions and combinations thereof.

Figure 6:
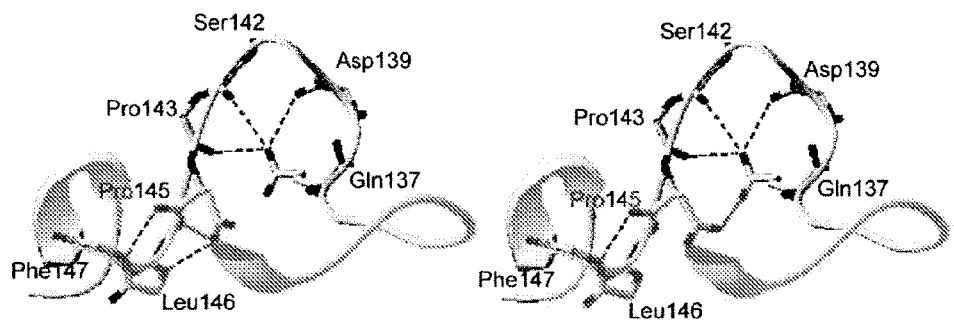
FIG. 6A-6D shows structural predictions of residue interactions in *E. coli* phytase (Lim et al., *Nat. Struct. Biol.* 7: 108-113 (2000)) before and after substitutions at K46E (A), K65E (A), V227A (B), G344D (C) and D144N (D). The three-dimensional images were prepared using the Swiss-Pdb viewer. Dotted lines indicate hydrogen bonds.

Based on the structural predictions (FIG. 6A), K46E introduces two hydrogen bonds to Ala47, whereas K65E forms three additional hydrogen bonds to adjacent residues. The side chain of Glu65 forms a hydrogen bond with the NH group of Trp68 and two hydrogen bonds with Leu66. Because K65E and Trp68 are located on the α-domain and the α/β-domain, respectively, hydrogen bonds between these residues might stabilize the interaction between the α-domain and the α/β-domain. The newly formed hydrogen bonds between K65E and Leu66 as well as between K46E and Ala47 might contribute to stabilize the local structure and then improve thermostability. The substitution S209G is predicted to contribute to improved thermostability by relieving possible steric strain which Ser209 may have with its neighbors such as Cys210 and Ser211. Mutants with substitutions such as K97M, G103S, V227A, and G344D showed some improvement in thermostability, compared to wild-type. The K97M substitution might remove structural hindrance caused by bulky side chains between Lys97 and Lys96 which are present next to each other. Val227 is located on a β-strand of the α/β-domain where the amino acid residues form a unique β-hairpin structure (FIG. 6B) and the hydrogen bonds to each other to stabilize the local structure. The replacement of Val with Ala that has a smaller side chain might eliminate structural hindrance between Val222 and Val227 which face each other in the β-hairpin structure. Gly344 located on the loop forms hydrogen bonds with Leu340 and Leu379 (FIG. 6C). The G344D substitution is predicted to form an additional side chain-side chain hydrogen bond to Leu379 which is located on the α-helix. The additional side chain-side chain hydrogen bond may contribute to stabilize local interactions.

The mutations in K65E/K97M/S209G are predicted to improve thermostability by relieving possible steric strain and increasing the number of hydrogen bonds. The stabilizing effect of a substitution of Ser209 by glutamate was also found in the stability study of AmpC β-lactamase (Beadle, B. M., and B. K. Shoichet, *J. Mol. Biol.* 321:285-96 (2002)). In that study, a single mutation (S64G) resulted in increasing a melting temperature by 6.8° C. In the wild-type enzyme, the Ser64 might cause poor electrostatic complementarity with its neighbors. After substituting with glycine, the unfavorable interaction was lost. It is supported by the study of Dominy et al. (2004) that electrostatic interactions play an important role in determining the stability of proteins at high temperatures (Dominy, B. N., et al., *Proteins: Struct., Funct., Bioinf.* 57:128-141 (2004)). The stabilizing effect of the K46E substitution can be attributed to the introduction of an additional hydrogen bond. Stabilization by this substitution has also been shown in the AmpC β-lactamase stability study (Beadle, B. M., and B. K. Shoichet, *J. Mol. Biol.* 321:285-96 (2002)). The K67E substitution stabilized the enzyme at the lower pH and increased its melting temperature by 3.9° C.

Increased thermostability has been suggested to be correlated with higher number of hydrogen bonds and salt bridges in numerous studies (Kumar, S., et al., *Proteins* 38:368-83 (2000); Kumar, S., et al., *Protein Eng* 13:179-91 (2000); Vieille, C., and G. J. Zeikus, *Microbiol. Mol. Biol. Rev.* 65:1-43 (2001); Vogt, G., et al., *J. Mol. Biol.* 269:631-43 (1997); Yip, K. S., et al., *Structure* 3:1147-58 (1995)). In the present study, the increased number of hydrogen bonds created by an acidic residue resulted in two thermostable mutants containing K46E and K65E/K97M/S209G which were located on the surface loop regions. Based on the structure of a heat-resistant *A. fumigatus* phytase (Xiang, T., et al., *J. Mol. Biol.* 339:437-45 (2004)), the high thermostability of the enzyme could be attributed to three critical regions which involve increasing the number of hydrogen bonding interactions created by acidic residues and salt-bridge interactions. These structural features of *A. fumigatus* phytase explain a difference in the thermostability between *A. niger* phytase and *A. fumigatus* phytase that share 66% sequence identity and very similar overall structure. The critical regions in *A. fumigatus* phytase are located on the surface-exposed turns and/or loops, which could be correlated with the refolding capability of the protein (Xiang, T., et al., *J. Mol. Biol.* 339:437-45 (2004)).

In addition, the catalytic efficiency of K46E and K65E/K97M/209G was improved. While not wishing to be bound by theory, it is assumed that removal of a bulky side chain of Lys46 and Lys65 in the K46E and K65E/K97M/209G mutants, respectively, might provide more conformational flexibility toward substrate binding area, thereby resulting in improved catalytic efficiency. Single surface mutations can be relatively easily accommodated in the protein structure without compensating changes (Zhao, H., and F. H. Arnold, *Protein Eng.* 12:47-53 (1999)). The present results are also consistent with the simultaneous improvements in thermostability and catalytic activity of other enzymes (Giver, L., et al., *Proc. Natl. Acad. Sci. USA* 95:12809-13 (1998); Song, J. K., and J. S. Rhee, *Appl. Environ. Microbiol.* 66:890-4 (2000); Zhao, H., and F. H. Arnold, *Protein Eng.* 12:47-53 (1999)).

Thus, both properties can be fairly independent and may not be incompatible in a given enzyme (Giver, L., et al., *Proc. Natl. Acad. Sci. USA* 95:12809-13 (1998)). In view of the above, directed evolution can be applied to create thermostable phytase through several key amino acid substitutions. The improved variants will survive the high temperature exposure during feed-pelleting, rendering the enzyme supplementation in animal feed more economical.

In summary, then, phytases have been used to improve the phosphorus nutrition of food animals and reduce their phosphorus excretion to the environment. While other phytase enzymes are also of interest, *Escherichia coli* AppA2 phytase is of particular interest for biotechnological applications due to a favorable pH optimum, high catalytic efficiency, and strong pepsin resistance. The objective of this study was to enhance AppA2 phytase thermostability for an improved tolerance to heat inactivation of feed pelleting by directed evolution. After a mutant library of AppA2 was generated by error-prone PCR, variants were initially expressed in *Saccharomyces cerevisiae* and screened for improved thermostability using a 96-well plate assay. Selected candidates were expressed in *Pichia pastoris*, purified, and further characterized. Two mutants (K46E and K65E/K97M/S209G) showed over 20% improvement in thermostability when heated at 80° C. for 10 min, compared with the wild-type enzyme. The melting temperatures ($T_m$) of the two mutants increased approximately by 6-7° C. over wild-type. Based on the structural predictions with the structure of a highly homologous *E. coli* AppA phytase, K46E introduces a hydrogen bond with Ala47, and K65E introduces one and two additional hydrogen bonds with Trp68 and Leu66, respectively. The increased hydrogen bonds in the surface loop regions might stabilize local interactions. The S209G substitution was predicted to relieve possible steric strain which Ser209 may have with its neighbors such as Cys210 and Ser211. The K46E and K65E/K97E/S209G mutant enzymes showed 82 and 86% higher overall catalytic efficiency ($k_{cat}/K_m$) over the wild-type enzyme, respectively, indicating that the catalytic efficiency was not necessarily negatively affected by the enhanced thermostability. The improved catalytic efficiency of both mutants concurred with an enhanced hydrolysis of phytate-phosphorus in soybean meal at pH 2.0.

Example 2

Assembly of Mutations for the Improved Thermostability of *E. coli* AppA2 Phytase

*E. coli* phytase has favorable characteristics for animal feed application, and has been shown to be more effective for releasing phytate-phosphorus in young chickens and pigs than two commercial phytases derived from *A. niger* and *Peniophora lycii* (Augspurger, N. R., et al., *J. Anim. Sci.* 81:474-483 (2003)). Thus, the inventors have focused on *E. coli* AppA2 phytase engineering to develop an ideal phytase with improved thermostability. In the study described in Example 1, directed evolution was used to improve the thermostability of AppA2. Two mutants (K46E and K65E/K97M/S209G) showed a significant improvement in thermostability. Their melting temperatures ($T_m$) were increased by 6-7° C. over the wild-type enzyme. Other mutations were also identified with smaller positive effects on thermostability. Structural changes induced by each residue substitution were predicted using a highly homologous structure of *E. coli* phytase (Lim, D., et al., *Nat. Struct. Biol.* 7:108-13 (2000)). Based on the structural predictions, mutations such as K46E, K65E, D112N, D144N, and G344D introduced one or two hydrogen bonds. The S209G and V227A substitutions were predicted to relieve steric strain or structural hindrance which they might have with their neighboring amino acids.

Substitution of several amino acids in a protein often substantially changes multiple properties of the protein. When several mutations distantly separated within an enzyme are combined, their effects on protein stability, substrate binding and protein-protein interactions can be additive (Wells, J. A., *Biochemistry* 29:8509-17 (1990)). For example, additive effects of mutations on the stability and activity of subtilisin E in nonaqueous solvents were reported (Chen, K. Q., et al., *Biotechnol. Prog.* 7:125-9 (1991)). The combination of several individual stabilizing mutations generated a thermostable chicken lysozyme, with cumulative benefits (Shih, P., and J. F. Kirsch, *Protein Sci.* 4:2063-72 (1995)). Combination of five residue substitutions resulted in additive effects on the stability of kanamycin nucleotidyltransferase (KNT), while the effects of individual mutations seem to be negligible (Hoseki, J., et al., *Biochemistry* 42:14469-75 (2003)). In contrast, no additive effect was observed for the thermodynamic properties of catalytic reaction in the multiple mutant of 3-isopropylmalate dehydrogenase (IPMDH) (Yasugi, M., T., et al., *Protein Eng.* 14:601-607 (2001)). In the following study, a number of mutations previously identified by directed evolution and predicted to be beneficial to the thermostability of AppA2 phytase were added sequentially to the wild-type enzyme and the effects on thermostability and linetics of the enzyme were characterized.

A. Construction of AppA2 Mutants.

Figure 7:
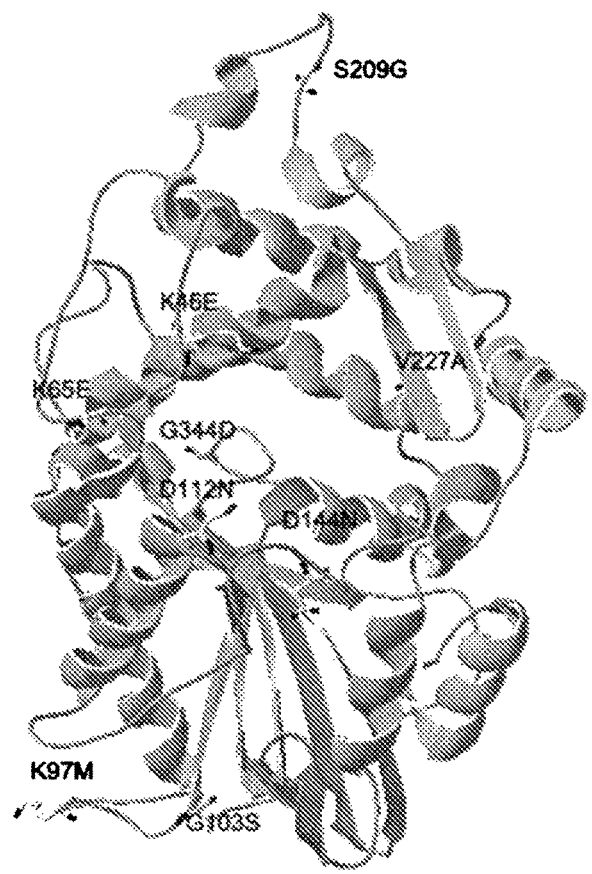
FIG. 7 shows the locations of residue substitutions K46E, K65E, K97M, D112N, D144N, G103S, S209G, V227A, and G344D in the structure of *E. coli* phytase (Lim et al., *Nat. Struct. Biol.* 7: 108-113 (2000)). The ribbon diagram of the three-dimensional structure was prepared using the Swiss-Pdb viewer.

A series of residue substitutions (K46E, K65E, G103S, D112N, D144N, S209G, V227A, and G344D shown in FIG. 7) were sequentially introduced into two existing mutants (D144N, and K65E/K97M/D112N) in parallel, based on the structural analysis of thermostabilization. The residue substitutions (K46E, K65E, G103S, S209G, V227A, and G344D) were identified in the random mutagenesis study for the enhanced thermostability of AppA2 described in Example 1. All mutants were constructed by using QuickChange® Multi Site-Directed Mutagenesis Kit (Stratagene, La Jolla, Calif.). Double stranded, dam methylated plasmid DNA, and a forward primer containing the desired point mutation were used for mutagenesis. The mutagenesis primers were extended by PfuTurbo DNA polymerase in a thermo cycling process (95° C. for 1 min; 30 cycles at 95° C. for 1 min, 55° C. for 1 min, and 65° C. for 14 min). The thermal cycling reaction products were treated by Dpn I restriction enzyme at 37° C. for 1 h to remove methylated and hemimethylated parental DNA template. The mutated single stranded DNA was transformed into *E. coli* XL10 Gold ultracompetent cells where the mutant closed circle ss-DNA is converted into duplex form in vivo. The transformation reactions were plated onto LB medium containing zeocin (25 μg ml$^{-1}$). Plasmids containing the desired mutations were verified by DNA sequencing. All primers and mutant constructs were summarized in Table 3.

TABLE 3

Strains, plasmids, and synthetic oligonucleotides

| Strains and Plasmids | Relevant genotypes | References |
|---|---|---|
| Strain | | |
| XL10-Gold | TetR Δ(mrcA) 183 Δ(mcrCB-hsdSMR-mrr)173 supE44 Thi-1 recA1 gyrA96 relA1 lac [F'proAB lacIqZΔM15 Tn10(TetR) Amy CamR] | Stratagene |
| Plasmids | | |
| pGAPZα | ColE1 on, Zeo$^R$, for integration in *P. pastoris* | Invitrogen |
| pGAPZα-appA2 | appA2 fragment cloned into the EcoR I and Xba I sites of pGAPZα | Lee et al. (2005) |
| pGAPZα-M1 | D144N/V227A substitutions of appA2 in pGAPZα-appA2 | This study |
| pGAPZα-M2 | D144N/V227A/G344D substitutions of appA2 in pGAPZα-appA2 | This study |
| pGAPZα-M3 | K65E/D144N/V227A/G344D substitutions of appA2 in pGAPZα-appA2 | This study |
| pGAPZα-M4 | K65E/D112N/D144N/V227A/G344D substitutions of appA2 in pGAPZα-appA2 | This study |
| pGAPZα-M5 | K46E/K65E/D112N/D144N/V227A/G344D substitutions Of appA2 in pGAPZα-appA2 | This study |
| pGAPZα-M3A | K46E/K65E/D144N/V227A/G344D substitutions of appA2 in pGAPZα-appA2 | This study |
| pGAPZα-M6 | K46E/K65E/G103S/D112N/D144N/V227A/G344D substitutions of appA2 in pGAPZα-appA2 | This study |
| pGAPZα-M7 | K46E/K65E/G103S/D112N/D144N/S209G/V227A/G344D substitutions of appA2 in pGAPZα-appA2 | This study |
| pGAPZα-M8 | K65E/K97M/D112N/V227A substitutions of appA2 in pGAPZα-appA2 | This study |

TABLE 3-continued

Strains, plasmids, and synthetic oligonucleotides

| Strains and Plasmids | Relevant genotypes | References |
|---|---|---|
| pGAPZα-M9 | K65E/K97M/D112N/V227A/G344D substitutions of appA2 in pGAPZα-appA2 | This study |
| pGAPZα-M10 | K65E/K97M/D112N/D144N/V227A/G344D substitutions of appA2 in pGAPZα-appA2 | This study |
| pGAPZα-M11 | K46E/K65E/K97M/D112N/D144N/V227A/G344D substitutions of appA2 in pGAPZα-appA2 | This study |
| pGAPZα-M12 | K46E/K65E/K97M/G103S/D112N/D144N/V227A/G344D substitutions of appA2 in pGAPZα-appA2 | This study |
| pGAPZα-M13 | K46E/K65E/K97M/G103S/D112N/D144N/S209G/V227A/G344D substitutions of appA2 in pGAPZα-appA2 | This study |

Oligonucleotides

| | | |
|---|---|---|
| K46E | 5'-cgtgccccaaccgaggccacgcaac-3' | (SEQ ID NO: 5) |
| K65E | 5'-caacctggccggtagaactgggttggctg-3' | (SEQ ID NO: 6) |
| G103S | 5'-ctgcccgcagcctagtcaggtcgcg-3' | (SEQ ID NO: 7) |
| D112N | 5'-gcgattattgctgatgtcaacgagcgtacccgtaaaac-3' | (SEQ ID NO: 8) |
| D144N | 5'-gatacgtccagtcccaatccgttatttaatcc-3' | (SEQ ID NO: 9) |
| S209G | 5'-gagaaacaggacgaaggctgttcattaacgc-3' | (SEQ ID NO: 10) |
| V227A | 5'-gtgagcgccgacaatgcttcattaaccggtgcg-3' | (SEQ ID NO: 11) |
| G344D | 5'-ctggacgcttccagatcagccggataacac-3' | (SEQ ID NO: 12) |

Fourteen mutants in total were constructed. All mutants were expressed in high activity in the yeast expression system except those constructs from the other existing mutant (K65E/K97M/D112N), which showed very little activity. Thus, attention was focused on further purification and characterization of AppA2 mutants including M1, M2, M3, M4, M5, M3A, M6, and M7 (Table 3). Specific activity of these mutant enzymes is summarized in Table 4. Three mutants: M1 (D144N/V227A), M4 (K65E/D112N/D144N/V227A/G344D), and M7 (K46E/K65E/G103S/D112N/D144N/S209G/V227A/G344D) had 38, 7, and 23% higher specific activity than the wild-type enzyme, respectively.

TABLE 4

Specific activity of wild-type AppA2 and AppA2 variants at pH 3.5$^a$

| Phytase | Specific activity (U mg$^{-1}$) |
|---|---|
| WT | 1003.3 ± 8.0 |
| M1 (D144N/V227A) | 1384.9* ± 18.8 |
| M2 (D144N/V227A/G344D) | 806.6* ± 20.1 |
| M3 (K65E/D144N/V227A/G344D) | 715.8* ± 13.9 |
| M3A (K46E/K65E/D144N/V227A/G344D) | 686.4* ± 16.9 |
| M4 (K65E/D112N/D144N/V227A/G344D) | 1073.6* ± 5.9 |
| M5 (K46E/K65E/D112N/D144N/V227A/G344D) | 859.4* ± 4.2 |
| M6 (K46E/K65E/G103S/D112N/D144N/V227A/G344D) | 714.5* ± 12.0 |
| M7 (K46E/K65E/G103S/D112N/D144N/S209G/V227A/G344D) | 1229.0* ± 4.4 |

$^a$represents mean ± standard error (n = 3).
An asterisk indicates a difference (P < 0.05) from wild-type.

Transformation and protein expression and purification of the AppA2 mutant polypeptides for this study were performed in the same manner as in Example 1.

B. SDS-PAGE and Glycosylation Analysis.

Purified protein samples were subjected to 12% SDS-PAGE using a Mini-Protein II cell (Bio-Rad Laboratories, Hercules, Calif.) to check the level of glycosylation of each mutant. Deglycosylation of proteins were performed by incubation with endoglycosidase H$_f$ (Endo H$_f$) for 2.5 h at 37° C. according to the manufacturer's instructions (New England Biolabs, Beverly, Mass.). Proteins in SDS-PAGE were stained with Coomassie brilliant blue R-250.

The glycosylation level of each purified mutant remained unchanged (FIG. 8).

C. Thermostability Profiles of Mutant Phytases.

The thermostability of mutant phytase enzymes was assayed in the same manner as in Example 1. All mutant enzymes except M7 showed improved thermostability compared to the wild-type enzyme after being heated at 80° C. for 10 min (P<0.05) (FIG. 9). Among them, the mutant enzymes M1 (D144N/V227A), M2 (D144N/V227A/G344D) and M3A (K46E/K65E/D144N/V227A/G344D) displayed a 17-19% improvement in residual activity compared to that of the wild-type enzyme. Mutants M1 and M2 were selected for further measurement of melting temperatures (T$_m$).

D. pH Profile.

The pH profiles of mutant phytase enzymes were determined in the same manner as in Example 1. The pH profiles of the mutant enzymes except M3A (K46E/K65E/D144N/V227A/G344D), M5 (K46E/K65E/D112N/D144N/V227A/G344D), M6 (K46E/K65E/G103S/D112N/D144N/V227A/G344D), and M7 (K46E/K65E/G103S/D112N/D144N/S209G/V227A/G344D) remained largely unchanged (FIG.

10). The M3A, M5, and M6 mutant enzymes showed a decrease in activity at pH 5.0 and higher, compared to the wild-type enzyme. At pH 5.0, the enzyme activities of M3A, M5, and M6 were 54, 59, and 55% lower than that of the wild-type enzyme, respectively. Enzyme activity of the mutant M7 at pH 4.5 was 43% lower than that of wild-type. At pH 5.0 or higher, it showed 65% lower activity over wild-type.

E. Determination of Kinetic Parameters.

Purified enzymes were diluted with 0.2 M glycine-HCl buffer, pH 3.5 to a final concentration of 0.2 U ml$^{-1}$. Phytase assay was performed using sodium phytate as substrates at 6 different concentrations ranging from 100 to 2,500 µM (100, 250, 500, 750, 1,000, and 2,500 µM). Six parallel reactions were carried out with different phytase hydrolysis reaction times from 0, 2, 4, 6, 10, to 15 min. Initial velocities were calculated from the linear region of the phytase hydrolysis curve (released inorganic phosphorus concentration vs. time) and plotted against substrate concentration. Double reciprocal transformation was performed to make a Lineweaver-Burk plot (1/Vo vs. 1/[S]) and to calculate $V_{max}$ and $K_m$ (Bisswanger, H, p. 51-74, Willey-VCH, Weinheim, Germany (2002); Ullah, A. H. J., and B. Q. Phillippy, *J. Agric. Food Chem.* 42:423-425 (1994)).

The kinetic parameters of the thermostable mutants, M1 (D144N/V227A) and M2 (D144N/V227A/G344D), were determined at pH 3.5 along with wild-type AppA2 (Table 5). The $K_m$ values of M1 and M2 mutant enzymes for sodium phytate at pH 3.5 were 141.3 and 86.4 µM, respectively, which were 35 and 60% lower than that of wild-type (P<0.05). This resulted in 87 and 171% higher overall catalytic efficiency ($k_{cat}/K_m$) for M1 and M2, respectively, compared to the wild-type enzyme.

TABLE 5

Comparison of kinetics of wild-type AppA2 and AppA2 variants [a]

| Phytase | $V_{max}$ (µmol m$^{-1}$mg$^{-1}$) | $K_m$ (µM) | $k_{cat}$ (m$^{-1}$) | $k_{cat}/K_m$ (m$^{-1}$µM$^{-1}$) |
|---|---|---|---|---|
| WT | 972.2$^c$ ± 3.2 | 217.6$^a$ ± 4.2 | 52519$^c$ ± 173 | 241.5$^c$ ± 4.6 |
| M1 | 1175.6$^a$ ± 13.8 | 141.3$^b$ ± 8.3 | 63505$^a$ ± 749 | 451.9$^b$ ± 22.1 |
| M2 | 1016.3$^b$ ± 5.5 | 86.4$^c$ ± 1.5 | 54891$^b$ ± 296 | 653.3$^a$ ± 8.8 |

[a]Enzyme reactions (n = 3) were conducted at 37° C. in 0.2 M glycine-HCl buffer, pH 3.5 using various sodium phytate concentrations (100 µM to 2500 µM) and 200 mU phytase per ml reaction mixture.
Values represent mean ± standard error.
Different letters indicate differences (P < 0.05) within the column.

Hydrolysis of Phytate-Phosphorus in Soybean Meal.

Figure 12:
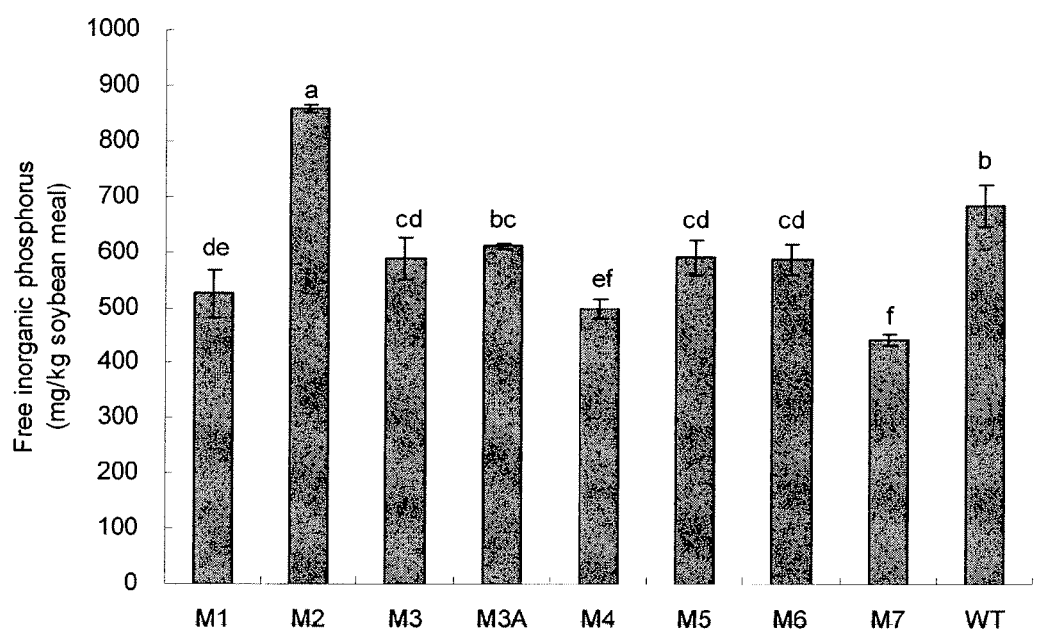
FIG. 12 shows the efficiency of phytate-phosphorus hydrolysis in soybean meal with wild-type AppA2 and AppA2 variants at enzyme concentration of 500 U per kg soybean meal. Soybean meal was incubated in 0.2 M glycine-HCl buffer, pH 2.0 buffer at 37° C. for 1 h. Bars not sharing a common letter are different (P<0.05).

The efficiency of hydrolysis of phytate was measured in the same manner as in Example 1. The mutant enzyme M2 (D144N/V227A/G344D) released 25% more inorganic phosphorus from soy phytate than the wild-type enzyme (P<0.01) (FIG. 12). The mutant enzyme M3A (K46E/K65E/D144N/V227A/G344D) released a similar amount of inorganic phosphorus compared to wild-type. The other mutant enzymes including M1, M3, M4, M5, M6, and M7 showed lower efficiency for soy phytate hydrolysis than the wild-type enzyme.

G. Melting Temperatures.

Figure 11:
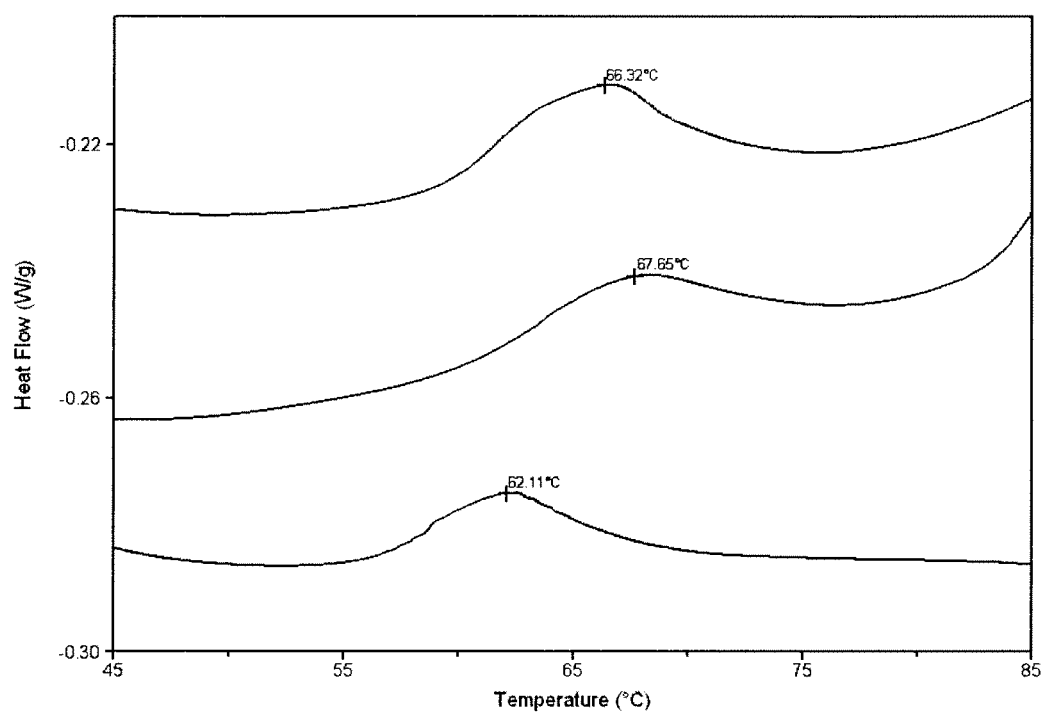
FIG. 11 shows the melting temperatures ($T_m$) of wild-type AppA2 and AppA2 variants. The thermographs represent wild-type AppA2 (A), M1 (D144N/V227A) (B), and M2 (D144N/V227A/G344D) (C).

The melting temperatures of the mutant phytases were examined in the manner described in Example 1. The midpoint of the thermal unfolding ($T_m$) increased by about 5° C. for M1 (D144N/V227A) and 4° C. for M2 (D144N/V227A/G344D), compared to wild-type AppA2 (FIG. 11).

Among the eight mutant enzymes created and characterized in this study, the M1 (D144N/V227A) and M2 (D144N/V227A/G344D) mutant enzymes showed more than a 15% improvement in thermostability compared to the wild-type enzyme after being heated at 80° C. for 10 min. Consistently, their melting temperatures ($T_m$) increased by 5 and 4° C., respectively, over wild-type. However, adding more mutations to the M2 (D144N/V227A/G344D) mutant enzyme resulted in no additive effect on thermostability. The M1 and M2 mutant enzymes showed 87 and 171% higher overall catalytic efficiency ($k_{cat}/K_m$) over the wild-type enzyme, respectively, indicating that the catalytic efficiency was not negatively affected by improved thermostability. The improved catalytic efficiency of the mutant enzyme M2 (D144N/V227A/G344D) was consistently observed in the hydrolysis of phytate-phosphorus in soybean meal as the M2 mutant enzyme released 25% more inorganic phosphorus than the wild-type enzyme. The pH profiles of the M1 and M2 mutant enzymes remained largely unchanged. However, four mutant enzymes containing a K46E substitution showed a decrease in activity at pH 5.0. While not wishing to be bound by theory, this is probably because Lys46 is one of the amino acids involved in phytate binding with the scissile phosphate (Lim, D., et al., *Nat. Struct. Biol.* 7:108-13 (2000)). At pH 5.0-5.5, negatively charged substituted Glu46 may provide a repulsive environment for the highly negatively charged substrate phytate, thereby decreasing enzyme activity.

While not wishing to be bound by theory, this and the following **XX paragraphs set out possible mechanisms behind the various improvements and changes in activity. M1 (D144N/V227A) and M2 (D144N/V227A/G344D) mutants share D144N and V227A substitutions. In structural predictions (FIG. 6D), the D144N substitution introduces a side chain-side chain hydrogen bond with Gln137 in the distance of 2.5 Å. This resulted in losing main chain-side chain hydrogen bonds that Asp144 forms with Pro145 and Leu146 before the substitution. However, a hydrogen bond between Asn144 and Phe147 still remains, which means that the loop region Gln137-Phe147 might be still held together by this hydrogen bond. Structural analysis also indicates that Gln137 is predicted to form hydrogen bonds with Asp139, Ser142, and Pro 143 which are located on the loop in close proximity. A hydrogen bond between Asn144 and Gln137 might help form the hydrogen bond network in the loop region Gln137-Asn144, thereby strengthening the formation of protein tertiary structure. This might compensate the loss of two hydrogen bonds (Asp144-Pro145 and Asp144-Leu146) which might not have a strong effect on the local folding. The replacement of Asp144 with asparagine might stabilize local interactions. The stabilizing effect of a substitution of aspartate with asparagine has also been shown in T4 lysozyme (Shoichet, B. K., et al., *Proc. Natl. Acad. Sci. USA* 92:452-6 (1995)) as a D20N substitution increased its melting temperature by 3.1° C. In addition, introducing a D375N substitution into pig citrate synthase (Zhi, W., et al., *Biochemistry* 30:9281-6 (1991)) enhanced its melting temperature ($T_m$) by 5.8° C.

The Val227 substitution is located on the β-strand of the α/β-domain where amino acid residues form a unique β-hairpin structure and are hydrogen-bonded to each other to stabilize the local structure (FIG. 6B). The replacement of Val with Ala which has a smaller side chain might eliminate structural hindrance between Val222 and Val227 that face each other in the β-hairpin structure. The mutant enzyme M1 (D144N/V227A) might improve thermostability by introducing a side chain-side chain hydrogen bond and eliminating structural hindrance.

Adding G344D to M1 did not increase thermostability, even though the substitution was predicted to introduce a side chain-side chain hydrogen bond to Leu379 (FIG. 6C). It is unclear how the interaction between adding G344D to the existing mutations (D144N/V227A) in M1 might neutralize the positive effect of G344D on thermostability. When the individual sites of mutations interact with each other by making direct contact or indirectly through electrostatic interactions, or alter the rate-determining step in catalysis, simple additive effects of combination of mutations are often not observed (LiCata, V. J., and G. K. Ackers, *Biochemistry* 34:3133-3139 (1995); Skinner, M. M., and T. C. Terwilliger, *Proc. Natl. Acad. Sci. USA* 93:10753-7 (1996); Wells, J. A., *Biochemistry* 29:8509-17 (1990)). It might be possible that D144N and G344D may interact indirectly through electrostatic interactions since both mutations are involved in forming hydrogen bonds. When K65E was introduced into M2 (D144N/V227A/G344D), the thermostability of M3 (K65E/D144N/V227A/G344D) was decreased. However, after adding K46E to M3 and M4 (K65E/D112N/D144N/V227A/G344D), the thermostability of M3A and M5 mutant enzymes slightly increased. In a previous study (Kim and Lei, in preparation), the single mutation (K46E) showed a significant increase in thermostability. However, in this study, the same improvement was not observed when the K46E substitution was introduced into multiple mutants. Likewise, the S209G substitution was beneficial to thermostability in the previous study, but showed no effect when the S209G substitution was introduced to M6 (K46E/K65E/G103S/D112N/D144N/V227A/G344D). The substituted residues might interact with one another indirectly through electrostatic interactions or structural perturbations (Wells, J. A., *Biochemistry* 29:8509-17 (1990)). Thus, these substitutions might no longer behave independently and in turn exerted no positive or additive impact. Indirect interactions include a short-range steric interaction through a mediating residue and a long distance interaction (LiCata, V. J., and G. K. Ackers, *Biochemistry* 34:3133-3139 (1995); Wells, J. A., *Biochemistry* 29:8509-17 (1990)). Minor structural perturbations can be observed sometimes at sites relatively distant from the mutation (Green, S. M., and D. Shortle, *Biochemistry* 32:10131-10139 (1993)). The lack of additive effect often occurs when the involved residue pairs are distantly separated in the surface regions (Howell, E. E., et al., *Biochemistry* 29:8561-9 (1990); LiCata, V. J., and G. K. Ackers, *Biochemistry* 34:3133-3139 (1995); Robinson, C. R., and S. G. Sligar, *Protein Sci.* 2:826-37 (1993)). This might explain why the additive effect was not observed in mutant M7 (K46E/K65E/G103S/D112N/D144N/S209G/V227A/G344D), since the stabilizing mutations K46E and S209G are distantly located in the surface loop regions.

Hydrogen bonding is one of the major determinants for protein thermostabilization. In addition, the type of hydrogen bond can be a critical parameter for thermostabilization. The importance of side chain-side chain hydrogen bonds on thermostability has been reported (Kim, Y. W., et al., *Appl. Environ. Microbiol.* 69:4866-74 (2003); Kumar, S., et al., *Protein Eng.* 13:179-91 (2000); Macedo-Ribeiro, S., et al., *J. Biol. Inorg. Chem.* 6:663-74 (2001); Ragone, R., *Protein Sci.* 10:2075-82 (2001); Vieille, C., and G. J. Zeikus, *Microbiol. Mol. Biol. Rev.* 65:1-43 (2001)). The number of side chain-side chain hydrogen bonds increases in thermophilic proteins compared to their mesophilic counterparts (Kumar, S., et al., *Protein Eng.* 13:179-91 (2000)). Ragone (2001) reported that structural preference for a side chain-side chain hydrogen bond plays an important role in protein stabilization at high temperatures. The thermostability study of *Thermus* maltogenic amylase suggested that the R26G substitution increased thermostability by changing the type of a hydrogen bond to a side chain-side chain hydrogen bond even without increasing the number of hydrogen bonds (Kim, Y. W., et al., 2003, *Appl. Environ. Microbiol.* 69:4866-74). In the present study, the D144N substitution allows Asn144 to form a side chain-side chain hydrogen bond to Gln137, stabilizing the loop region Gln137-Asn144.

The D144N and G344D substitutions were found on the loops of *E. coli* phytase. Loops are considered structural weak spots because they are likely to unfold first during thermal denaturation (Vieille, C., and J. G. Zeikus, *Trends Biotechnol.* 14:183-190 (1996)). However, loops are likely to accommodate a larger variety of stabilizing mutations than regions with higher rigidity, without disrupting the three-dimensional structure (Vieille, C., and J. G. Zeikus, *Trends Biotechnol.* 14:183-190 (1996); Voigt, C. A., et al., *Proc. Natl. Acad. Sci. USA* 98:3778-83 (2001)). Thus, stabilizing the loop regions could render overall stability to AppA2, thereby increasing thermostability without compromising catalytic efficiency.

The increased catalytic efficiency of M1 (D144N/V227A) and M2 (D144N/V227A/G344D) mutant enzymes was observed even though the mutations are not directly involved in the active site. As shown in the *E. coli* phytase structure (FIG. 7), D144N and G344D were located relatively close to the substrate binding area. Increased catalytic activity resulting from mutations outside the active site was also found in the work of Spiller et al. (1999). Mutations in a para-nitrobenzyl esterase (pNB) generated by directed evolution are found on the loops and none of them is in the active site except only one in the entrance. However, those mutations decreased the flexibility of the surface loops and reorganize the active site (Spiller, B., et al., *Proc. Natl. Acad. Sci. USA* 96:12305-10 (1999)). A similar result was also found in the structure of a mutant aspartate aminotransferase generated by directed evolution (Oue, S., et al., *J. Biol. Chem.* 274:2344-921 (1999)). The mutant enzyme showed a $2.1 \times 10^6$ fold increase in catalytic efficiency for a non-native substrate. The structural analysis indicated that mutations shifted enzyme domain that encloses the substrate, thereby remodeling the active site. They demonstrated the cumulative effects of residues remote from the active site on the catalytic efficiency. In the present study, D144N and G344D substitutions might indirectly affect the electrostatic field potential around the substrate binding site, rendering a favorable effect on substrate binding. This study demonstrates the generation of thermostable mutant enzymes with better catalytic efficiency than the wild-type enzyme by combining several substitutions. However, the lack of consistent benefit by introducing more mutations in those variants underscores the difficulty of predicting synergistic effects of multiple mutations within a protein.

To summarize the findings from this Example, then, *Escherichia coli* AppA2 phytase has favorable pH optimum, high catalytic efficiency, and strong resistance to pepsin digestion. The objective of the study was to sequentially add the random mutations previously identified (K46E, K65E, G103S, D112N, D144N, S209G, V227A, and G344D) to investigate if multiple mutations additively improved the thermostability of AppA2. Among the resulting mutants, two mutants (D144N/V227A and D144N/V227A/G344D) showed over 15% enhancement in thermostability after being heated at 80° C. for 10 min and 4-5° C. increases in the melting temperatures ($T_m$) over the wild-type enzyme. The substitution D144N introduced a side chain-side chain hydrogen bond and thus stabilized the loop region, whereas the V227A substitution might eliminate structural hindrance between Val222 and Val227 that face each other in the β-hairpin structure. Those mutants showed 87 and 171% higher overall catalytic efficiency ($k_{cat}/K_m$), respectively, over the wild-type, and the mutant D144N/V227A/G344D had a 25% increase in releasing phytate-phosphorus in soybean meal than the wild-type enzyme at pH 2.0. It should be understood that any of the single mutations described herein can increase thermal stability. However, because adding more mutations to the D144N/V227A/G344D did not further improve thermostability, the present study underscores the difficulty of predicting synergistic effects of multiple mutations within phytase.

It is to be understood and expected that variations in the principles of invention herein disclosed may be made by one skilled in the art and it is intended that such modifications are to be included within the scope of the present invention.

What is claimed:

1. An isolated phytase comprising an amino acid sequence having at least 96 percent sequence identity to SEQ ID NO:1 over a region of at least 100 amino acid residues and containing at least one substitution of at least one amino acid residue selected from the group consisting of residues 46, 65, 103, 112, 144, 209, 227, and 344 of SEQ ID NO:1.

2. The isolated phytase of claim 1, wherein said at least one substitution is a multiple substitution comprising K65E/K97M/S209G, or a conservative substitution thereof.

3. An animal feed composition comprising the isolated phytase of claim 1.

4. A foodstuff comprising an animal feed composition of claim 3.

5. An isolated *E. coli* phytase polypeptide of SEQ ID NO: 1 carrying a modification of at least one of residues 46, 65, 103, 112, 144, 209, 227, and 344, wherein said phytase has increased thermostability relative to a phytase of SEQ ID NO: 1.

6. The isolated phytase polypeptide of claim 5, wherein said modification comprises at least one of K46E, K65E, G103S, D112N, D144N, K209G, V227A, and G344D.

7. The isolated phytase polypeptide of claim 5, wherein said modification comprises modification of amino acid residues 65, 97, and 209.

8. The isolated phytase polypeptide of claim 7, wherein said modification comprises K65E/K97M/S209G.

9. An animal feed composition comprising a phytase of claim 5.

10. An isolated phytase polypeptide, wherein said phytase polypeptide comprises an amino acid sequence having at least 96 percent sequence identity to SEQ ID NO:1 over a region of at least 100 amino acid residues and containing substitutions at at least two amino acid residues corresponding to residues selected from the group consisting of residues 46, 65, 103, 112, 144, 209, 227, and 344 of SEQ ID NO:1, which phytase polypeptide has increased thermostability relative to a phytase of SEQ ID NO: 1.

11. The isolated phytase polypeptide of claim 10, wherein the phytase polypeptide comprises substitutions at residues corresponding to residues 144 and 227 of SEQ ID NO: 1.

12. An animal feed composition comprising an isolated phytase polypeptide of claim 10.

13. The isolated phytase of claim 1, wherein said at least one substitution comprises substitution of amino acid residue 46.

14. The isolated phytase of claim 1, wherein said at least one substitution comprises substitution of amino acid residue 65.

15. The isolated phytase of claim 14, wherein said at least one substitution comprises K65E, or a conservative substitution thereof.

16. The isolated phytase of claim 1, wherein said at least one substitution comprises substitution of amino acid residue 103.

17. The isolated phytase of claim 16, wherein said at least one substitution comprises G103S, or a conservative substitution thereof.

18. The isolated phytase of claim 1, wherein said at least one substitution comprises substitution of amino acid residue 112.

19. The isolated phytase of claim 18, wherein said at least one substitution comprises D112N, or a conservative substitution thereof.

20. The isolated phytase of claim 1, wherein said at least one substitution comprises substitution of amino acid residue 144.

21. The isolated phytase of claim 20, wherein said at least one substitution comprises D144N, or a conservative substitution thereof.

22. The isolated phytase of claim 1, wherein said at least one substitution comprises substitution of amino acid residue 209.

23. The isolated phytase of claim 22, wherein said at least one substitution comprises K209G, or a conservative substitution thereof.

24. The isolated phytase of claim 1, wherein said at least one substitution comprises substitution of amino acid residue 227.

25. The isolated phytase of claim 24, wherein said at least one substitution comprises V227A, or a conservative substitution thereof.

26. The isolated phytase of claim 1, wherein said at least one substitution comprises substitution of amino acid residue 344.

27. The isolated phytase of claim 26, wherein said at least one substitution comprises G344D, or a conservative substitution thereof.

28. The isolated phytase of claim 1, wherein said at least one substitution is a multiple substitution comprising K65E/K97M/G103S/G344D, or a conservative substitution thereof.

29. The isolated phytase polypeptide of claim 5, wherein said modification comprises modification of amino acid residue 46.

30. The isolated phytase polypeptide of claim 5, wherein said modification comprises modification of amino acid residue 65.

31. The isolated phytase polypeptide of claim 30, wherein said modification comprises K65E.

32. The isolated phytase polypeptide of claim 5, wherein said modification comprises modification of amino acid residue 103.

33. The isolated phytase polypeptide of claim 32, wherein said modification comprises G103S.

34. The isolated phytase polypeptide of claim 5, wherein said modification comprises modification of amino acid residue 112.

35. The isolated phytase polypeptide of claim 34, wherein said modification comprises D112N.

36. The isolated phytase polypeptide of claim 5, wherein said modification comprises modification of amino acid residue 144.

37. The isolated phytase polypeptide of claim 36, wherein said modification comprises D144N.

38. The isolated phytase polypeptide of claim 5, wherein said modification comprises modification of amino acid residue 209.

39. The isolated phytase polypeptide of claim 38, wherein said modification comprises K209G.

40. The isolated phytase polypeptide of claim 5, wherein said modification comprises modification of amino acid residue 227.

41. The isolated phytase polypeptide of claim 40, wherein said modification comprises V227A.

42. The isolated phytase polypeptide of claim 5, wherein said modification comprises modification of amino acid residue 344.

43. The isolated phytase polypeptide of claim 42, wherein said modification comprises G344D.

44. The isolated phytase polypeptide of claim 5, wherein said modification comprises K65E/K97M/G103S/G344D.

45. The isolated phytase polypeptide of claim 10, wherein the phytase polypeptide comprises substitution at the residue corresponding to residue 46 of SEQ ID NO:1.

46. The isolated phytase polypeptide of claim 45, wherein the substitution at the residue corresponding to residue 46 of SEQ ID NO:1 is K46E, or a conservative substitution thereof.

47. The isolated phytase polypeptide of claim 10, wherein the phytase polypeptide comprises substitution at the residue corresponding to residue 65 of SEQ ID NO:1.

48. The isolated phytase polypeptide of claim 47, wherein the substitution at the residue corresponding to residue 65 of SEQ ID NO:1 is K65E, or a conservative substitution thereof.

49. The isolated phytase polypeptide of claim 10, wherein the phytase polypeptide comprises substitution at the residue corresponding to residue 103 of SEQ ID NO:1.

50. The isolated phytase polypeptide of claim 49, wherein the substitution at the residue corresponding to residue 103 of SEQ ID NO:1 is G103S, or a conservative substitution thereof.

51. The isolated phytase polypeptide of claim 10, wherein the phytase polypeptide comprises substitution at the residue corresponding to residue 112 of SEQ ID NO:1.

52. The isolated phytase polypeptide of claim 51, wherein the substitution at the residue corresponding to residue 112 of SEQ ID NO:1 is D112N, or a conservative substitution thereof.

53. The isolated phytase polypeptide of claim 10, wherein the phytase polypeptide comprises substitution at the residue corresponding to residue 144 of SEQ ID NO:1.

54. The isolated phytase polypeptide of claim 53, wherein the substitution at the residue corresponding to residue 144 of SEQ ID NO:1 is D144N, or a conservative substitution thereof.

55. The isolated phytase polypeptide of claim 10, wherein the phytase polypeptide comprises substitution at the residue corresponding to residue 209 of SEQ ID NO:1.

56. The isolated phytase polypeptide of claim 55, wherein the substitution at the residue corresponding to residue 209 of SEQ ID NO:1 is K209G, or a conservative substitution thereof.

57. The isolated phytase polypeptide of claim 10, wherein the phytase polypeptide comprises substitution at the residue corresponding to residue 227 of SEQ ID NO:1.

58. The isolated phytase polypeptide of claim 57, wherein the substitution at the residue corresponding to residue 227 of SEQ ID NO:1 is V227A, or a conservative substitution thereof.

59. The isolated phytase polypeptide of claim 10, wherein the phytase polypeptide comprises substitution at the residue corresponding to residue 344 of SEQ ID NO:1.

60. The isolated phytase polypeptide of claim 59, wherein substitution at the residue corresponding to residue 344 of SEQ ID NO:1 is G344D, or a conservative substitution thereof.

61. The isolated phytase polypeptide of claim 10, wherein the phytase polypeptide further comprises substitution at the residue corresponding to residue 97 of SEQ ID NO:1.

62. The isolated phytase polypeptide of claim 61, wherein the phytase polypeptide comprises substitutions K65E, K97M, and S209G at residues corresponding, respectively, to residues 65, 97, and 209 of SEQ ID NO: 1.

63. The isolated phytase polypeptide of claim 61, wherein the phytase polypeptide comprises substitutions K65E, K97M, G103S, and G344D at residues corresponding, respectively, to residues 65, 97, 103, and 344 of SEQ ID NO: 1.

64. The isolated phytase of claim 13, wherein said at least one substitution comprises K46E, or a conservative substitution thereof.

65. The isolated phytase polypeptide of claim 29, wherein said modification comprises K46E.

* * * * *

```
                          SEQUENCE LISTING

<160> NUMBER OF SEQ ID NOS: 12

<210> SEQ ID NO 1
<211> LENGTH: 432
<212> TYPE: PRT
<213> ORGANISM: Escherichia coli

<400> SEQUENCE: 1

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
                100                 105                 110

Glu Arg Thr Arg Lys Thr Gly Glu Ala Phe Ala Ala Gly Leu Ala Pro
                115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
                180                 185                 190

Asn Phe Pro Gln Ser Asn Leu Cys Leu Asn Arg Glu Lys Gln Asp Glu
                195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
                275                 280                 285

Arg Ala Thr Pro Leu Leu Asp Leu Ile Met Ala Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335
```

```
Glu Leu Asn Trp Thr Leu Pro Gly Gln Pro Asp Asn Thr Pro Pro Gly
            340                 345                 350
Gly Glu Leu Val Phe Glu Arg Trp Arg Arg Leu Ser Asp Asn Ser Gln
        355                 360                 365
Trp Ile Gln Val Ser Leu Val Phe Gln Thr Leu Gln Gln Met Arg Asp
    370                 375                 380
Lys Thr Pro Leu Ser Leu Asn Thr Pro Pro Gly Glu Val Lys Leu Thr
385                 390                 395                 400
Leu Ala Gly Cys Glu Glu Arg Asn Ala Gln Gly Met Cys Ser Leu Ala
            405                 410                 415
Gly Phe Thr Gln Ile Val Asn Glu Ala Arg Ile Pro Ala Cys Ser Leu
            420                 425                 430

<210> SEQ ID NO 2
<211> LENGTH: 1299
<212> TYPE: DNA
<213> ORGANISM: Escherichia coli

<400> SEQUENCE: 2
atgaaagcga tcttaatccc attttatct ctttttgattc cgttaacccc gcaatctgca      60
ttcgctcaga gtgagccgga gctgaagctg aaagtgtgg tgattgtcag ccgtcatggt     120
gtgcgtgccc caaccaaggc cacgcaactg atgcaggatg tcaccccaga cgcatggcca     180
acctggccgg taaaactggg ttggctgaca ccacgcggtg gtgagctaat cgcctatctc     240
ggacattacc aacgccagcg tctggtggcc gacggattgc tggcgaaaaa gggctgcccg     300
cagcctggtc aggtcgcgat tattgctgat gtcgacgagc gtacccgtaa acaggcgaa     360 gccttcgccg ccgggctggc acctgactgt gcaataaccg tacatacccca ggcagatacg     420 tccagtcccg atccgttatt taatcctcta aaaactggcg tttgccaact ggataacgcg     480
aacgtgactg acgcgatcct cagcagggca ggagggtcaa ttgctgactt taccgggcat     540
cggcaaacgg cgtttcgcga actggaacgg gtgcttaatt ttccgcaatc aaacttgtgc     600
cttaaccgtg agaaacagga cgaaagctgt tcattaacgc aggcattacc atcggaactc     660
aaggtgagcg ccgacaatgt tcattaacc ggtgcggtaa gcctcgcatc aatgctgacg     720
gaaatatttc tcctgcaaca agcacaggga atgccgagc cggggtgggg aaggatcact     780
gattcacacc agtggaacac cttgctaagt ttgcataacg cgcaattta tttactacaa     840 cgcacgccag aggttgcccg cagtcgcgcc acccgttat tggatttgat catggcagcg     900
ttgacgcccc atccaccgca aaaacaggcg tatggtgtga cattacccac ttcagtgctg     960
tttattgccg acacgatac taatctgca atctcggcg gcgcactgga gctcaactgg    1020
acgcttccag gtcagccgga taacacgccg ccaggtggtg aactggtgtt tgaacgctgg    1080
cgtcggctaa gcgataacag ccagtggatt caggtttcgc tggtcttcca gactttacag    1140
cagatgcgtg ataaaacgcc gctatcatta atacgccgc ccggagaggt gaaactgacc    1200
ctggcaggat gtgaagagcg aaatgcgcag ggcatgtgtt cgttggccgg ttttacgcaa    1260
atcgtgaatg aagcacgcat accggcgtgc agtttgtaa                          1299

<210> SEQ ID NO 3
<211> LENGTH: 21
<212> TYPE: DNA
<213> ORGANISM: Artificial
<220> FEATURE:
<223> OTHER INFORMATION: PCR primer for cloning

<400> SEQUENCE: 3
```

```
ggaattccag agtgagccgg a                                              21
```

<210> SEQ ID NO 4
<211> LENGTH: 22
<212> TYPE: DNA
<213> ORGANISM: Artificial
<220> FEATURE:
<223> OTHER INFORMATION: PCR primer for cloning

<400> SEQUENCE: 4

```
ggtctagatt acaaactgca cg                                             22
```

<210> SEQ ID NO 5
<211> LENGTH: 25
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 5

```
cgtgccccaa ccgaggccac gcaac                                          25
```

<210> SEQ ID NO 6
<211> LENGTH: 29
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 6

```
caacctggcc ggtagaactg ggttggctg                                      29
```

<210> SEQ ID NO 7
<211> LENGTH: 25
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 7

```
ctgcccgcag cctagtcagg tcgcg                                          25
```

<210> SEQ ID NO 8
<211> LENGTH: 38
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 8

```
gcgattattg ctgatgtcaa cgagcgtacc cgtaaaac                            38
```

<210> SEQ ID NO 9
<211> LENGTH: 32
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 9

```
gatacgtcca gtcccaatcc gttatttaat cc                                  32
```

```
<210> SEQ ID NO 10
<211> LENGTH: 31
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 10
gagaaacagg acgaaggctg ttcattaacg c                                  31

<210> SEQ ID NO 11
<211> LENGTH: 33
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 11
gtgagcgccg acaatgcttc attaaccggt gcg                                33

<210> SEQ ID NO 12
<211> LENGTH: 30
<212> TYPE: DNA
<213> ORGANISM: Artificial
<220> FEATURE:
<223> OTHER INFORMATION: Synthetic oligonucleotide for site-directed
      mutagenesis

<400> SEQUENCE: 12
ctggacgctt ccagatcagc cggataacac                                    30
```